(12) United States Patent
Zhong et al.

(10) Patent No.: US 10,842,816 B2
(45) Date of Patent: Nov. 24, 2020

(54) COMPOSITIONS AND METHODS FOR ISOLATING AND ENRICHING IGM-PRODUCING CELLS AND USES THEREOF

(71) Applicants: TRUSTEES OF BOSTON UNIVERSITY, Boston, MA (US); BOSTON MEDICAL CENTER CORPORATION, Boston, MA (US)

(72) Inventors: Xuemei Zhong, Sharon, MA (US); Joyce Wong, Chestnut Hill, MA (US)

(73) Assignees: Trustees of Boston University, Boston, MA (US); Boston Medical Center Corporation, Boston, MA (US)

( * ) Notice: Subject to any disclaimer, the term of this patent is extended or adjusted under 35 U.S.C. 154(b) by 0 days.

(21) Appl. No.: 16/102,905

(22) Filed: Aug. 14, 2018

(65) Prior Publication Data

US 2019/0054120 A1 Feb. 21, 2019

Related U.S. Application Data

(60) Provisional application No. 62/545,648, filed on Aug. 15, 2017.

(51) Int. Cl.

| | | |
|---|---|---|
| *A61K 35/17* | (2015.01) | |
| *A61K 47/24* | (2006.01) | |
| *C12N 5/0781* | (2010.01) | |
| *A61K 47/69* | (2017.01) | |
| *C12N 5/16* | (2006.01) | |
| *C12N 5/09* | (2010.01) | |
| *C07K 16/30* | (2006.01) | |
| *A61P 35/00* | (2006.01) | |
| *C07K 16/00* | (2006.01) | |
| *A61P 35/02* | (2006.01) | |
| *B82Y 5/00* | (2011.01) | |

(52) U.S. Cl.
CPC .............. *A61K 35/17* (2013.01); *A61K 47/24* (2013.01); *A61K 47/6929* (2017.08); *A61P 35/00* (2018.01); *C07K 16/00* (2013.01); *C07K 16/30* (2013.01); *C12N 5/0635* (2013.01); *C12N 5/0693* (2013.01); *C12N 5/163* (2013.01); *A61P 35/02* (2018.01); *B82Y 5/00* (2013.01); *C07K 2317/52* (2013.01); *C12N 2529/00* (2013.01)

(58) Field of Classification Search
None
See application file for complete search history.

(56) References Cited

U.S. PATENT DOCUMENTS

| | | | | |
|---|---|---|---|---|
| 7,282,479 B2 * | 10/2007 | Ito | ........................... | A61K 33/26 424/646 |
| 2005/0191345 A1 * | 9/2005 | Needham | ............... | A61K 9/127 424/450 |
| 2011/0177153 A1 * | 7/2011 | Zhu | ........................ | A61K 39/44 424/450 |
| 2015/0268370 A1 * | 9/2015 | Johnston | ................ | B82Y 30/00 324/346 |
| 2016/0055946 A1 * | 2/2016 | Mattoussi | .......... | A61K 49/0067 252/62.54 |
| 2016/0194368 A1 | 7/2016 | Hoge et al. | | |
| 2016/0304829 A1 | 10/2016 | Neurauter et al. | | |
| 2017/0106088 A1 * | 4/2017 | Liu | ...................... | C12N 5/0062 |
| 2018/0223260 A1 | 8/2018 | Aprikyan et al. | | |
| 2018/0369336 A1 * | 12/2018 | Zhong | ..................... | A61P 35/00 |

FOREIGN PATENT DOCUMENTS

| | | | | |
|---|---|---|---|---|
| WO | WO-2004071386 A2 * | 8/2004 | .......... | A61K 9/0009 |
| WO | 2014066793 A1 | 5/2014 | | |
| WO | 2015130913 A1 | 9/2015 | | |
| WO | 2016134115 A1 | 8/2016 | | |
| WO | 2017096139 A1 | 6/2017 | | |
| WO | WO-2017096139 A1 * | 6/2017 | .............. | A61P 35/00 |

OTHER PUBLICATIONS

Amstad et al., Nano Let. 9(12):4042-4048 (2009).*
Craciunescu et al., Mater. Chem. Phys., 185:917-97(2017).*
Cuyper et al., Eur. Biophys. J., 15:311-319 (1988).*
Giustini et al., Nano Life, 1:01n02 (2010).*
Jin et al., Curr. Opin. Pharmacol., 18:18-27 (2014).*
Lattuada et al., Langmuir, 23:2158-2168 (2007).*
Merriam-Webster Online Dictionary, <https://merriam-webster.com/dictionary/disperse> Accessed Mar. 27, 2019.*
Peng et al., PLoS One 9(3)e92924 (2014).*
Tefft et al., JoVE, 104:e53099 (2015).*
Vo et al., Imm. Inflamm. Dis., 2(4):254-261 (2014).*
Wahajuddin et al., Int. J. Nanomedic., 7:3445-3471 (2012).*
Wang et al., J. Magnet. Magnet. Mater., 323:2953-2959 (2011).*
Wassel et al., Colloids Surfaces A: Physicochem. Eng. Aspects, 292:125-130 (2007).*

* cited by examiner

*Primary Examiner* — Thomas J. Visone
(74) *Attorney, Agent, or Firm* — Nixon Peabody LLP

(57) ABSTRACT

The technology described herein relates, at least in part, to compositions comprising and methods for isolating and enriching natural IgM-producing phagocytic B (NIMPAB) cells and methods of producing IgM antibodies using such cells, as well as uses of the antibodies produced by the methods for the prevention and treatment of diseases wherein immunotherapy with such natural IgM antibodies and their derivatives can be useful.

16 Claims, 25 Drawing Sheets

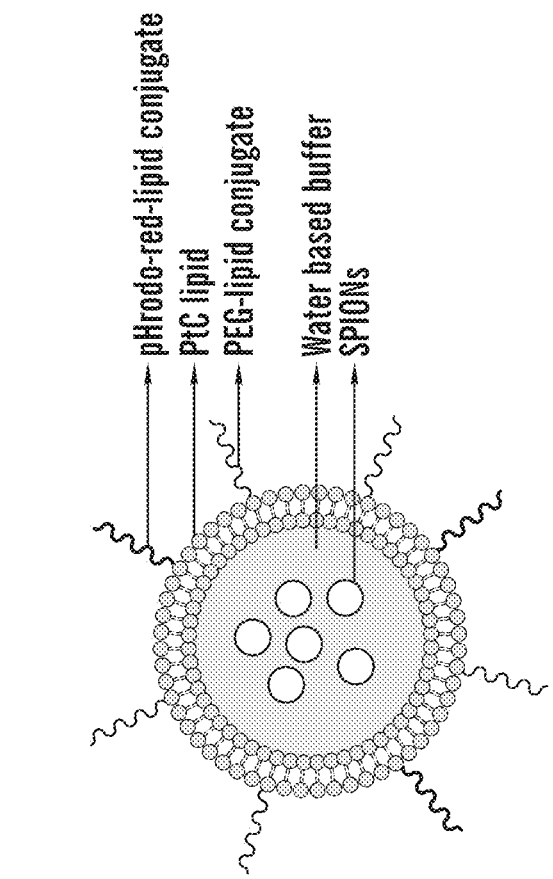
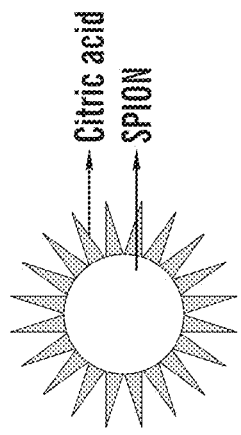
FIG. 14A
FIG. 14B
FIG. 14C

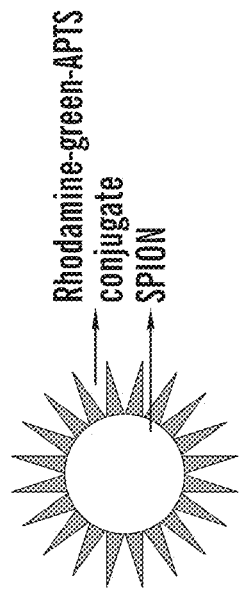
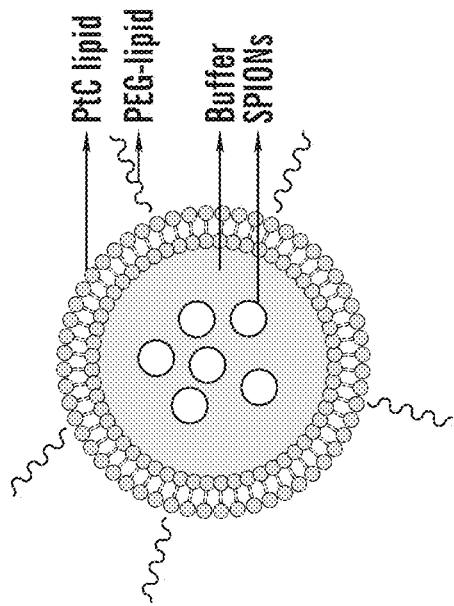
FIG. 15A
FIG. 15B

COMPOSITIONS AND METHODS FOR ISOLATING AND ENRICHING IGM-PRODUCING CELLS AND USES THEREOF

CROSS-REFERENCE TO RELATED APPLICATIONS

This application claims benefit of the U.S. patent application No. 62/545,648, filed Aug. 15, 2017, the contents of which are incorporated herein by reference in their entirety.

GOVERNMENT SUPPORT

This invention was made with government support under contract No. 1R21CA205415-01, awarded by the National Institutes of Health and National Cancer Institute. The government has certain rights in the invention.

BACKGROUND OF THE INVENTION

The naturally-existing IgM antibodies could be a novel resource that could be used in immunotherapy. However, isolating and enriching the rare B-cells that are the source of naturally-existing IgM antibodies for the production of these antibodies is an extremely labor-intensive task. For such naturally-existing IgM antibodies to become therapeutically or prophylactically useful tool in immunotherapy, improved methods must be developed.

SUMMARY OF THE INVENTION

The technology described herein relates, at least in part, to compositions and methods for isolating and enriching natural IgM-producing phagocytic B cells and methods of producing IgM antibodies using such cells as well as uses of the antibodies produced by the methods for the prevention and treatment of diseases wherein immunotherapy with such natural IgM antibodies and their derivatives can be useful.

At least part of the surprising nature of the disclosed methods is that the inventors identified a rare cell population, that produces IgM antibodies, called natural IgM-producing phagocytic B cells (NIMPAB), and discovered that these NIMPAB cells can specifically phagocytize nanoparticles comprising superparamagnetic beads in large enough quantities that allow isolation of these very rare cells using an external magnet but that also does not interfere with the cell antibody-producing function. The inventors further surprisingly found that the phagocytosis of the nanoparticles comprising superparamagnetic beads with special lipid modification is almost exclusive to a significant portion of NIMPAB cells thus allowing enrichment of these cells from complex samples comprising dissociated cells, such as dissociated tissue samples or various types of blood samples, such as peripheral or cold blood sample.

The thus-isolated and enriched NIMPAB cells can be used for large-scale production of useful IgM antibodies. For example, to allow large-scale IgM antibody production, the invention provides a method of making hybridoma cell lines with the isolated and enriched NIMPAB cells. The B-cell hybridoma cell lines can also be screened for the kinds of IgM antibodies they produce.

The methods and compositions disclosed herein allow for large scale production, and thus practical use, of IgM antibodies in treatment of diseases. The IgM antibodies can be utilized alone or in combination with other treatments as immunotherapy.

The NIMPAB cells are an important part of the body's immune surveillance system that keeps cancerous cells in check in healthy individuals. Accordingly, the technology described herein can be used in methods to generate a series of disease-type specific libraries of naturally occurring anti-disease antibodies for the treatment of a disease. The disease can be, for example, an autoimmune disease or cancer. For example, libraries of human specific IgM antibody producing NIMPAB hybridoma clones are provided.

The inventors have demonstrated that NIMPAB cells are naturally existing anti-tumor B lymphocytes exist both in human and mouse. The inventors provide in vivo data showing NIMPAB cells are actively accumulating inside tumor. The inventors have herein developed a novel platform technology for isolating, enriching, cloning and function verification of NIMPAB cells which can be used to produce desired IgM antibodies for, for example, clinical uses. Because IgM antibodies in nature are partly responsible for the prevention of diseases and do not cause inflammatory reactions as opposed to IgG antibodies, the IgM antibodies can be used not only in treatment or supportive treatment but also in the prevention of diseases or prevention of recurrence of a disease in remission.

The methods of the invention allow isolation and enrichment of cells that naturally produce IgM antibodies specific for the species. For example, when the cells are isolated from a human, no "humanization" of the resulting IgM antibodies is needed as they are already human.

The methods of the invention further allow screening for different IgM antibodies from both healthy subjects and subjects affected with a disease. This means, that the methods of the invention allow isolation and enrichment of IgM antibodies that the subject body has produced to prevent or to fight against a disease and thus allows a method of large-scale production of these antibodies for supplementing the subject's own immune surveillance. The personalized approach is only possible because the methods of the present invention allow large scale production of such IgM antibodies.

The methods of the invention are thus useful also for making IgM antibodies for treatment and prevention of disease, alone or in combination with other treatments.

The inventors demonstrate methods and compositions for rapid identification and isolation of these NIMPAB cells from peripheral blood and other tissue samples wherein cells have been dissociated, followed by cloning to generate hybridoma cells, such as human hybridoma cells. Both the isolated human NIMPAB cells and their hybridoma clones will be extremely valuable for the development of novel cancer immunotherapies that are distinct from all current commercially available immunotherapy strategies.

The present invention is directed, at least in part, to methods for isolating IgM-producing phagocytic B cells, such as IgM-producing human cells and their use in production of disease-targeting antibodies, and compositions needed for the production as well as IgM compositions produced by the methods of the invention.

For example, provided is a composition comprising a natural IgM-producing phagocytic lymphocyte (NIMPAB) cell; and at least one particle comprising a superparamagnetic iron oxide nanoparticle (SPION). The particle can be inside the NIMPAB cell, meaning, that the NIMPAB cell has taken up the particle by phagocytosis, thereby resulting in a cell that carries at least one SPION.

The SPION is dispersed in poly (lactic-co-glycolic acid (PGLA) core and the core is coated with a lipid bilayer comprising phosphatidylcholine (PtC) and polyethyleneglycol (PEG); or the SPION is dispersed in aqueous solution core and the core is coated with a lipid bilayer comprising phosphatidylcholine (PtC) and polyethyleneglycol (PEG), optionally wherein the aqueous solution core comprises a stabilizer, for example a stabilizer that is a catechol group modified poly (2-acrylamido-2-methyl-1-propanesulfonic acid) (pAMPS*) and the pH of the aqueous solution core is neutral; or the SPION is coated with citric acid and the pH of the aqueous solution core is between or at about 8 and about 9.

In some or all aspects of the invention, the NIMPAB cell is a mouse NIMPAB cell. In some or all aspects of the invention, the NIMPAB cell is a primate NIMPAB cell. In some or all aspects of the invention, the NIMPAB cell is a human NIMPAB cell.

In some or all aspects of the invention, the particle can be about 200-600 nm in diameter, for example, 200-300 nm in diameter, or for example 200-400 nm in diameter, or for example, 200-500 nm in diameter, or for example, 300-600 nm in diameter or for example 400-600 nm in diameter, or for example 500-600 nm in diameter.

In some or all aspects of the invention the SPION particles in the methods and compositions of the invention are about 10-80 nm in diameter, for example about 10 nm, 20 nm, 30 nm, 40 nm, 50 nm, 60 nm, 70 nm, or about 80 nm in diameter, for example 10-70 nm, 10-60 nm, 10-50 nm, 10-40 nm, 10-30 nm, or 10-20 nm in diameter. In some or all aspects of the invention, the SPION particles in the methods and compositions of the invention are for example 12-18 nm in diameter, for example 13-15 nm in diameter. In some aspects, when the particles is between 200-300 nm, for example, 220-230 nm, for example, about 226 nm in diameter, the SPION is 10-20 nm, for example, 13-15 nm in diameter.

In some or all aspects of the compositions and methods of the invention, when suspended in media, the SPION-comprising nanoparticles (sNPs) have an average diameter of 200-600 nm, for example, 200-300, or for example 226 nm or about 226 nm, and the SPIONs inside the nanoparticle are approximately 10-80 nm, for example 10-20 nm, for example, 13~15 nm in diameter.

In some or all aspects of the compositions the at least one particle is inside the NIMPAB cell.

The composition of claim 9, wherein the composition comprises cells of which at least 30%, at least 40%, at least 50%, at least 60%, at least 70%, at least 80%, at least 90%, or at least 95% of cells that are NIMPAB cells comprising at least one particle inside the NIMPAB cell.

The invention further provides a method or methods for producing a cell sample enriched with natural IgM-producing phagocytic lymphocyte (NIMPAB) cells, the method comprising the steps of ex vivo contacting a particle comprising a superparamagnetic iron oxide nanoparticle (SPION) with a dissociated cell sample thereby forming a mixture of the particles and dissociated cells, wherein the at least one particle comprising the SPION is dispersed in poly (lactic-co-glycolic acid (PGLA) core and the core is coated with a lipid bilayer comprising phosphatidylcholine (PtC) and polyethyleneglycol (PEG); or wherein the SPION is dispersed in aqueous solution core and the core is coated with a lipid bilayer comprising phosphatidylcholine (PtC) and polyethyleneglycol (PEG) and optionally, wherein the aqueous solution core comprises a stabilizer, for example, a catechol group modified poly (2-acrylamido-2-methyl-1-propanesulfonic acid) (pAMPS*) and wherein the pH of the aqueous solution core is neutral; or wherein the SPION is coated with citric acid and the pH of the aqueous solution core is between or at about 8 and about 9; incubating the mixture in a container to allow phagocytosis of at least one of the particles by a NIMPAB cell present in the dissociated cell sample; contacting the container with a magnet to attract the cell that has phagocytosed the particle to the part of the container in contact with the magnet; discarding the dissociated cells not attracted to the magnet thereby obtaining a cell sample enriched with NIMPAB cells; optionally dissociating the magnet and the container; optionally washing the cell sample enriched with NIMPAB cells; and optionally subjecting the cell sample enriched with NIMPAB cells to fluorescent activated cell sorting.

The dissociated cell sample may be of any animal origin, for example of any mammalian origin, for example, murine, primate or human origin.

The dissociated cell sample may be any tissue sample, such as a blood sample, such as a peripheral or cord blood sample, or a sample made of dissociated cells from a tissue sample, such as a tissue sample taken from a tumor tissue.

In some or all aspects of the methods and compositions of the invention the SPION particles in the methods and compositions of the invention are about 10-80 nm in diameter, for example about 10 nm, 20 nm, 30 nm, 40 nm, 50 nm, 60 nm, 70 nm, or about 80 nm in diameter, for example 10-20 nm in diameter. In some or all aspects of the invention, the SPION particles in the methods and compositions of the invention are for example 12-18 nm in diameter, for example 13-15 nm in diameter.

In some or all aspects of the compositions and methods of the invention, when suspended in media, the SPION-comprising nanoparticles (sNps) have an average diameter of 200-600 nm, for example, 200-300, or for example 226 nm or about 226 nm, and the SPIONs inside the nanoparticle are approximately 10-80 nm, for example 10-20 nm, for example, 13~15 nm in diameter.

In some embodiments, provided is an isolated natural IgM-producing phagocytic lymphocyte (NIMPAB) cell comprising at least one superparamagnetic iron oxide nanoparticle (SPION)-comprising nanoparticle (sNP) produced by any of the production methods as described herein.

In some embodiments, provided is a method or methods for producing tissue-specific IgM antibodies comprising the steps of producing a hybridoma cell by fusing an isolated NIMPAB cell as isolated and/or enriched by the methods as described herein; exposing the hybridoma cell to an optimal culture medium for a time sufficient to allow production of IgM antibodies thereby causing production of IgM antibodies; optionally screening for IgM antibodies against the tissue-sample; optionally isolating the IgM antibodies against the tissue-sample; and optionally purifying the isolated IgM antibodies against the tissue-sample.

The immortalized cell may be of any eukaryotic cell, such as a mammalian cell, such as a human, primate, or murine cell. If the cell is a human cell, the immortalized cell can be selected, for example from a Karpas 707 cell, a B6B11 cell, thereby making a human NIMPAB cell-immortalized cell hybrid cell. In some or all aspects of the invention, the cell immortalized cell can be a mouse SP20 cell. In some or all aspects of the invention, at least one of the NIMPAB cells in the hybridoma cell line has at least one sNP inside the cell.

The tissue-sample as used in the methods of any of the embodiments or aspects herein may be from any tissue. It can be, for example, a tumor tissue, such as a solid tumor, for example, a sarcoma, carcinoma, or a lymphoma. The solid tissue may be, for example melanoma. The tumor may also be leukemia. The tissue sample may also be a blood sample or a sample taken from a normal or healthy tissue or, a malignant or inflamed tissue. The tissue may be any mammalian tissue, for example, human, primate or murine tissue.

Further provided are methods for the treatment and/or prevention of a disease comprising administering to a subject affected with the disease an IgM antibody produced by the isolated and/or enriched NIMPAB cells using the methods as described herein. The disease may be any disease wherein IgM antibodies are useful in preventing or treating a disease, for example a cancer caused by a solid tumor, such as a sarcoma, carcinoma, or a lymphoma. The solid tumor can be, for example, melanoma. The cancer can also be caused by a leukemia.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." In various embodiments, the term "about" when used in connection with percentages means ±0.10, ±0.5, or, ±1%.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It is understood that the following detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

BRIEF DESCRIPTION OF THE FIGURES

This application file contains at least one drawing executed in color. Copies of this patent application publication with color drawings will be provided by the Office upon request and payment of the necessary fee.

The following figures and drawings are illustrative of some aspects and embodiments of the invention and not to be construed as limiting.

FIG. 2A shows CD19-Cre-PZTD mice were injected with Diphtheria toxin (DT) to deplete L2pB1 cells. An almost complete loss of PD-L2+ B-1 B cells (PD-L2+TdTomato+) was shown. FIG. 2B shows B16F10 melanoma cells were cultured alone for 3 days. FIG. 2C shows B16F10 melanoma cells were co-cultured with wild type peritoneal cells. Most B16F10 cells were dying by day 3. FIG. 2D shows B16F10 melanoma cells were co-cultured with total spleen cells. No inhibition was seen. FIG. 2E shows B16F10 melanoma cells were co-cultured with L2pB1 cell-depleted peritoneal cells. B16F10 melanoma cell inhibition and cell death were significantly diminished.

FIGS. 3A and 3B show bright field, FIGS. 3C and 3D show oil red O staining and fluorescent image, and FIGS. 3E and 3F show oil red O combined with hematoxylin staining. Oil red O staining indicates accumulated lipids in dying cancer cells.

FIG. 4A shows representative FACS analysis showing PD-L2+ ZsGreen+ L2pB1 cells in tumor, draining lymph nodes and spleen. FIG. 4B shows the percentage of L2pB1 cells in total B cells is plotted. Significantly more L2pB1 cells are present inside tumor (TIL) than in draining lymph nodes (LN) or spleen (SP).

FIG. 5 shows 3D tumor spheroid growth in the presence of PCW cells from PBS-injected and DT-injected CD19-Cre-PZTD mice, in comparison with untreated control and splenocytes. On day 0, 104 B16F10 melanoma cells were seeded and on day 4, uniform 3D tumor spheroids were formed. Wild type PCW (PCW-PBS), L2pB1-depleted PCW (PCW_DT) and wild type splenocytes (Spleen) were added to the spheroids respectively. L2pB1-depleted PCW (PCW-DT) were obtained from transgenic mice expressing Diphtheria toxin receptor in L2pB1 cells, and thus depleted upon injection with Diphtheria toxin (DT). PCW-PBS and splenocytes were obtained from the same transgenic mice that received PBS injection. Tumor spheroid size was measured using CELLIGO image cytometer on day 4, 6, 8, 10 and 12. Average area of at least 6 wells of tumor spheroids were plotted over each time point. P values between each two groups were shown for day 10 and day 12.

In FIG. 6A, CD19-Cre-PZTD transgenic mice received i.p. injection of PBS or diphtheria toxin (DT) for 4 days to deplete L2pB1 cells before they were inoculated with B16F10 melanoma cells. B16F10-Luc-R melanoma cell line that expresses luciferase was inoculated. Luciferine were injected i.p. on day 20 to obtain bioluminescent signal from Luciferase-expressing tumor cells. Mice were then sacrificed and tumors were dissected (FIG. 6A). FIG. 6B shows the tumor size by IVIS of the total bioluminescent signal in the PBS group and DT group. *P=0.0569. FIG. 6C shows representative images of melanoma tumor size of PBS group abd DT treated group. FIG. 6D shows the weight of the tumor size. Average of 70% reduction of L2pB1 cells in DT-injected mice was seen at end point compare to PBS-injected mice. DT-injected mice show significant increase of tumor size and weight (P<0.05). Female mice showed similar result (data not shown). Depletion of L2pB1 cells was evaluated by fluorescent activated cell sorting (FACS) analysis of the peritoneal cavity washout cells.

FIG. 7A shows a robust inhibition of tumor growth by the control PCW condition (CP) when compared to the Non-Treated condition (NT), and a much less substantial inhibition by the L2pB1 cell Depleted PCW (DP). Both splenocyte treatments (CS & DS) result in growth rates indistinguishable from the Non-Treated condition (NT). In FIG. 7B, the conditions included in a) are also carried out with the inclusion of LPS co-stimulation, denoted by the "L". In these treatments, an even more pronounced tumor inhibition from the control PCW (CPL) when compared to the Non-treated condition (NTL). Spheroids from all other treatment conditions do not significantly deviate in size from the unstimulated groups. FIG. 7C shows the growth of each non-stimulated treatment condition (n=6 per condition) as measured via volumetric estimate derived from the image cytometry measurement of CSA and minor axis measurement. These results demonstrate a significant inhibition of the growth of MC38 spheroids when treated with syngeneic (control) PCW cells in comparison to the Non-Treated condition (P<0.0001) and to the DT PCW condition (P<0.05). Depletion of L2pB1 cells diminishes the anti-tumor effects, and the DT PCW treated spheroids show a reduced inhibition of tumor growth. Neither Splenocyte treatment causes a significant divergence in spheroid growth when compared to the Non-Treated control. FIG. 7D shows the results generated in the non-stimulated treatments are further compounded in the LPS stimulated conditions. L2pB1 cells in the Control PCW are further stimulated by LPS, and this enhances their anti-tumor response resulting in a more robust reduction in tumor size when compared to the Non-Treated+LPS condition (P<0.0001) and the DT PCW+LPS condition (P<0.001).

FIG. 9A is an illustration of sNP structure. When suspended in media, the sNps have an average diameter of 226 nm in this experiment. The SPIONs inside the nanoparticle are approximately 13~15 nm. The pHrodo-red and PtC on the outside of the nanoparticle will only display as red when in an acidic environment, such as lysosome inside a phagocyte. FIG. 9B shows mouse peritoneal washout cells after macrophage plate adhesion depletion (left). Mouse peritoneal washout cells after macrophage plate adhesion depletion followed by overnight incubation with PHRODO-red. Bright dots indicate phagocytosed sNP in ZsGreen-expressing mouse NIMPAB cells. FIG. 9C shows FACS analysis of mouse peritoneal washout cells before and after sNP incubation and magnetic pulldown. FIG. 9D is a graphic analysis of percentage change of cell population before and after sNP magnetic pulldown. T cells, B2 B cells and other cells have reduced percentage after magnetic pulldown. Only B-1 cells and IgM+CD19+B-1 cells have increased percentage.

FIG. 10A is a flow chart of fusion between isolated NIMPAB cells and human myeloma partner cell line. FIG. 10B shows a pilot fusion experiment using a model human IgM-secreting cell and myeloma partner cell line. After the fusion, cells went through an Ouabian-HAT double selection for 2~4 weeks. Microscopic image shows that inappropriately fused cells die in the double selection media. By 3 weeks, monoclones start to show in the tissue culture plate (Day 21 column).

FIGS. 14A-14C shows schematic diagrams of Route 2, 3 bilayer PtC-lipid coated nanoparticle with aqueous-SPIONs core. FIG. 14A shows the nanoparticle structure for Route 2 and 3. FIG. 14B shows the SPION structure in Route 2. FIG. 14C shows the SPION structure in Route 3.

FIGS. 15A-15B shows schematic diagrams of Route 4 bilayer PtC-lipid coated nanoparticle with aqueous-SPIONs core. FIG. 15A shows nanoparticle structure for Route 4. FIG. 15B shows a SPION structure in Route 4.

FIG. 17A shows NBD (green fluorescence dye) is embedded in liposomes as pH-insensitive reference fluorescence. PHRODO-dye on the surface of the liposomes were used as indicator of pH reduction in the event of phagolysosome formation. Double positive signals of red (PHRODO) and green (NBD) indicate phagocytosis of the liposomes (red arrow) while single positive signal of green (NBD) without red signify surface attachment of the liposomes. Peritoneal cells were incubated with either PtC-liposomes or control liposomes for 2 hours at 37° C. FACS analysis of both PHRODO red and NBD green signals in B-1 cells (CD19+, IgM+, CD5+, CD11b-mid) is shown as indicator of acidic phagolysosome formation. FIG. 17B shows PD-L2 expression of B-1 cells and phagocytosis of PtC-liposome is analyzed. All PtC-liposome-containing cells are PD-L2 positive (red arrow) whereas none of the PD-L2 negative B1 cells contains PtC-liposome. Immunofluorescent microscopic images were also taken of PtC-liposome phagocytosis. Stained cells were resuspended in LIVE CELL IMAGING SOLUTION with a neutral pH of 7 to decrease the background fluorescence of PHRODO™-dye (data not shown).

DETAILED DESCRIPTION OF THE INVENTION

Figure 1A:
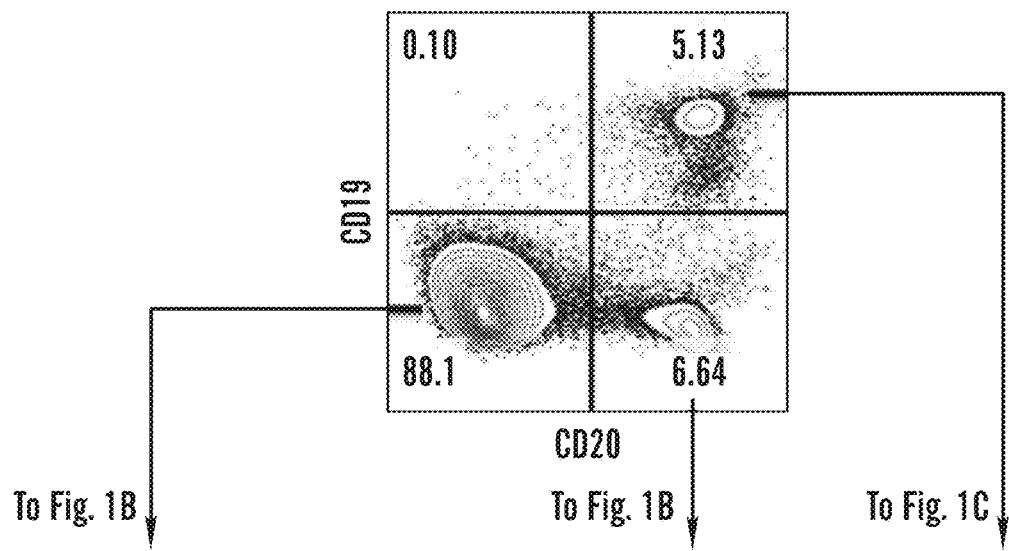
FIGS. 1A-1C show human phagocytic B cells in peripheral blood. Peripheral PBMC was obtained from healthy donor and incubated over night with PtC-nanoparticle and control nanoparticles at 1:20 ratio. Cells were then stained for CD19, CD20 (FIG. 1A) and CD5 and CD14 (FIG. 1B). In this individual, 15% of human CD19+CD20+ B cells specifically phagocytose PtC-nanoparticles (arrow), whereas CD14+ monocytes phagocytose both PtC-nanoparitcles and control nanoparticles (FIG. 1C). Results are representative of four experiments.

Antibody-based therapies continue to provide novel disease treatments. For example, antibody-based immunotherapy continues to grow as the leading edge and future key market of cancer therapy. However, current approaches typically utilize monoclonal antibodies that are based on humanized IgG antibodies produced in an animal against a specific antigen or a specific biomarker protein of an immune cell regulatory pathway. For example, in cancer therapy, antibodies that target either a single "tumor antigen" or a single "check point" biomarker of an immune cell regulatory signaling pathway. The success from such approaches has been counterbalanced and limited by adverse side effects due to the inevitable inflammatory cascades caused by the IgG-antibody-induced immune reaction and, particularly in the treatment on cancer, the drug resistance caused by tumor heterogeneity, new mutations or signaling bypass.

The inventors have proposed using IgM antibodies to overcome the adverse immune reactions, as IgM antibodies do not initiate these reactions, and as a way to allow antibodies that target a disease process, such as cancer, specifically, but are not limited to a single antigen, and to simplify the process and avoid side effects caused by humanized albeit still foreign-species-produced antibodies.

However, cells that produce IgM antibodies are exceedingly rare in tissues. Thus "making" IgM antibodies was thought to be a significant problem for any practical use of these antibodies. The amount of IgM antibodies in subjects is also not high, so isolating them from the subjects was also not thought to be a viable option for large scale use of these antibodies. Moreover, due to the rarity of the cells, it was also not thought that finding therapeutic antibodies would be possible for clinically useful purposes.

The inventors have been working on solving these problems and now provide a surprising solution as to how to isolate and enrich the natural IgM producing cells from a subject in a clinically useful scale.

Moreover, the inventors describe how to make a hybridoma cell or cell line that produces the natural IgM antibodies produced by the isolated NIMPAB cells.

The inventors also provide a system or method for screening for therapeutically or prophylactically useful IgM antibodies using the isolated and enriched cells or the hybrid cells.

The inventors believe that the methods allow, for the first time, making IgM antibodies a viable therapeutic as well as preventive tool for treating and preventing diseases, such as cancer.

As summarized above, the methods disclosed herein relate to making naturally existing anti-tumor immunoglobulin M (nIgM) antibodies. These 'immune surveillance' immunoglobulins are poly-reactive IgM antibodies that recognize cancer cells in primary and recurring tumors rather than a single fixed antigen. The nIgM antibodies are also regulatory through an antibody network and other mechanisms to keep inflammation in check. These features are important, for example, in overcoming the evolutionary tendencies of cancer cells and for limiting adverse side effects caused by the inflammatory response, both of which are a problem in most therapeutic humanized monoclonal IgG antibodies on the market.

The IgM antibodies are produced in everyone, both healthy individuals and patients affected with various diseases, by a specific type of B lymphocyte that are rare in peripheral blood. The inventors have now developed a nanoparticle-based method to rapidly identify, isolate, and enrich these B cells from peripheral blood or any biological sample comprising dissociated cells. These B cells can be immortalized by hybridoma fusion technology to become IgM production "factories", in other words, cell lines that can be used to produce the IgM antibody/antibodies produced by any one of the isolated NIMPAB cells. The inventors have also developed an innovative screening process to identify therapeutically useful IgM antibodies. Together, the described methods and compositions allow mass production of these disease-specific nIgM for therapeutic and for prophylactic use.

In particular, the technology described herein relates to the (i) development of modified superparamagnetic iron oxide nanoparticle (SPION) comprising particles that is being taken up by phagocytosis natural IgM-producing phagocytic B cells (NIMPAB) when a dissociated cell-mixture comprising them is exposed to the particles, (ii) optimization of human hybridoma technology that is specific for the immortalization of human NIMPAB cells that surprisingly remain capable of making IgG antibodies even when they comprise the particles inside the isolated cell, and (iii) developing standard screening methods specific for the verification of anti-disease, such as anti-cancer, function of the natural IgM antibodies produced by the NIMPAB-hybridoma cells.

Accordingly, the technology described herein relates in part, to compositions comprising the NIMPAB cells and the specific particles comprising SPIONs, to methods of isolating and enriching the NIMPAB cells, to methods of making NIMPAB hybridoma cells, to methods of making IgM antibodies using the NIMPAB hybridoma cells, to methods for screening for useful IgM antibodies produced by the NIMPAB hybridomas and use of the such-produced IgM antibodies for the treatment of human diseases. The NIMPAB-hybridoma cell clones produced by the methods described herein can be used to create a library of IgM-producing clones allowing a tool to screen for IgM antibodies against any target. Thus, the invention also provides a library of different disease-specific IgM antibodies comprising a collection of hybridoma cells made of the isolated NIMPAB cells.

For example, the central question of cancer therapy is to identify reagents or antibodies that specifically target tumor cells but not normal cells. All tumor antigens are essentially self-antigen that is expressed in the wrong cell type, in abnormal amount or in the wrong timing etc. (with the exception of tumors that are induced by viral infection, in which case viral antigen can serve as foreign tumor antigen). Thus it is very hard to generate a totally tumor-specific reagent. The technology as disclosed herein solves this problem by looking into our body for the best solution. Different from traditional generation of anti-tumor antibodies, which involves identifying tumor antigen first followed by immunization of animals, our approach is totally natural. Herein, the inventors have demonstrated that the true cancer-recognizing antibodies are natural IgMs that exist in healthy individuals. These antibodies protect most healthy individuals from the accumulation of cancerous cells. However, traditional method is laborious to identify the B cells that secret these naturally existing antibodies. It often took screening thousands of human B cell hybridomas to obtain a few clones. The technology described herein will significantly increase the efficiency of identification and isolation of naturally-existing cancer-specific B cells.

The technology described herein is based upon, at least in part, pre-clinical data using a syngeneic animal tumor model, and has demonstrated that natural IgM-producing phagocytic B cells (NIMPAB) are essential components of the immune-surveillance system that recognize, inhibit, kill and phagocytose, e.g., cancer cells. The inventors have also identified, isolated and enriched NIMPAB cells in human peripheral blood. Others have also reported that human natural IgM antibodies generated by these special B cells are the only antibodies that can truly distinguish, for example, cancer cells from normal cells. Therefore, without wishing to be bound by a theory, the inventors submit that any tissue that can be dissociated so that cells are accessible, can serve as a starting material to find NIMPAB cells.

While the specific pre-clinical examples described herein relate to the prevention and treatment of cancer, the IgM antibodies produced by the methods of the invention can be used as therapeutic antibodies against other diseases, where antibody therapies have been discovered as useful interventions, such as autoimmune diseases.

Figure 1B:
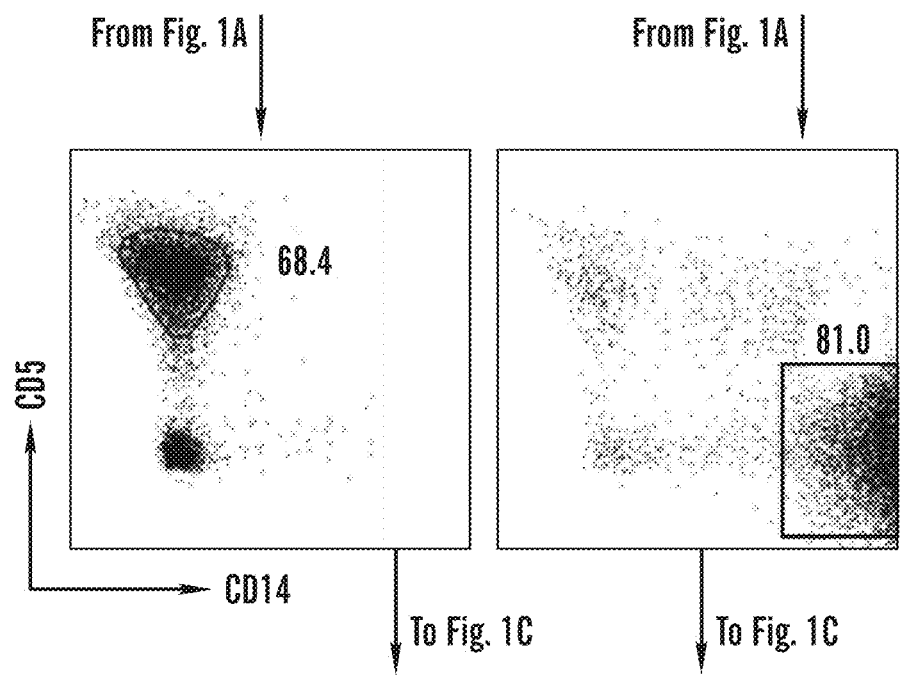
Figure 1C:
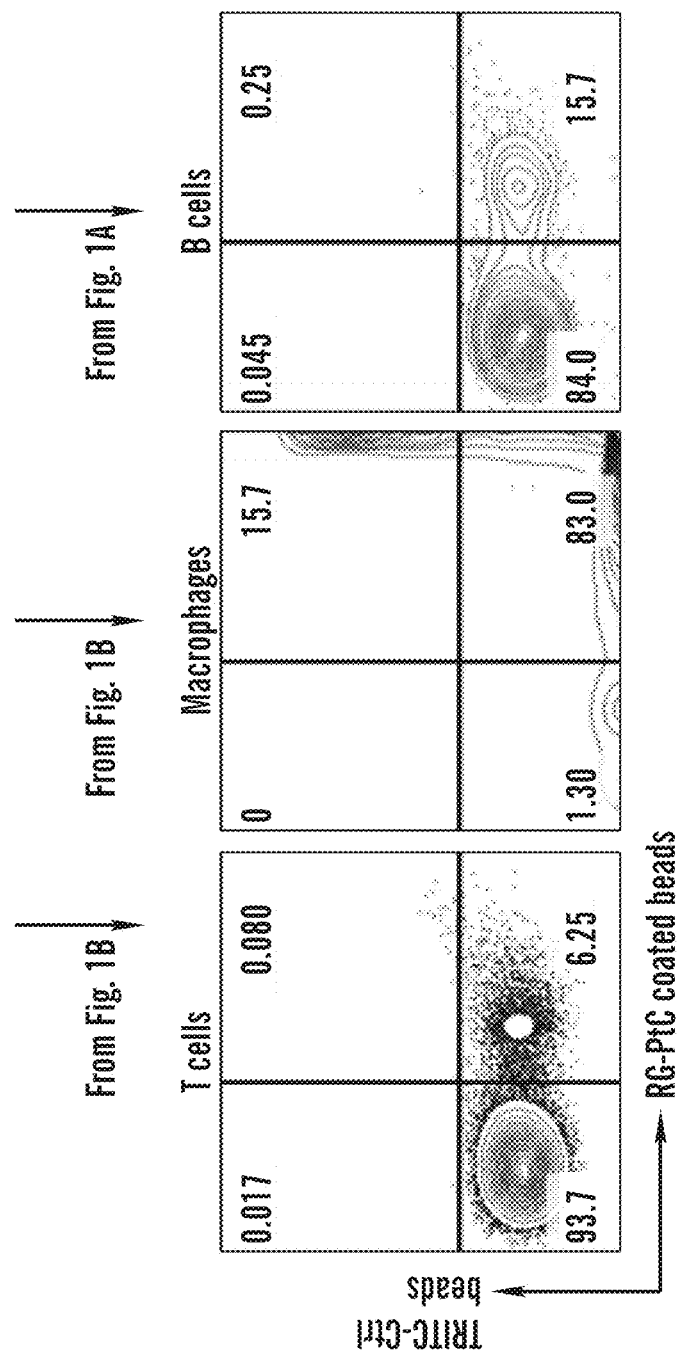
Figure 2A:
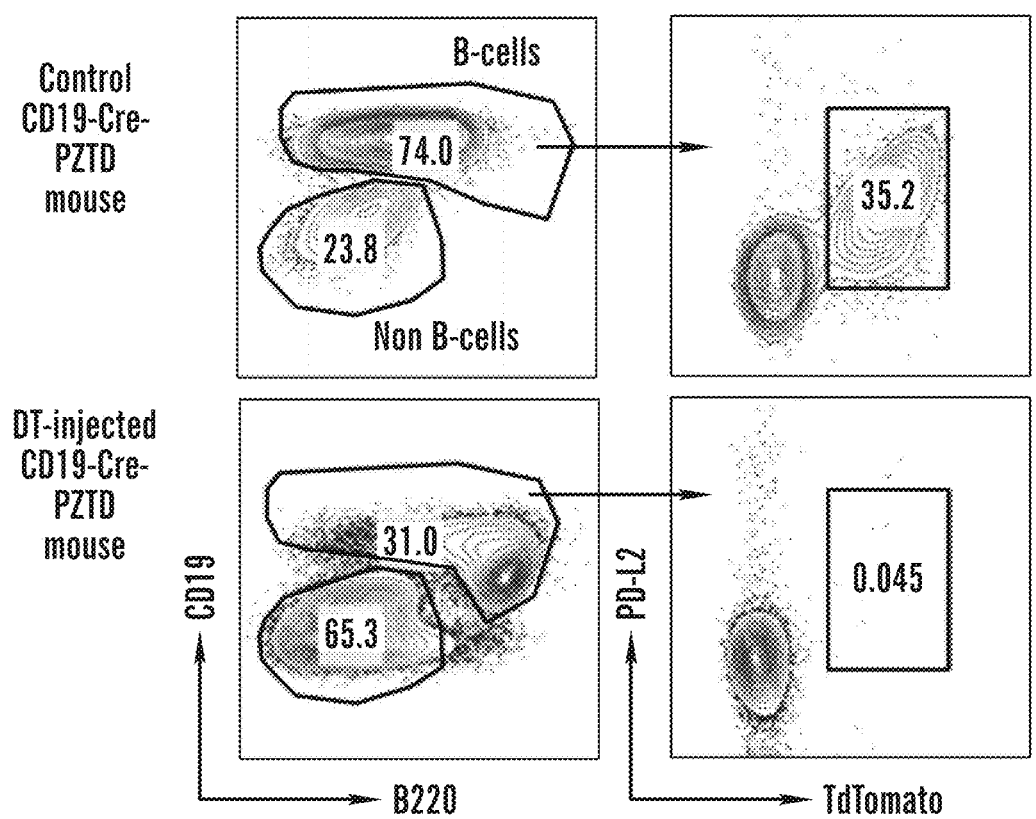
FIGS. 2A-2E show L2pB1 cells are required for inhibiting B16F10 melanoma cells.
Figure 2B:
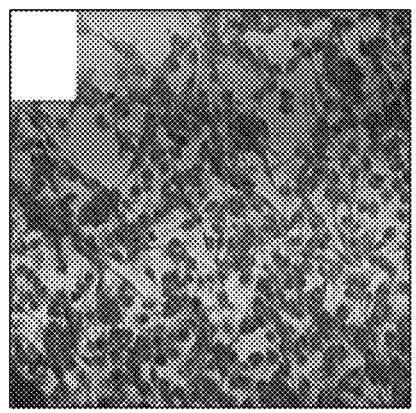
Figure 2C:
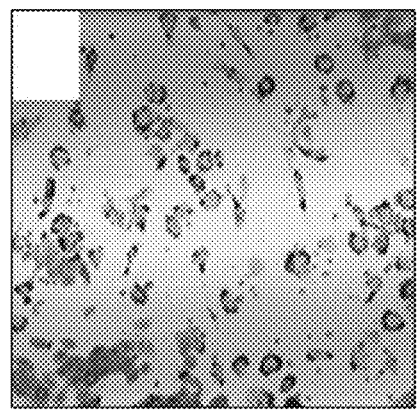
Figure 2D:
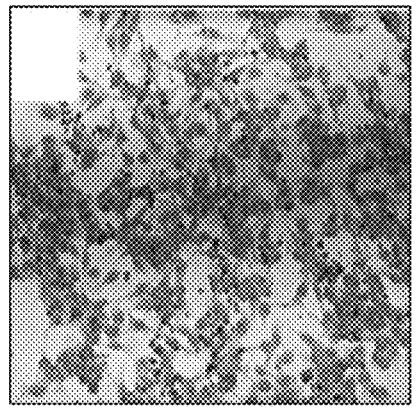
Figure 2E:
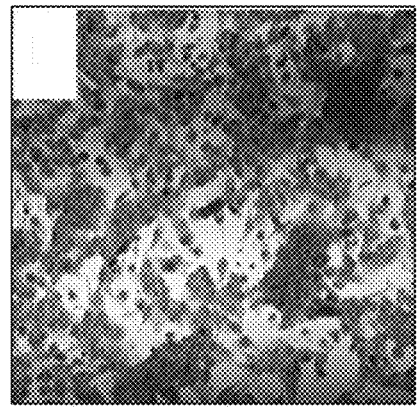
Figure 3A:
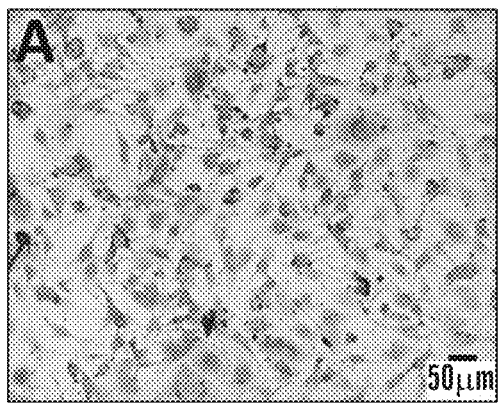
FIGS. 3A-3F shows mouse peritoneal cells induce lipoptosis of melanoma cells. B16F10 melanoma cells were incubated alone (FIGS. 3A, 3C, 3E) or with peritoneal cells (FIGS. 3B, 3E, 3F). Peritoneal cells contained more than 50% of B-1 cells.
Figure 3B:
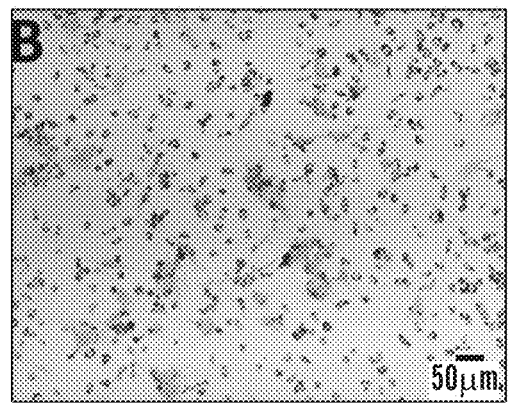
Figure 3C:
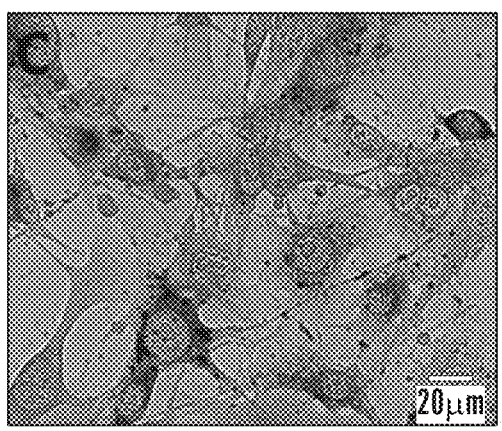
Figure 3D:
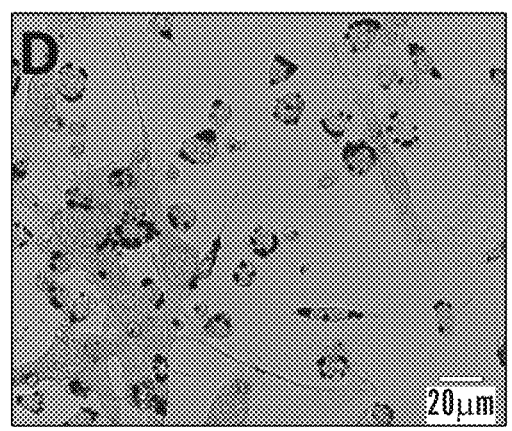
Figure 3E:
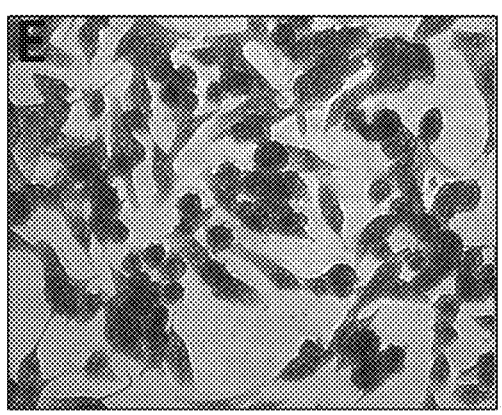
Figure 3F:
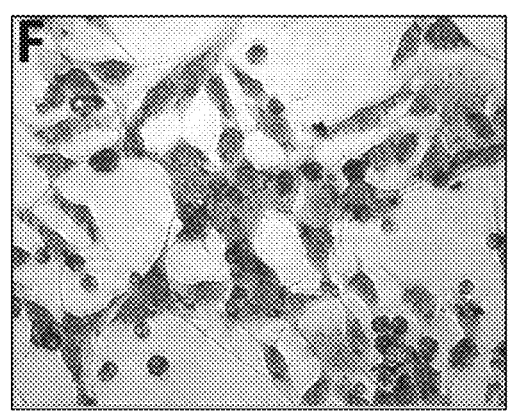
Figure 4A:
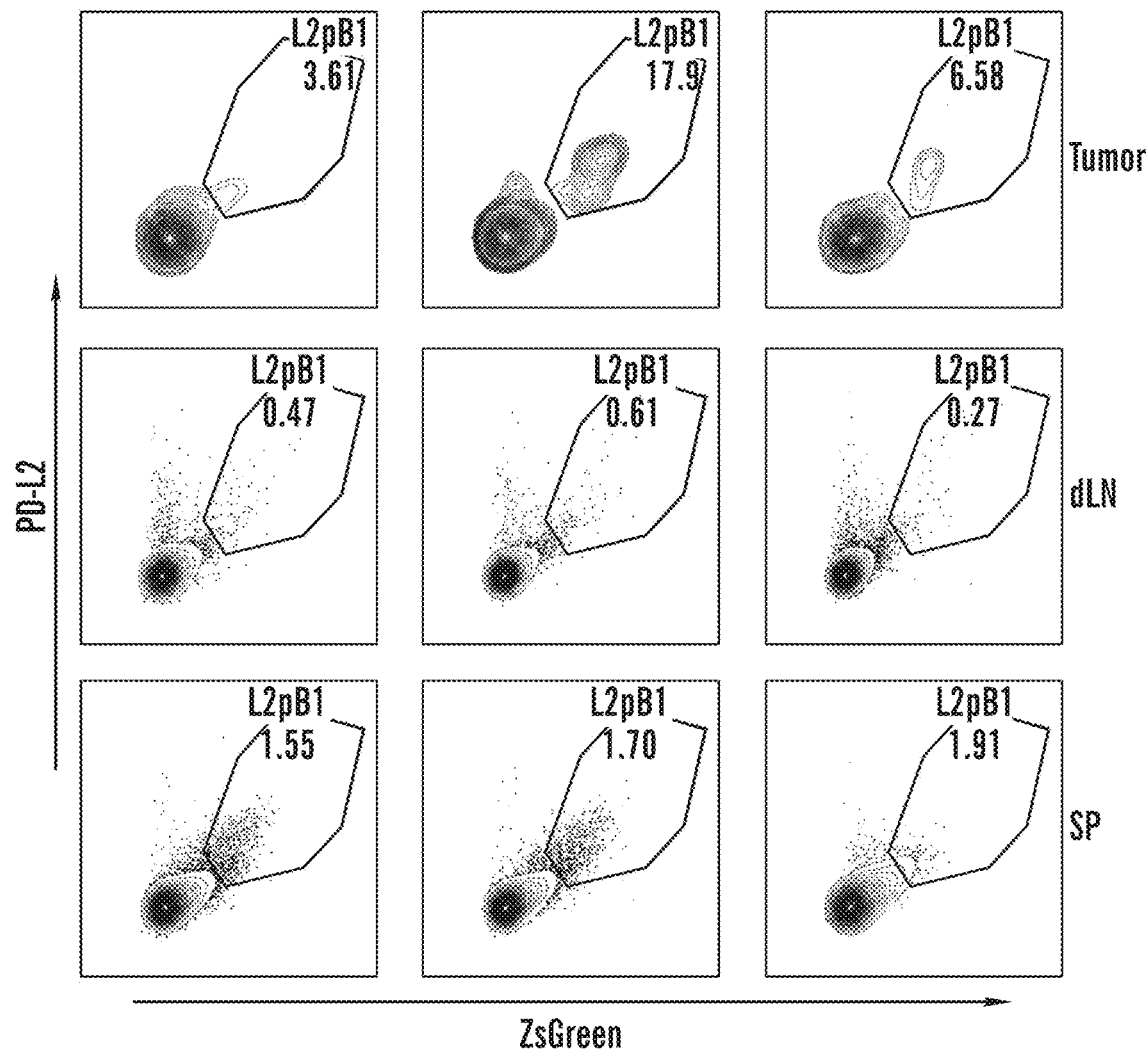
FIGS. 4A-4B shows active accumulation of L2pB1 cells inside tumor PZTD mice were injected with 0.5 million B16F10 melanoma cells. Tumors were dissected on day 18 post injection. Tumor infiltrating lymphocytes (TIL) were obtained by proteolytic dissociation of the tumor cells to obtain a single cell suspension by gentle collagenase digestion. The lymphocytes were then further separated from tumor and dead cells by PERCOLL gradient purification, following standard protocols. Lymphocytes were subjected to immunophenotyping by FACS staining with fluorescently-labeled antibody specific for CD45, CD3e, CD19, B220, IgM, PD-L2. Transgenic mice also express ZSGREEN in L2pB1 cells.
Figure 4B:
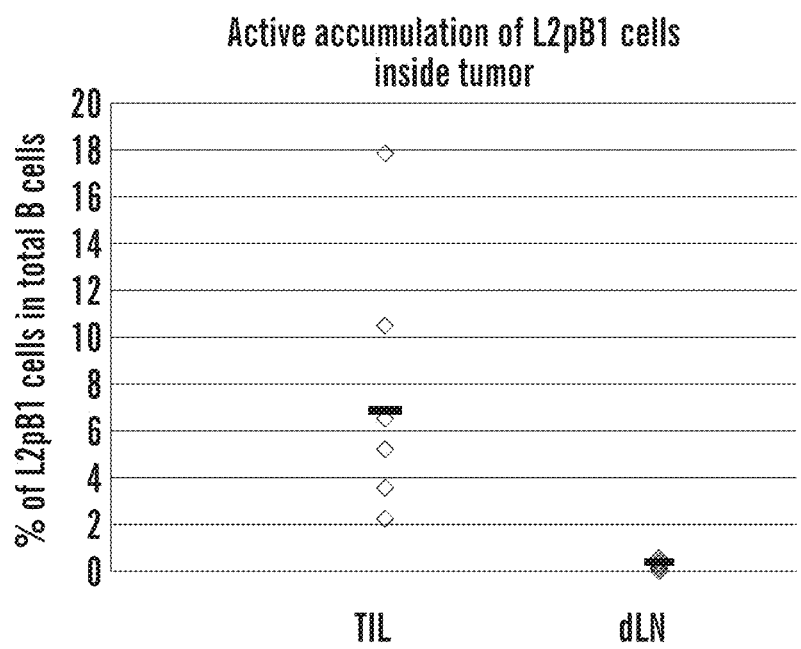
Figure 5:
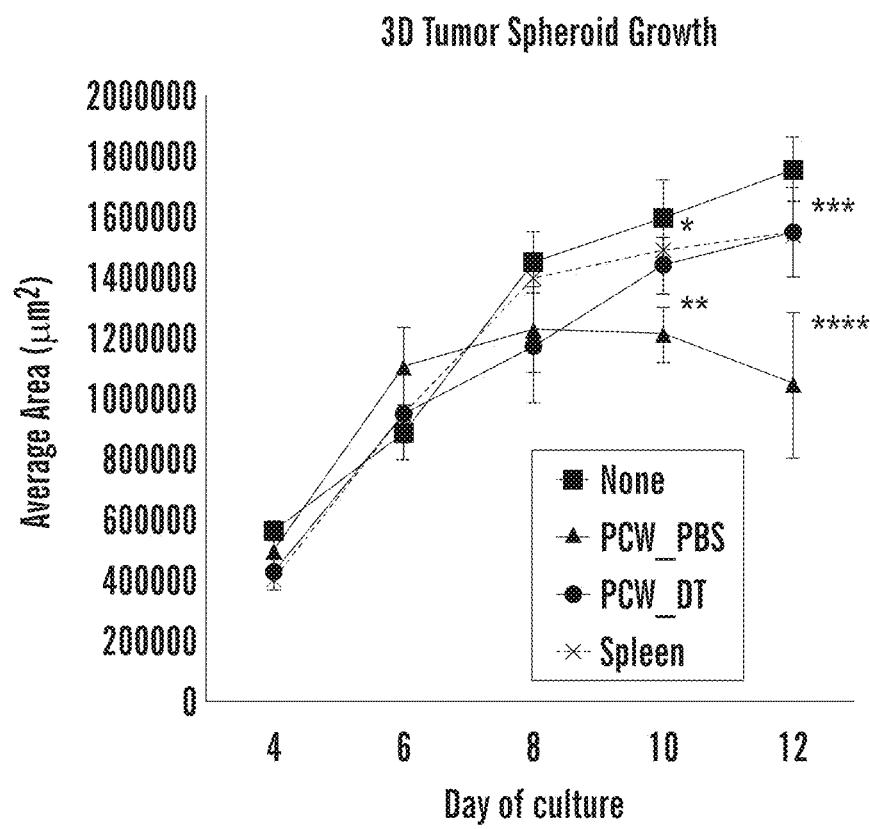
FIG. 5 shows that depletion of L2pB1 cells diminishes the growth inhibition effect of PCW on tumor spheroids. B16F10 melanoma cells were cultured in Corning spheroid ultra-low attachment microplate to form 3D spheroids. Calcein AM (green florescent staining) and PI (red florescent staining) staining were used to evaluate tumor spheroids formation with the increase of PI staining positive necrotic core, which starts to appear on day 4. Calcein AM positive live cells were observed as a typical green ring around the spheroid surrounding the red necrotic core.
Figure 6B:
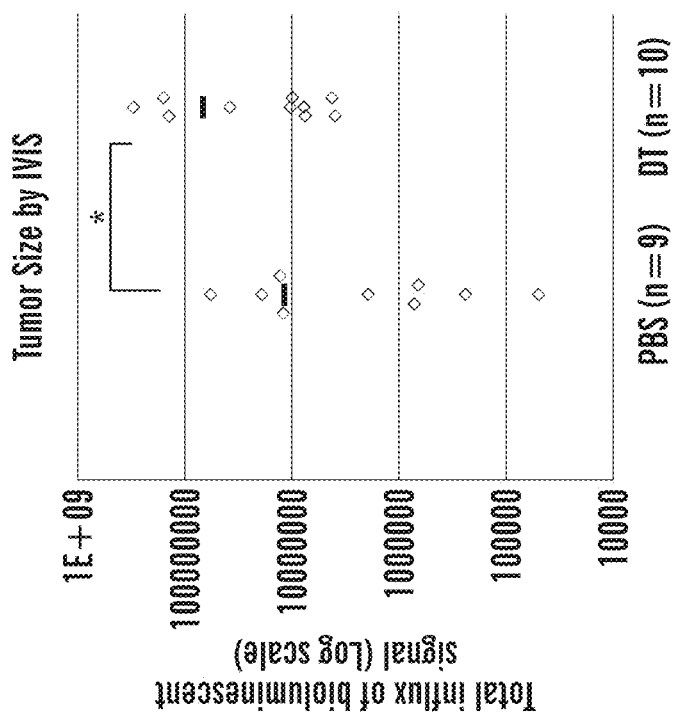
FIGS. 6A-6D show depletion of L2pB1 cells (mouse NIMPAB cells) in vivo increases melanoma tumor mass. CD19-Cre-PZTD transgenic male mice received intra-peritoneal (i.p.) injection of PBS or diphtheria toxin (DT) for 4 days before they were inoculated with $10^6$ B16F10 melanoma cells. Mice were sacrificed 10-14 days post inoculation. Tumors were imaged and dissected for weight measurement.
Figure 6A:
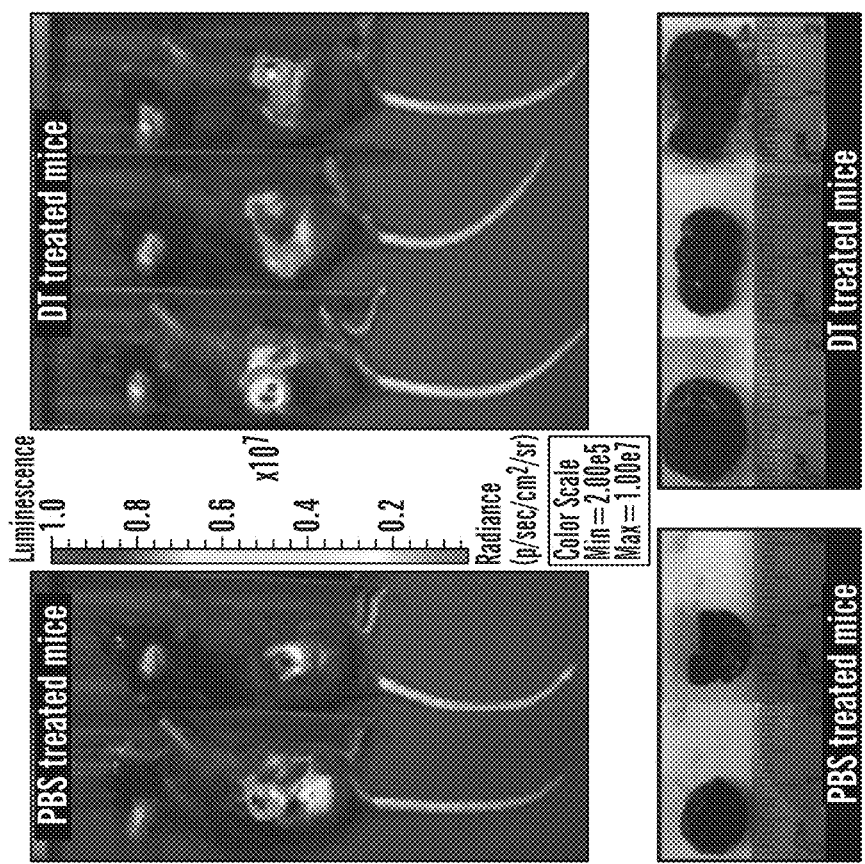
Figure 6D:
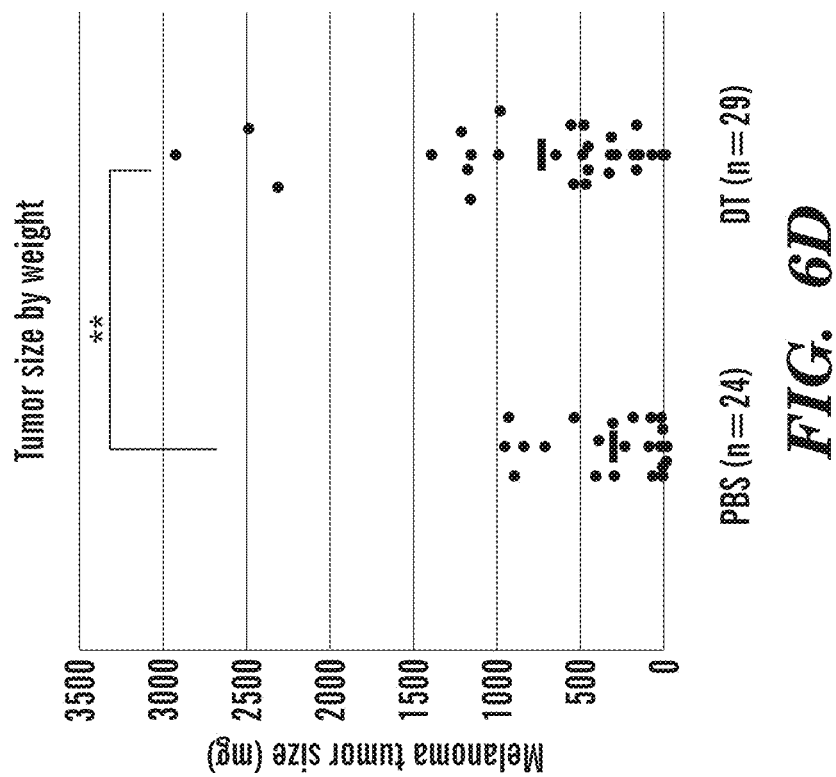
Figure 6C:
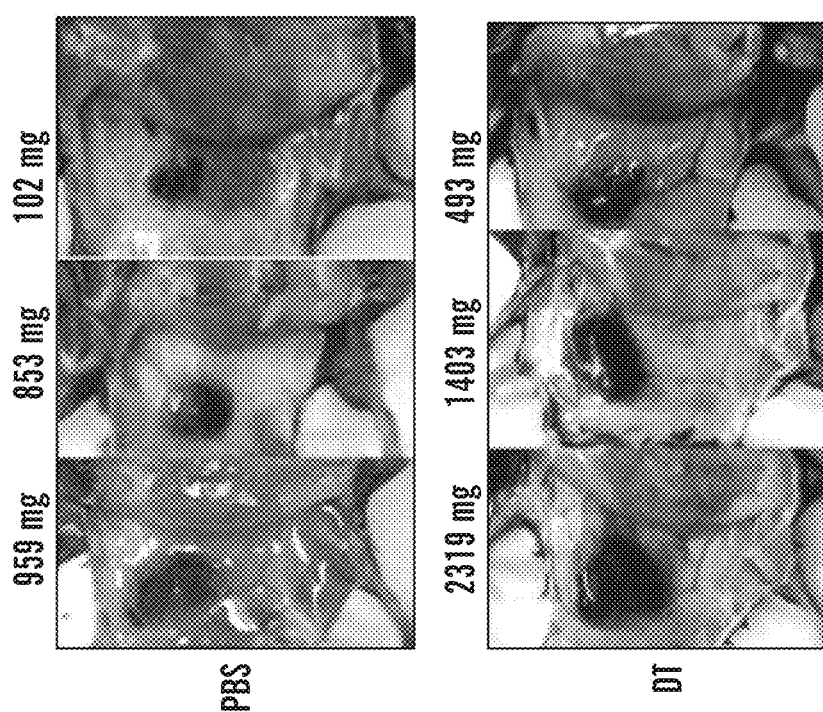
Figure 7A:
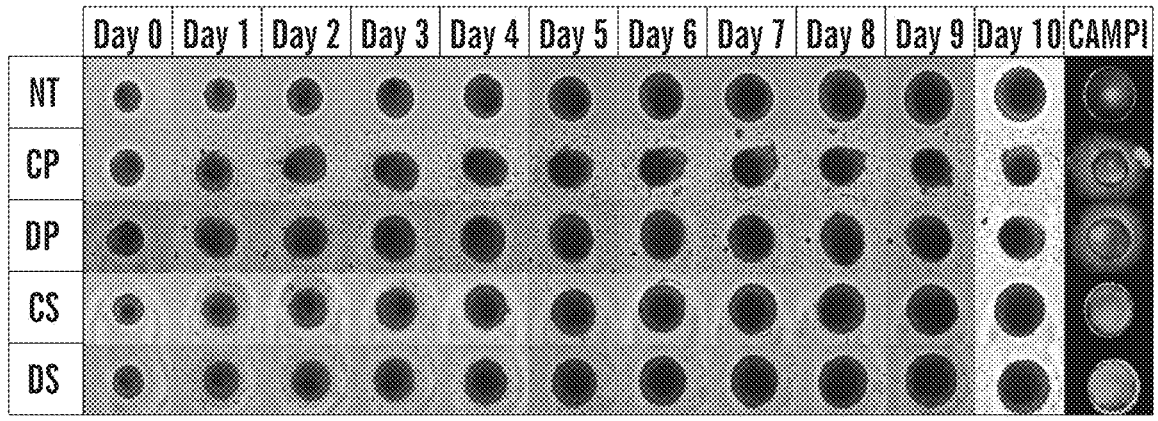
FIGS. 7A-7D show depletion of L2pB1 cells attenuated the inhibition of MC38 spheroid The MC38 mouse colon cancer cell spheroids were treated with the various naive or unstimulated immune cell treatments for ten days.
Figure 7B:
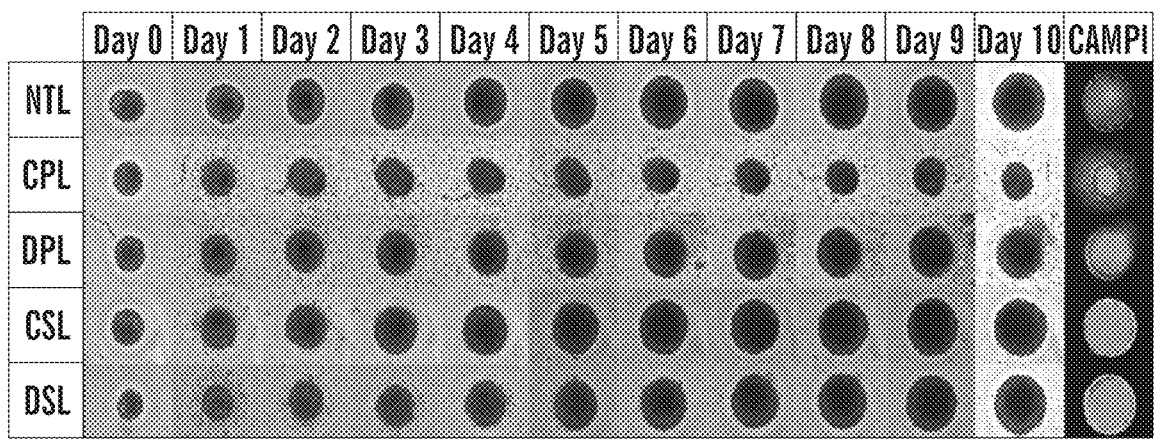
Figure 7C:
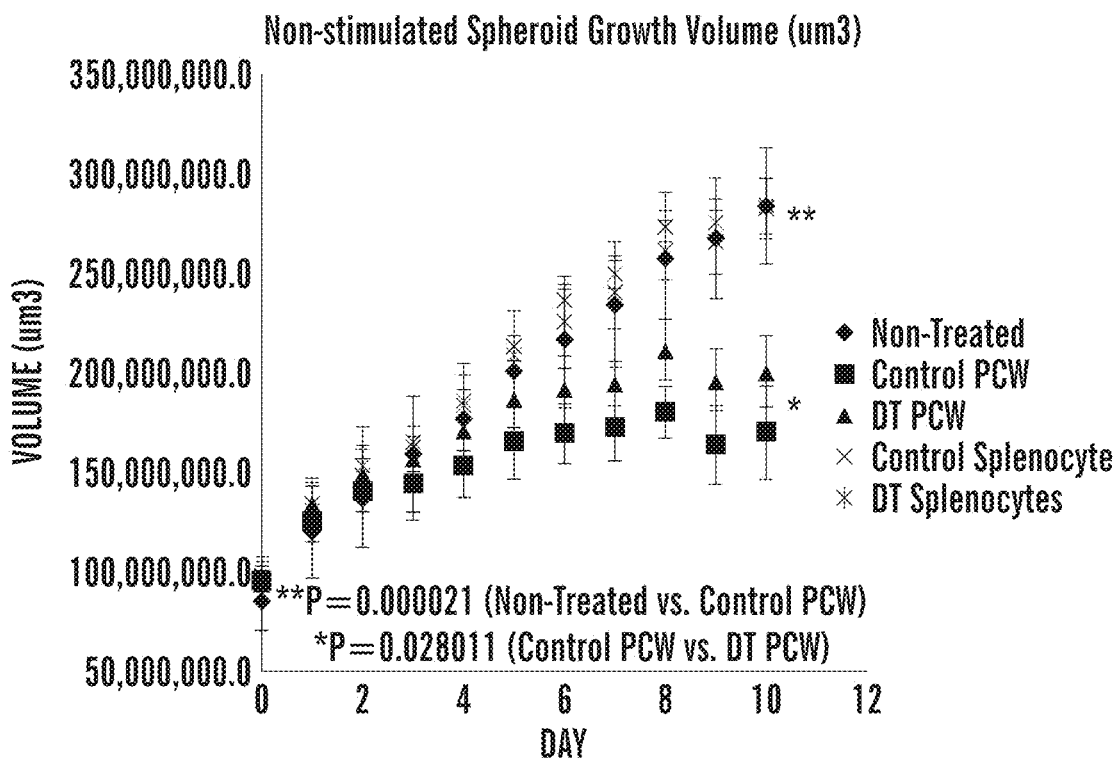
Figure 7D:
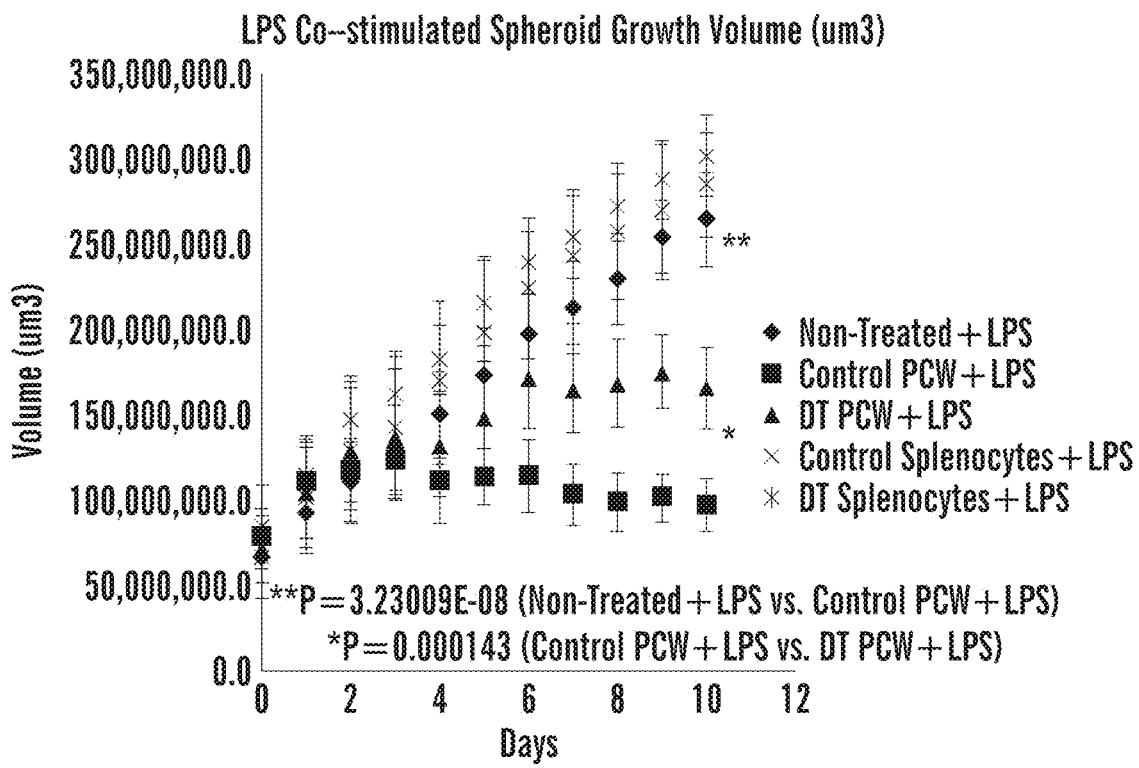

The inventors have demonstrated using a pre-clinical proof-of-concept-study using a murine animal model that depletion of murine NIMPAB cells (L2pB1 cells) resulted in larger tumor size, weight as well as increased angiogenesis (see FIG. 6A-6B). The inventors also showed that murine peritoneal cavity washout cells (PCW), a major source of NIMPAB cells, can inhibit tumor growth and induce apoptosis of tumor cells. Moreover, the inventors showed that L2pB1-cell (mouse NIMPAB cell)-depleted PCW lost tumor inhibition. Additionally, using a pre-clinical study using human PBMC, the inventors have demonstrated that human NIMPAB cells can be identified by flow cytometry (FIGS. 1A-B); and human NIMPAB cells can specifically phagocytose PtC-modified nanoparticles but not control unmodified nanoparticles (FIG. 1C). Based on these studies, the inventors concluded that the NIMPAB cells are the cells that can produce specific disease-fighting IgM antibodies.

The inventors discovered NIMPAB cells both in mice and human and have isolated, analyzed and culturing murine and human lymphocytes. Thus, it is reasonable to conclude that mammals that have an immune system, including B-cells, all have cells that function like NIMPAB cells in producing IgM antibodies, and that the methods and compositions as described in the claims would apply to all such mammals. At minimum, the methods and compositions apply to humans, primates, and murine species.

Given that the NIMPAB cells are not abundant, the inventors wanted to develop a method to isolate and enrich the NIMPAB cells, and screen them to see what kind of antibodies they produce, so that their use could be scaled up to provide a reasonable therapeutic intervention. Optimally, the inventors also wanted to develop a method to clone the NIMPAB cells so that the hybrid cells could be used to produce therapeutic antibodies, in vitro, in reasonable quantities.

In working on solving these problems, the inventors developed nanoparticles that comprise iron oxide nanoparticles (also referred to herein as superparamagnetic iron oxide nanoparticles or SPIONs) and surprisingly found out, that the NIMPAB cells could take up specifically, without "ingesting" other particles, some of these particles by phagocytosis whereas other cells were not specific for the particles, providing a uniquely targeted way of "feeding" the NIMPAB cells with the specifically constructed SPION comprising particles.

Moreover, despite skepticism, the inventors were able to manufacture a particle-structure that allowed the NIMPAB cells to "ingest" or take up by phagocytosis enough particles so that one was able to attract the particle-comprising cells toward an external magnet thus allowing a method of isolating and enriching the NIMPAB cells using an external magnet. Thus, a magnet can be used to attract the cells comprising the particles to the wall of any container. The magnet and the container can be separated or "dissociated" from each other, allowing the cells to release from the wall of the container back to the container. The cells not attracted to the wall of the container can be removed by washing the container with the magnet in contact with the wall of the container or the cells not attracted to the magnet can be discarded from the container and after discarding the cells, the magnet can be dissociated from the wall of the container. The cells can be further subjected to FACS, particularly, when the particle comprises a fluorescent dye.

In some or all aspects of the compositions and methods of the invention, the particle further comprises a fluorescent dye or conjugate, such as PHRODO, or another well-known fluorescent dye.

The particles were developed to make them work specifically for NIMPAB cell phagocytosis. For example, in some aspects, SPION is dispersed in poly (lactic-co-glycolic acid) (PGLA) core and the core is coated with a lipid bilayer comprising phosphatidylcholine (PtC) and polyethyleneglycol (PEG). Example of such construct is illustrated, e.g., in FIG. 13. In some aspects, the SPION is dispersed in aqueous solution core and the core is coated with a lipid bilayer comprising phosphatidylcholine (PtC) and polyethyleneglycol (PEG), optionally wherein the aqueous solution core comprises a stabilizer, for example a stabilizer that is a catechol group modified poly (2-acrylamido-2-methyl-1-propanesulfonic acid) (pAMPS*) and the pH of the aqueous solution core is neutral. In some aspects, the SPION is coated with citric acid and the pH of the aqueous solution core is between or at about 8 and about 9. Illustrative examples of the particles are provided in FIGS. 13-15. Optionally, in some or all aspects of the methods and compositions of the invention, the particles may also comprise a fluorescent conjugate, such as PHRODO-red-lipid-conjugate.

The SPIONS are, for example, 10-20 nm in diameter, such as 12-18, for example 13-15 nm in diameter. A mixture of SPIONS with slightly varying diameter can be used or SPIONs with uniform diameter can be used.

In making the SPIONs useful in the methods of the invention, one can, for example, utilize oleic acid-coated iron oxide nanoparticles synthesized via thermal decomposition. Briefly, the following reagents are mixed and stirred magnetically under nitrogen flow: 2 mmol iron (III) tri (acetylacetonate), 10 mmol 1,2-tetradecanediol, 6 mmol oleic acid, 6 mmol oleylamine, and 80 mL benzyl ether. The resulting nanoparticles are precipitated in excess ethanol and pulled down using a magnet. The precipitated particles are washed with ethanol, dissolved in 15-20 mL hexane and centrifuged to remove aggregates. The SPIONs, which at this point are oleic acid-coated, are dried in a vacuum oven for at least 2 hours.

In making the hybrid lipid-polymer nanoparticle synthesis hybrid lipid-polymer nanoparticles with encapsulated SPIONs can be synthesized via, for example, emulsion. Briefly, poly (lactic-co-glycolic acid) (PLGA) is combined with 1,2-Distearoyl-sn-glycero-3-phosphoethanolamine-poly (ethylene glycol) (DSPE-PEG) and lecithin such that the mass of the PLGA is 5× the lipid shell mass. The molar ratio of lecithin:PEGDSPE is 7:3. Both lipid compounds are dissolved in a 4% ethanol solution and heated to the lipid transition temperature. Additional water may be added to the hydrophilic phase, depending on the desired size of the hybrid nanoparticles. PLGA, along with oleic-acid coated SPIONs, are dissolved in 4:1 acetonitrile:chloroform. The hydrophobic phase containing the PLGA and SPIONs is added to the hydrophilic phase containing both lipids, and the resulting mixture is sonicated. The solvents are removed via rotary evaporation, and the resulting nanoparticles are washed 3× with DI water.

The size of the nanoparticle is analyzed, for example, by dynamic light scattering. The magnetic properties are evaluated by placing a magnet and verifying that the polymer-coated nanoparticles can be attracted to the magnet. Interaction between lipid-polymer-coated nanoparticles of iron oxide and immune cells is utilized in the separation methods of the invention.

The total nanoparticle size suitable for NIMPAB cell uptake is about 200-600 nm.

The particles can be evaluated for uptake by the cells by incubating them with the cells for about 3-24 hours, such as 3-6, 3-8, 3-10, 3-12 hours. A weak magnet can be used to separate out the cells that have taken up the particles from cells that have not taken up the particles.

In some or all aspects of the methods and compositions of the invention, the particles can be made, for example using iron tri(acetylacetonate) (2 mmol), 1,2-tetradecanediol (10 mmol), oleic acid (6 mmol), oleylamine (6 mmol), dibenzyl ether, citric acid, diethyl ether, 2-methoxyethylamine, N-(3-Dimethylaminopropyl)-N'-ethylcarbodiimide hydrochloride (EDC), N-Hydroxysuccinimide (NHS), poly(D,L-lactide-co-glycolide), thioglycolic acid, hydroxylamine, chloroform, and phenanthroline were all purchased from Sigma-Aldrich (St. Louis, Mo.). 1,2-dichlorobenzene and N,N'-dimethylformamide were from Acros Organics (Morris Plains, N.J.). L-α-Phosphatidylcholine (Egg, Chicken) and 1,2-Dipalmitoyl-sn-Glycero-3-Phosphate were obtained from Avanti Polar Lipids (Alabaster, Ala.). NH2-PEG (550 Da, 2000 Da, 5000 Da, and 10000 Da) were all obtained from Laysan Bio, Inc. (Arab, Ala.). DSPE-PEG-NH-2, MW 2000 was purchased from Nanocs, Inc. (New York, N.Y.). Ethyl Alcohol 200 Proof was purchased from Pharmco-Aaper (Brookfield, Conn.). Slide-A-Lyzer G2 dialysis cassettes, chambered slides, bovine calf serum (BCS), dimethyl sulfoxide, PHRODO™ Red, succinimidyl ester, GE Healthcare filter devices, and centrifugal filter units were acquired from Thermo Scientific (Rockford, Ill.). Borate buffer was obtained from Boston Bio Products (Boston, Mass.). Suitable ingredients can be naturally purchased also from other manufacturers than those named above.

The Superparamagnetic Iron Oxide (Fe-3O4) Nanoparticle (SPION) Synthesis can be performed, for example by a method described by Sun et al. and further modified following a method described by Lattuada et al. (Lattuada M, Hatton T A. Functionalization of monodisperse magnetic nanoparticles. Langmuir. 2007; 23:2158-2168, incorporated herein by reference in its entirety for teaching an exemplary method for making the SPION particles useful in the compositions and methods of the invention). Briefly, iron (III) tri(acetylacetonate) [Fe(acac)3] (2 mmol), benzyl ether (40 mL), 1,2-tetradecanediol (10 mmol), oleic acid (6 mmol), and oleylamine (6 mmol) were mixed and stirred magnetically under a flow of nitrogen. The mixture was heated at 2 degrees per min to 100° C. and kept for about 45 min, followed by heating to 200° C. at 2 degrees per min and kept for 2 h. Subsequently the reaction mixture was heated to reflux (~300° C.) and held for another about 30 min to about 1 h. The oleic acid-coated SPIONs were stored after washing steps with an excess of ethanol and after a drying step in a vacuum oven. For hydrophilic water-soluble SPIONs, oleic acid-coated nanoparticles were dissolved in a dichlorobenzene and dimethylformamide mixture (1:1 v/v) with citric acid and heated to 100° C. for about 24 h. Finally, the citric acid-coated SPIONs were further functionalized with amine-terminated polyethylene glycol (PEG) of varying chain lengths (550, 2000, 5000, and 10000 Da) or 2-methoxyethylamine (2-MEA) using N-hydroxysuccinimide (NHS) ester and 1-ethyl-3-(3-dimethylaminopropyl) carbodiimide (EDC) in pH 9 for 24 h on an agitator at room temperature. The PEG Fe NPs were obtained after they were dialyzed for 48 h against deionized water at pH 9. Iron oxide is ferromagnetic and superparamagnetic.

The secondary nanoparticles can be synthesized, for example, by combining a hydrophobic phase with a hydrophilic phase. Poly(D,L-lactide-co-glycolide) (6 mg), OA-SPIONs (3 mg), synthesized in 2.1, and chloroform (1 mL) were sonicated to form the hydrophobic phase. DSPE-PEG-NH-2 (0.563 μmol), L-α-Phosphatidylcholine (0.571 μmol), and 4% ethyl alcohol (3 mL) were magnetically stirred at 72° C. to make the hydrophilic phase. pHrodo-PE, used to dye the outside of the particle, was synthesized by conjugating pHrodo-succinimidyl ester to dipalmitoyl-sn-glycero-3-phosphoethanolamine-N-dodecanylamine overnight in a mixture of chloroform and DMSO. The hydrophilic phase, hydrophobic phase, and pHrodo-PE were combined using a tip sonicator at 30% power for 3 minutes. The lipid-coated nanoparticles were obtained after mixture was attached to a Rotovap on house vacuum for 15 minutes to bubble out remaining chloroform, washed through a centrifugal filter tube, and then through a 0.45 μm filter disk. (Park Y C, Smith J B, Pham T, Whitaker R D, Sucato C A, Hamilton J A, Bartolak-Suki E, Wong J Y. Effect of PEG Molecular Weight on Stability, T2 contrast, Cytotoxicity, and Cellular Uptake of Superparamagnetic Iron Oxide Nanoparticles (SPIONs). 2014; 119:106-14; and Park Y, Whitaker R D, Nap R J, Paulsen J L, Mathiyazhagan V, Doerrer L H, et al. Stability of Superparamagnetic Iron Oxide Nanoparticles at Different pH Values: Experimental and Theoretical Analysis. Langmuir. 2012; 28:6246-6255, both incorporated herein by reference in their entirety as they relate to making the particles useful in the methods and compositions of the invention).

Accordingly, the invention provides a composition comprising a natural IgM-producing phagocytic lymphocyte (NIMPAB) cell; and at least one particle comprising a superparamagnetic iron oxide nanoparticle (SPION), wherein the SPION is dispersed in poly (lactic-co-glycolic acid) (PGLA) core and the core is coated with a lipid bilayer comprising phosphatidylcholine (PtC) and polyethyleneglycol (PEG); or wherein the SPION is dispersed in aqueous solution core and the core is coated with a lipid bilayer comprising phosphatidylcholine (PtC) and polyethyleneglycol (PEG), optionally wherein the aqueous solution core comprises a stabilizer, for example a stabilizer that is a catechol group modified poly (2-acrylamido-2-methyl-1-propanesulfonic acid) (pAMPS*) and the pH of the aqueous solution core is neutral; or wherein the SPION is coated with citric acid and the pH of the aqueous solution core is between or at about 8 and about 9.

In some or all aspects of the invention, the NIMPAB cell is a mammalian NIMPAB cells, such as a human, a primate or a murine NIMPAB cell.

In some or all aspects of the invention, the particle can be about 180-600 nm in diameter, for example, 200-600 nm in diameter, 200-300 nm in diameter, 210-250 nm in diameter, 220-280 nm in diameter, 220-250 nm in diameter, 200-400 nm in diameter, 300-600 nm in diameter or for example 400-600 nm in diameter, or for example 500-600 nm in diameter. In some aspects, the particles are about 220-240 nm. In some or all aspects, the particles are about 226 nm in diameter.

The SPIONs inside the particles can in some or all aspects be about 5-30 nm in diameter, 10-20 nm in diameter, for example 13-15 nm in diameter.

In some or all aspects of the composition the at least one particle is inside the NIMPAB cell. The particles of the invention are "ingested" by NIMPAB cells by phagocytosis.

The enriched composition can comprise at least about 20%, at least 30%, at least 40%, at least 50%, at least 60%, at least 70%, at least 80%, at least 90%, or at least 95% of cells that are NIMPAB cells comprising at least one particle comprising SPION particles inside the NIMPAB cell.

In some embodiments, the technology described herein allows one to outsource human hybridoma production, as well as develop antibodies for immunotherapy. Herein, the technology disclosed utilize the special phagocytosis features of NIMPAB cells, which involves internalization, or phagocytosis, of the particle comprising the SPION particles by the NIMPAB cell.

In some aspects of the invention, the inventors have demonstrated the ability to identify human NIMPAB cells from human peripheral blood using the specially constructed nanoparticles; the ability to rapidly enrich NIMPAB cells to at least greater than 20% in one step wherein the NIMPAB cells have phagocytized the nanoparticles; the ability to purify NIMPAB cells to greater than 95% by further isolation; and the ability to obtain human hybridoma clones from isolated NIMPAB cells. The inventors have shown that the cells, despite having internalized the nanoparticles, can function and produce IgM antibodies.

In addition, in some examples, the inventors have assessed the cancer-specificity of an IgM antibody from the experimental NIMPAB clones by performing immunohistochemistry (IHC) using normal and cancer tissue arrays. The data show that one can use the NIMPAB cells isolated and purified by the methods of the invention for large scale production of natural IgM antibodies that can target, e.g., a tumor or cancer tissue. In some embodiments, the IgM antibodies produced by the methods of the present invention are more efficient than IgG antibody in prevention and/or treatment of cancer, such as melanoma.

Herein, the inventors demonstrate the ability to establish human hybridoma fusion cells with NIMPAB cells, and provide establishing a standard immunohistochemistry screening of the human monoclonal NIMPAB cells for their tumor-specificity using the novel hybridoma cells.

The technology described herein addresses an unmet need of producing alternative and in some aspects, better antibodies for immunotherapy, namely IgM antibodies. The technology described herein provides methods and compositions for identifying, isolating, and cloning NIMPAB cells from tissues, for example, from human peripheral blood. The technology described herein will have an impact on, including but not limited to monoclonal antibodies and immunomodulator types, as well as monoclonal antibody-based therapy; cancer vaccines; checkpoint inhibitors-based therapy; and immunomodulators.

In some embodiments, the B lymphocyte population isolated according to the methods described herein can have numerous important applications. As an individualized medicine approach, isolation of this novel population of a patient's own white blood cells that have already been producing anti-cancer antibodies in the cancer patient can help preserve and expand autologous cells for cellular immunotherapy. Isolation, enrichment and production of a hybridoma cell line from patient's own cells provides a therapeutically feasible intervention as an individualized or personalized cancer therapy. Methods are therefore provided wherein the tissue sample comprising cells is taken from a subject who has been diagnosed with a disease, such as cancer, such as melanoma. Methods of using the antibodies produced by the cells isolated from the subject can then be used to make a production hybridoma cell line and antibodies produced by the hybridoma cell line can be returned to the subject as a therapeutic or preventative intervention.

As a preventive and general curative medicine approach, isolation and immortalization of these novel anti-cancer B cells from healthy donors, cancer patients or cancer survivors of a specific type of cancer can be used to establish human cancer-type-specific anti-cancer hybridoma libraries, from which individual antibodies or pools of cancer-specific human antibodies can then be used for both cancer immunotherapy and cancer diagnosis. Thus, in some or all aspects of the invention, the tissue sample can be taken from one or more healthy individuals, one or more individuals affected by a particular disease, such as specific cancer, such as melanoma. The isolated cells can again be used to make hybridoma cell lines that can provide production of various different IgM antibodies. These antibodies can be screened for efficacy against any particular disease, such as cancer, and then used as preventative or therapeutic intervention in patients.

Additionally, the use of nanoparticles as disclosed herein can be used to isolate NIMPAB cells from tissue sample comprising dissociated cells, such as dissociated tumor tissue or blood to allow efficient and rapid identification and screening of unique cancer-specific IgM antibodies as candidates for cancer immunotherapy.

The mechanism of the IgM production is such that the led molecule does not contain the highly specific binding sites of the IgG molecule. This permits the B cells to produce IgM rapidly during a primary immune response, while the IgG molecules take days to produce in quantity. The structure of the IgM molecule permits it to form a complex of five molecules, called a "pentamer" The pentamer informs the IgM function: the antibody is able to hind to many antigens simultaneously and can quickly clear antigens from the bloodstream during the initial stages of an infection.

The natural IgM antibodies allow recognition of a potentially broad range of cancer cells, giving them a distinct advantage over currently marketed therapeutic monoclonal antibodies, which typically only recognize a single mutant protein, or cancer antigen, that may or may not continue to be present on the cell surface as the cancer cell mutates to overcome the monoclonal antibody therapy.

The technology described herein has numerous advantages, such as, but not limited to (1) time-saving because clones can be rapidly obtained and fewer clones require screening because one can start with the highly enriched specific B cell population; (2) money-saving as cancer-type-specific pooling of these cells using the methods of the invention allows targeted clinical trials and cancer-type-specific combination of antibodies; (3) time and money saving because there is no need for humanization and genetic engineering of the IgM antibodies as the system allows them to be produced by isolated and enriched species-originated, such as human-originated cells; and (4) high efficiency, because IgM antibodies are highly disease-specific, have low cross-reactivity to normal tissue, and do not result in inflammation or cytotoxicity.

The methods of the invention can be used, for example, in making therapeutic antibodies against cancer. The central question of cancer therapy is to identify reagents or antibodies that specifically target tumor cells but not normal cells. All tumor antigens are essentially self-antigens that are expressed in the wrong cell type, in abnormal amount or in the wrong timing etc. Thus it is very hard to generate a totally tumor-specific reagent. The technology described herein solve this problem by looking into our body for the best solution. Different from traditional generation of anti-tumor antibodies, which involves identifying tumor antigen first followed by immunization of animals, our approach is totally natural. Herein, the inventors demonstrate that the true cancer-recognizing antibodies are natural IgMs that exist in healthy individuals. These antibodies protect most healthy individuals from the accumulation of cancerous cells before they can ever be detected.

However, the traditional methods to identify the B cells that secrete these naturally existing antibodies are laborious. It often took screening of thousands of human B cell hybridomas to obtain a few clones that would produce something useful. The technology described herein will significantly increase the efficiency of identification and isolation of naturally-existing cancer-specific B cells.

The technology described herein utilizes the unique features of the naturally-existing cancer-immuno-surveillance cells, NIMPAB cells, to identify and clone the natural IgM antibodies produced by NIMPAB cells. These features include the PtC-specific phagocytosis capacity and specific combination of surface markers of these cells. The methods use modified superparamagnetic particles that are specifically engulfed or ingested by the NIMPAB cells by phagocytosis and allow pulling the cells out from the vast majority of other leukocytes in the blood or other tissue samples comprising dissociated cells.

The methods are revolutionary. For example, the methods allow using IgM antibodies instead or in addition to the xeno-immunization-based humanized monoclonal antibodies that target tumor-specific antigens that often end up not specific at all and carry with them a significant risk of inflammation. The methods also allow efficient identification and cloning of naturally-existing B cells that were born to recognize cancer at very early stages naturally. These B cells are numerically rare in human blood. Therefore, it has typically taken tremendous effort to clone any of these B-cells in traditional ways. Our invention utilizes the newly discovered specific phagocytic function and tissue recognition of the NIMPAB cells to design the superparamagnetic iron oxide nanoparticles that will be specifically engulfed by the NIMPAB cells for quick isolation and cloning.

Accordingly, we provided are a composition comprising (a) a natural IgM-producing phagocytic lymphocyte (NIMPAB) cell; and (2) at least one particle comprising a superparamagnetic iron oxide nanoparticle (SPION).

In some or all aspects of the invention, the SPION in the composition is dispersed in poly (lactic-co-glycolic acid (PGLA) core and the core is coated with a lipid bilayer comprising phosphatidylcholine (PtC) and polyethyleneglycol (PEG).

In some or all aspects of the invention the SPION is dispersed in aqueous solution core and the core is coated with a lipid bilayer comprising phosphatidylcholine (PtC) and polyethyleneglycol (PEG).

The aqueous solution core may comprise a suitable stabilizer.

The suitable stabilizer can be, for example, a catechol group modified poly (2-acrylamido-2-methyl-1-propanesulfonic acid) (pAMPS*) and the pH of the aqueous solution core is neutral.

The SPION can be coated with citric acid and when it is, the pH of the aqueous solution core is between or at about 8 and about 9.

The NIMPAB cell can be any eukaryotic cell, for example, a mammalian cell, for example a human, a primate or a murine cell.

The particles, or nanoparticles, as present in the compositions or as used in the methods described herein are 200-600 nm, optionally 200-300, optionally 300-600 nm, optionally 400-600 nm, optionally 500-600 nm in diameter. The diameter of the particles can be essentially uniform, but can also vary between a small range, such as 200-250 nm, or 220-230 nm. The nanoparticle in the compositions or the methods comprises a SPION, that can be 10-20 nm in diameter, for example, 10, 11, 12, 13, 14, 15, 16, 17, 18, 19, or 20 nm in diameter, for example, 12-17 nm in diameter, for example, 13-15 nm in diameter. The SPIONs can be of uniform diameter or a mixture of particles with diameter ranging between the values as set forth above.

The invention provides a composition wherein at least one particle is inside the NIMPAB cell, i.e., phagocytized by the NIMPAB cell.

The composition can comprise at least 20%, 30%, at least 40%, at least 50%, at least 60%, at least 70%, at least 80%, at least 90%, or at least 95% of cells that are NIMPAB cells comprising at least one particle inside the NIMPAB cell.

Also provided is a method for producing a cell sample enriched with natural IgM-producing phagocytic lymphocyte (NIMPAB) cells, the method comprising the steps of ex vivo contacting a particle comprising a superparamagnetic iron oxide nanoparticle (SPION) with a dissociated cell sample thereby forming a mixture of the particles and dissociated cells.

In some or all aspects of the compositions and methods of the invention the at least one particle, or nanoparticle, also indicated herein and throughout the specification as sNP, comprising the SPION is dispersed in poly (lactic-co-glycolic acid (PGLA) core and the core is coated with a lipid bilayer comprising phosphatidylcholine (PtC) and polyethyleneglycol (PEG).

In some or all aspects of the compositions and methods of the invention the at least one particle the SPION is dispersed in aqueous solution core and the core is coated with a lipid bilayer comprising phosphatidylcholine (PtC) and polyethyleneglycol (PEG) and optionally, wherein the aqueous solution core comprises a stabilizer, for example, a catechol group modified poly (2-acrylamido-2-methyl-1-propanesulfonic acid) (pAMPS*) and wherein the pH of the aqueous solution core is neutral.

In some or all aspects of the compositions and methods of the invention the at least one particle the SPION is coated with citric acid and the pH of the aqueous solution core is between or at about 8 and about 9; incubating the mixture in a container to allow phagocytosis of at least one of the particles by a NIMPAB cell present in the dissociated cell sample. The dissociated cell sample comprises cells that are dissociated from any tissue and can be of any mammalian origin, for example, human, primate or murine origin.

Methods for dissociating cells, include e.g., a gentle collagen treatment which is well-known to one of ordinary skill in the art, as well as are other methods for tissue dissociation.

The method further comprises contacting the container comprising the particle and the cells with a magnet to attract the cell/cells that has/have phagocytosed the particle, wherein the magnets attracts the cell to the part of the container in contact with the magnet.

The method further comprises a step of discarding the dissociated cells not attracted to the magnet thereby obtaining a cell sample enriched with NIMPAB cells.

The method can further comprise dissociating the magnet and the container, and optionally washing the cell sample enriched with NIMPAB cells; and optionally subjecting the cell sample enriched with NIMPAB cells to fluorescent activated cell sorting. Optionally, the cells can be stained for, for example, CD19, CD20 and CD5 and CD14, prior to cell sorting.

If the tissue is a solid tissue, one will dissociate the cells prior to mixing them with the nanoparticles so that the dissociated cell preparation can be mixed with the nanoparticles in a suitable cell culture medium to allow phagocytosis of the particles by the NIMPAB cells in the dissociated cell sample.

The dissociated cell sample can be a blood sample wherein a separate tissue dissociation is not needed.

The dissociated cell sample is a sample made of, for example, a normal or non-disease-affected tissue or a tumor tissue.

The method of any one of the claims 11-14, wherein the particle is 200-600 nm, for example 200-300 nm, 300-600 nm, for example 400-600 nm, for example 500-600 nm in diameter.

Further provided is an isolated natural IgM-producing phagocytic lymphocyte (NIMPAB) cell comprising at least one superparamagnetic iron oxide nanoparticle (SPION) produced by any of the methods described herein.

Further provided is a method for producing tissue-specific IgM antibodies comprising the steps of producing a hybridoma cell by fusing an isolated NIMPAB cell comprising at least one SPION with an immortalized cell; exposing the hybridoma cell to an optimal culture medium for a time sufficient to allow production of IgM antibodies thereby causing production of IgM antibodies; optionally screening for IgM antibodies against the tissue-sample; optionally isolating the IgM antibodies against the tissue-sample; and optionally purifying the isolated IgM antibodies against the tissue-sample.

In some or all aspects of the methods, the immortalized cell can be of human, primate or murine origin.

In some or all aspects of the methods, the immortalized cell can be a Karpas 707 cell.

In some or all aspects of the methods, the immortalized cell can be a B6B11 cell.

In some or all aspects of the methods, the immortalized cell can a mouse SP20 cell.

In some or all aspects of the methods, the tissue-sample is from a tumor tissue, wherein the tumor can be a solid tumor, such as a sarcoma, carcinoma, or a lymphoma. In some or all aspects of the methods, the he solid tumor is melanoma.

In some or all aspects of the methods, the tumor is leukemia.

Also provided is a method for the treatment of disease comprising administering to a subject affected with the disease an IgM antibody produced by the any of the methods as set forth herein.

In some or all aspects of the methods, the disease is cancer.

In some or all aspects of the methods, the cancer is caused by a solid tumor.

In some or all aspects of the methods, the solid tumor is a sarcoma, carcinoma, or a lymphoma.

In some or all aspects of the methods, the solid tumor is melanoma.

In some or all aspects of the methods, the cancer is caused by a leukemia.

The inventors have assessed at least 3 exemplary formulations of the nanoparticles to achieve the maximal amount of iron per particle and maximum PtC surface decoration to allow the NIMPAB cells to phagocytize the particles. In one example, the inventors separated NIMPAB cells from human blood samples with external magnet-responsive nanoparticles (500~600 nm diameter). In this example, each nanoparticle core contains superparamagnetic iron oxide nanoparticles (SPIONs) (10 nm diameter). The magnetic core structure allows SPION to aggregate under an external magnetic field, hence transitioning from superparamagnetism to paramagnetism. The surface of each nanoparticle is then coated with PtC lipids. The inventors chose to incorporate PtC lipids into the system according to previous studies that have shown that NIMPAB cells are able to phagocytize PtC-coated silica nanoparticles around 500-600 nm in diameter (Vo, H et al. Immunity, Inflamm. Dis. 2015, 2 (4), 254-261). In Vo, in order to confirm the phagocytosis process, pH sensitive pHrodo-red was conjugated with PtC units that formed phospholipid bilayers on the surface of silica beads, where fluorescence intensity increases as pH decreases when beads are exposed to the cytosol after lysosome fusion. In contrast, herein and in order to reduce cell toxicity and prevent protein corona formation, polyethylene glycol (PEG) conjugated to a phospholipid was incorporated into the nanoparticle surface in addition to the PtC lipids.

First the inventors assessed a Route 1 design (FIG. 13), where poly (lactic-co-glycolic acid) (PLGA) is used, allowing hydrophobic SPION embedment in the nanoparticle core. Due to the PLGA hydrophobicity, a single layer of PtC, lipid-pHrodo-red, lipid-PEG can form on the nanoparticle core. PtC allows specific engulfment of NIMPAB; lipid-pHrodo can be used to confirm the phagocytosis process; lipid-PEG can allow nanoparticle dispersion in the human blood sample prior internalization of NIMPABs. After dispersing nanoparticles in the blood sample, NIMPAB phagocytosis is allowed to occur overnight, then an external magnet is placed on the side of the sample tube for several minutes. During this time, aggregation of SPIONs occurs, and the nanoparticles become paramagnetic and pull NIMPABs out to the side-wall of the sample tube. Cell separation is followed by washing, and flow cytometry to further access and purify cells, and separate possible contamination of activated macrophages from NIMPAB cells.

In another example of suitable particles was prepared. In this example, when suspended in media, the nanoparticles (sNps) had an average diameter of 226 nm. The SPIONs inside the nanoparticle were approximately 13~15 nm. The inventors used fluorescent labeling to demonstrate that these particles were also taken up by phagocytosis by the NIPAB cells. The pHrodo-red and PtC on the outside of the nanoparticle only displayed as red when in an acidic environment, such as lysosome inside a phagocyte. Mouse peritoneal washout cells were analyzed after macrophage plate adhesion depletion followed by overnight incubation with pHrodo-red. Yellow dots indicated phagocytosed sNP in ZsGreen-expressing mouse NIMPAB cells. A higher magnification view of plate adherent macrophages without sNP was shown. Plate-adherent macrophage after incubating with sNP was shown. Non-adhesive fraction of the macrophage-depleted PCW cells collected. Non-adherent PCW after incubation with pHrodo-red-sNP was shown. Yellow dots indicated internalized pHrodo-red sNP by NIMPAB cells that express ZsGreen.

Figure 13:
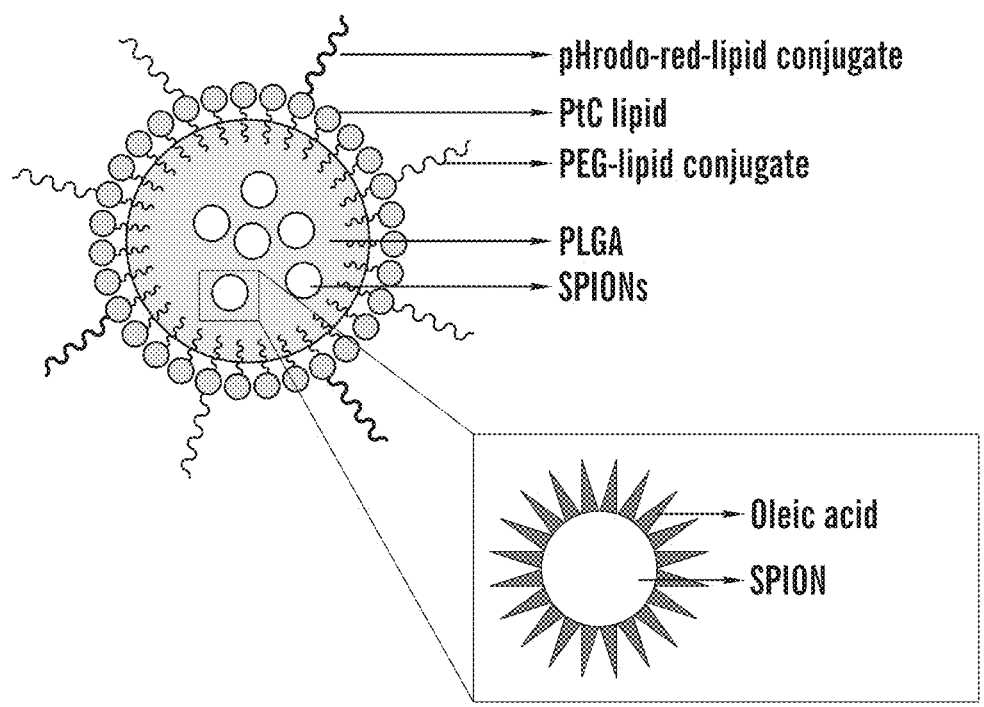
FIG. 13 is a schematic diagram of Route 1 single layer PtC-lipid coated nanoparticle with aqueous-SPIONs core.

For example, Route 1 as described in FIG. 13, allows easy tuning of nanoparticle core size, SPION concentration, and diffusivity of SPIONs in the PLGA core, in order to achieve responsive paramagnetism, while changing magnetic sensitivity. Iron oxide in SPIONs is ferromagnetic and superparamagnetic.

Additional routes can be also utilized in making the particles, such as Routes 2 and 3 (FIG. 14), where hydrophilic SPIONs are dispersed in an aqueous environment inside of lipid bilayers, where the chemical composition of the lipid coating is the same as Route 1. In Routes 2 and 3, SPIONs do not aggregate in the nanoparticle core, hence SPIONs need to be stabilized with coatings in an aqueous environment.

For Route 2 (FIG. 14B), catechol group modified poly (2-acrylamido-2-methyl-1-propanesulfonic acid) (pAMPS*) can be used to allow single SPION dispersion in pH neutral aqueous environment.

For Route 3 (FIG. 14C), citric acid-coated SPIONs can be dispersed in a pH 8-9 aqueous environment inside lipid bilayers.

Surface coating density (number molecules per $nm^2$) of lipid-pHrodo-red, and lipid-PEG can influence the time and efficiency of phagocytosis, lysosome de-fusion, and exocytosis. Accordingly, one of ordinary skill in the art can optimize the ratio between PtC:lipid-pHrodo-red:lipid-PEG. If surface groups of pHrodo-red or PEG prevent any of these three processes, one of ordinary skill can also use Route 4 (FIG. 15A), where each SPION is coated with (3-aminopropyl)triethoxysilane (APTS) linked rhodamine green dye (FIG. 15B). The SPIONs are then encapsulated with a single PtC-lipid layer. Resulting nanoparticles from Route 4 only contains PtC on its surface, with fluorescence in the core for cell tracking.

Accordingly, the inventors developed a particle that can be phagocytosed specifically by NIMPAB cells, and optionally, can be evaluated by PHRODO dye to distinguish the surface and internalized particle. The particle does not kill the cells, which can be evaluated by, e.g., AOPI staining of the cells, with the NIMPAB cells retaining the capacity to produce IgM as evaluated by, e.g., a LPS stimulation and ELISA assay.

The inventors assessed the phagocytosis efficiency of the NIMPAB cells to achieve the optimal particle per cell density to allow maximal magnetic strength for quick isolation of peripheral NIMPAB cells. Different formulations of the particle were compared and evaluated by fluorescent microscopy and quantitative imaging analysis. Examples of the particle formulation that gives maximum particle per cell phagocytosis in NIMPAB cells that can be used, or further selected for analysis are described herein.

The inventors assessed the isolation efficiency and purity using flow cytometry analysis. Human blood samples or buffy coat were mixed with the optimal nanoparticles at different ratios followed by incubation for 3-6 hours. Cells were split into two samples. One flows through a magnetic column. The other one is used as an unpurified control. Cells can be further stained with additional cell surface markers to distinguish different cell populations and analyzed by flow cytometry. A particle ratio and incubation time can be determined by determining the percentage of NIMPAB cells that phagocytosed the particle and the purity as compared to the control sample.

In some or all aspects of the methods of the invention, the cells and the particles are incubated to allow time for phagocytosis. In some or all aspects of the invention, the incubation time can be about 1-24 hours, for example 1-12 hours, for example, 1-10 hours, for example 2-24 hours, for example 2-12 hours, for example, 2-10 hours, for example, 2-6 hours, for example, 3-24 hours, for example 3-12 hours, for example 3-10 hours, for example, 3 to 6 hours.

In some or all aspects of the methods and compositions of the invention, the ratio of the cells to particles in the mixture of cells and particles is about 1:100, for example 1:90, for example 1:80, for example 1:70, for example 1:60, for example 1:50, for example, 1:40, for example 1:30, for example 1:20, for example 1:10.

In some aspects, the method further comprises establishing a hybridoma fusion cell to allow production and screening for a number of IgM variants from a subject that are produced by the variety of naturally occurring, NIMPAB cells isolated and enriched by the methods of the invention.

For example, the inventors have isolated human NIMPAB cells from blood sample and fused with an exemplary partner human cell line. Karpas 707, a hypoxathine-aminopterin-thymidine (HAT)-sensitive and ouabain-resistant human myeloma cell line was used as a fusion partner. NIMPAB cells isolated from PBMC were fused with Karpas 707 using the standard PEG fusion protocol. Hybridoma clones were assessed and selected for secretion of IgM antibodies. The hybridoma cells are cultured in HAT for 12 days, and the supernatant from each clone assessed for the secretion of IgM using standard ELISA. Immunohistochemistry (IHC) analysis was also used to test the specific binding of these monoclonal human IgM antibodies to human cancer tissue but not normal tissue.

Other cell lines that provide similar qualities to Karpas 707 line can be used. For example, for making human hybridoma clones, one can use a human B6B11 cell line or a mouse SP20 cell line. One of ordinary skill in the art will be able to assess, with the information provided herein, other suitable cell lines for making hybridoma cells from the IgM-producing cells for human hybridoma cells as well as for hybridomas for other mammalian cells, such as primate or murine cells.

Figure 9A:
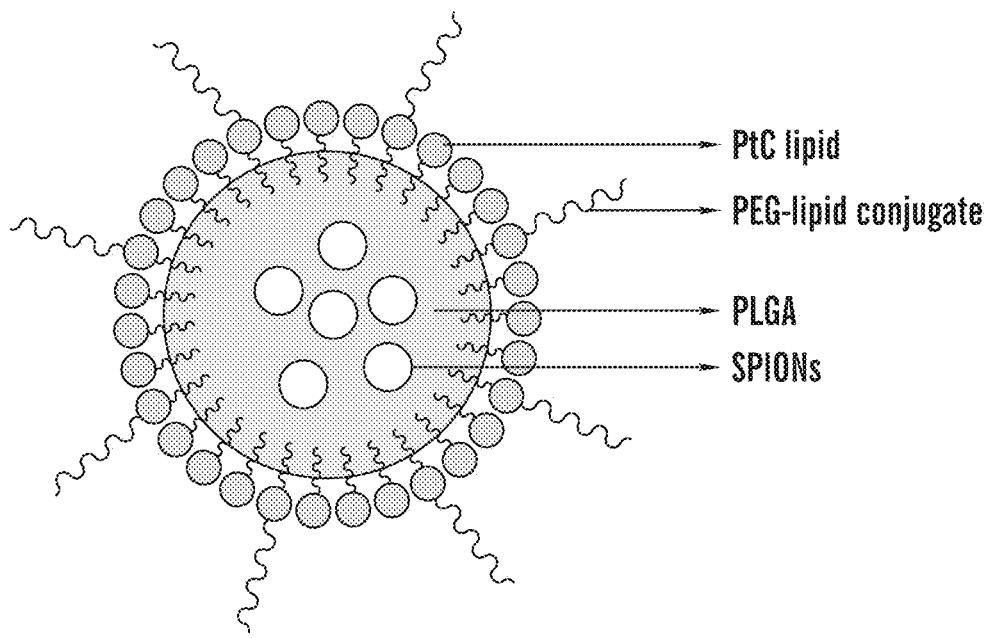
FIGS. 9A-9D show mouse NIMPAB cell sNP phagocytosis and magnetic enrichment.
Figure 9B:
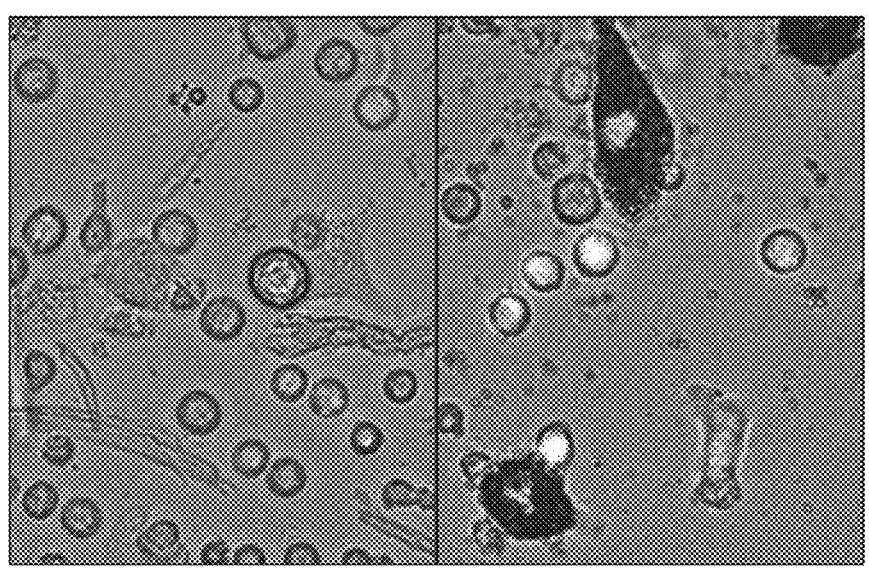
Figure 9C:
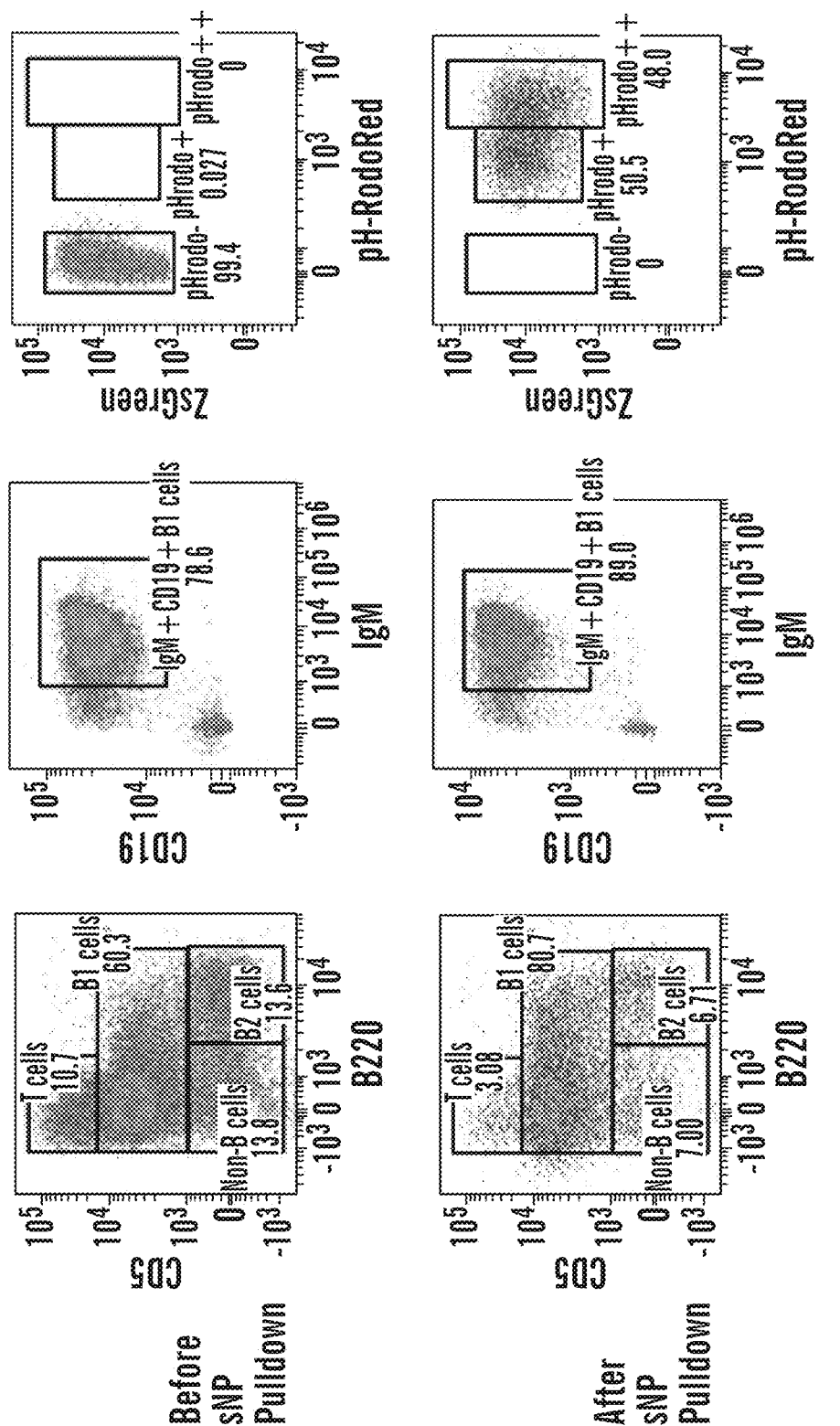
Figure 9D:
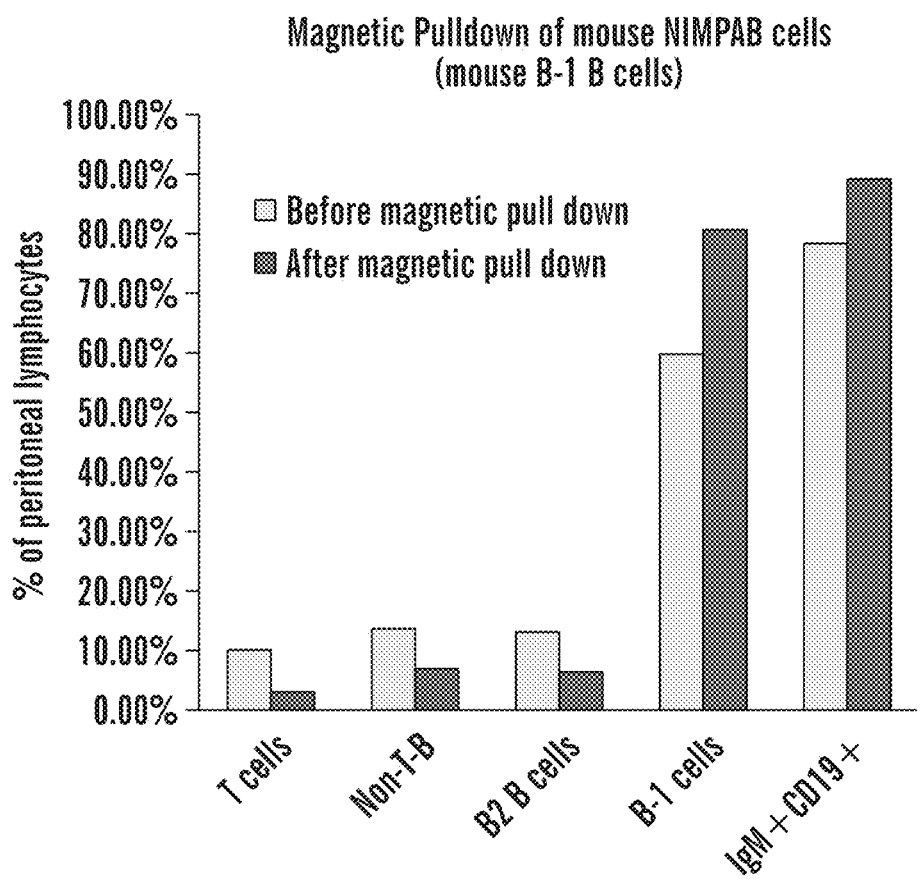

Existing methods to produce IgM-producing hybridomas from NIMPAB cells purified from blood was performed. The inventors modified the standard human hybridoma fusion protocol for NIMPAB cells (FIG. 9A), and demonstrated that they could generate human hybridoma clones (FIG. 9B). The inventors obtained primary human cells from peripheral blood or cord blood samples and other human tissues and fused with the human partner myeloma cell line.

IgM-positive clones were selected and expanded, and the supernatant of these clones used for IHC analysis on human cancer tissue microarray. Clones that secreted IgM that only react to tumor tissues and not normal tissues were selected.

The B cell population that generates the natural IgM antibodies share many cell surface markers with other immune cells. Therefore, it is more difficult and less efficient to use traditional cell isolation methods such as magnetic beads that rely on cell surface markers or flow cytometry that uses antibodies specific for those markers. The methods as provided herein allow rapidly enriching a rare antibody-producing B cell population, and in contrast to existing technologies, utilizes a special phagocytosis feature unique to this population of B cells to allow use of a magnet in the isolation and enrichment methods.

Figure 16:
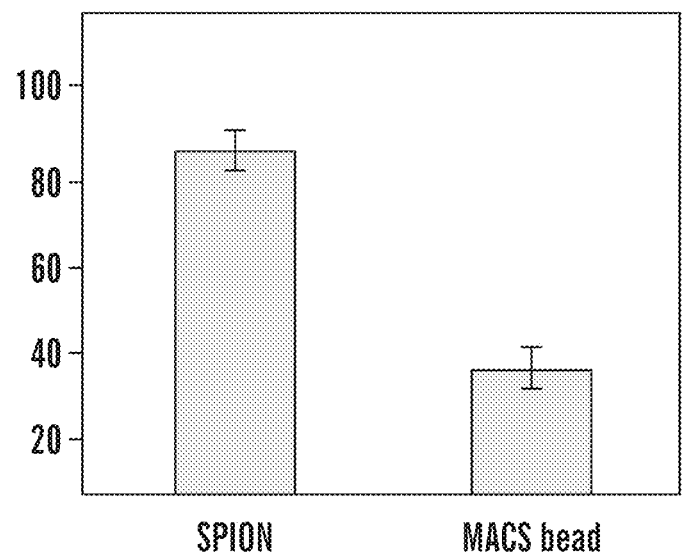
FIG. 16 shows the percentage of magnetic pull down of SPION vs. magnetic macro-beads (MACS based magnetic beads) using a conventional magnet.
Figure 17A:
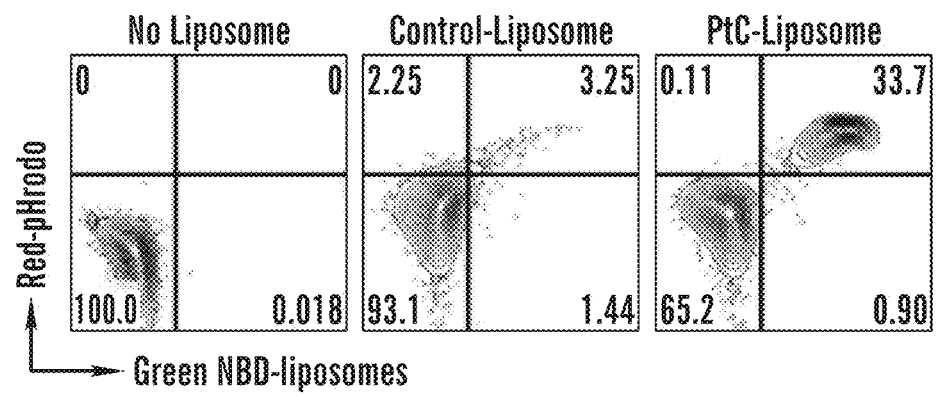
FIGS. 17A-17B show L2pB1 cells are the predominant NIMPAB in mouse.
Figure 17B:
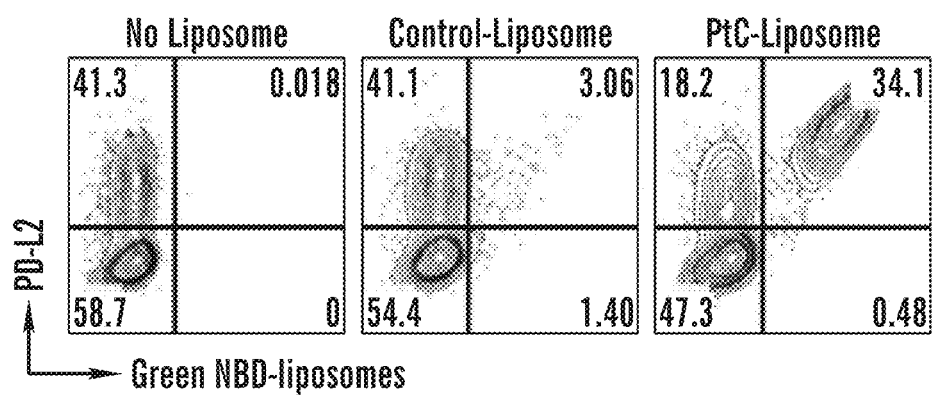

Herein, the inventors have assessed the magnetic properties of nanoparticles (sNP) against MACS beads (the most popular magnetic macro-beads on the market). The inventors demonstrate that a significantly higher percentage of the SPION nanoparticles (see FIG. 16) are pulled down by a magnet than for the MACS beads. This magnetic strength is important for maximizing enrichment efficiency to include small B cells that phagocytose a limited number of particles. Due to the scarcity of NIMPAB cells in the peripheral blood, it is calculated that it would take roughly 5 years using traditional flow cytometer-based sorting methods to obtain and screen a sufficient number (thousands) of hybridoma clones to identify a reasonable number of acceptable cancer-specific antibody-producing clones. By using the novel isolation, cloning and screening methods disclosed herein, the cycle time is expected to be a few months from patient sample to the development of a cancer-specific monoclonal antibody.

Instead of looking for single tumor antigen or biomarkers, the inventors have isolated and utilized naturally existing B cells that secrete anti-tumor natural IgM antibodies; these natural IgM antibodies differ from conventional antibodies used in most current immunotherapy in that they are low affinity, high avidity, poly-reactive and recognize cell patterns through lipid and carbohydrates modification and other macro-molecules like DNA and RNA. The inventors have utilized the unique features of these special B cells to create a rapid enrichment of these rare cell population from donor or patient blood without the need to extract them from tumor tissue.

Figure 11:
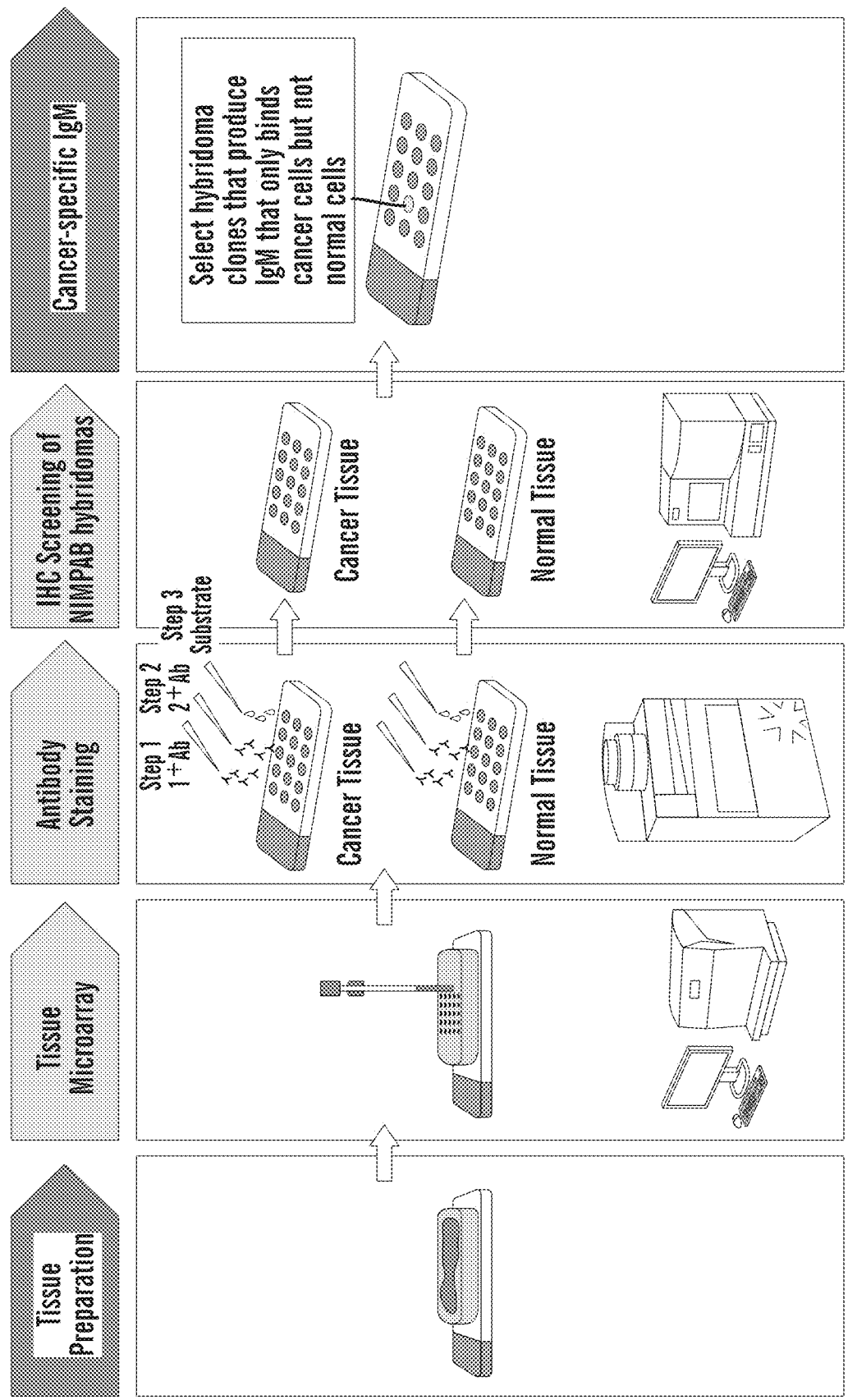
FIG. 11 illustrates the screening strategy of human NIMPAB hybridoma clones for tumor-specificity. Tissue microarray (TMA) will be generated from 50~100 melanoma patient tissue blocks. Supernatant of the NIMPAB hybridoma clones containing natural IgM can be used for immunohistochemistry (IHC) analysis. Hybridoma clones that only binds tumor TMA but not control normal TMA are selected

The inventors demonstrate herein proof-of-principle experiments that demonstrate isolating NIMPAB cells as a source of broad-spectrum anti-cancer antibodies (FIG. 7). Briefly, IgM isolated from a NIMPAB cell-rich tissue (i.e. PCW) in a naïve animal recognizes melanoma cells, whereas IgM isolated from a NIMPAB cell-poor tissue (i.e. spleen) does not (FIG. 7). Similarly, Peritoneal Cavity Washout (PCW) cells, a NIMPAB-enriched population, clearly inhibit tumor spheroid growth whereas splenocytes, a NIMPAB-poor population, does not (FIG. 11).

In addition, a FACS (fluorescence activated cell sorting) study demonstrated that human NIMPAB cells identified from peripheral blood could ingest lipid-coated nanoparticles (FIG. 1C). Therefore, these data indicate that ingestion of magnetic lipid-coated particles is a more efficient way to rapidly isolate these cells compared with traditional FACS approaches.

Figure 8:
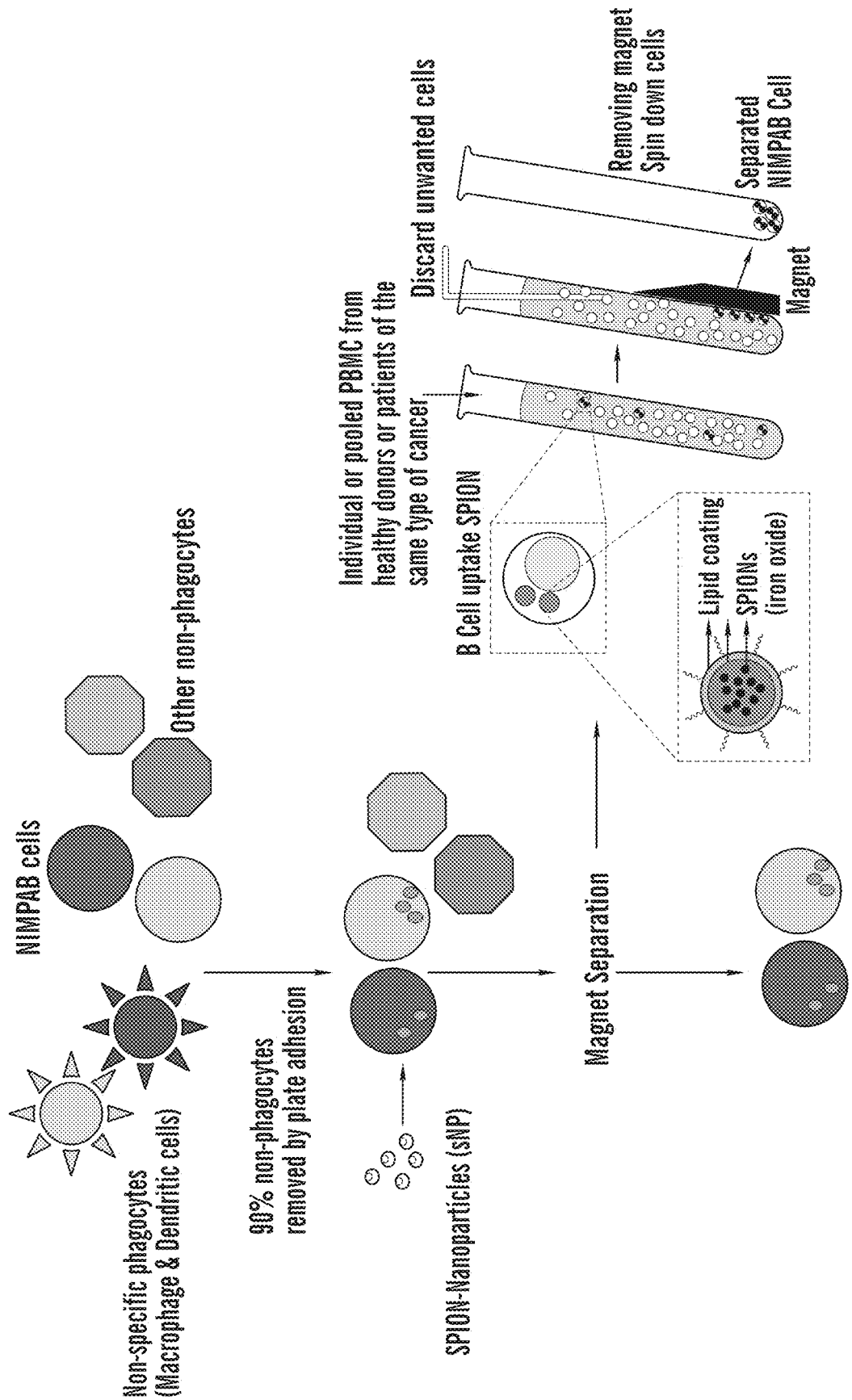
FIG. 8 shows a flow chart of rapid isolation of NIMPAB cells using a NIMPAB-specific modified superparamagnetic iron oxide nanoparticles (SPIONs) and a magnet.

Exemplary methods for making lipid modified SPIONs (superparamagnetic iron oxide nanoparticles) are described herein. The inventors herein have developed magnetic nanoparticles (SPIONs) and used them in a protocol for isolating NIMPAB cells from human blood. The sNP composition and methods as disclosed herein, is depicted in FIG. 8. The choice to coat iron oxide nanoparticles rather than commercially available magnetic macrobeads was based on the potential for large beads to have toxic post-ingestion effects based on their size, and on data showing superior performance of the disclosed SPIONs. This strong magnetic response (see FIG. 16) enables one to isolate B cells that phagocytose only a limited number of particles. Human NIMPAB cells can therefore be magnetically isolated from whole blood using the SPION nanoparticles disclosed herein and human NIMPAB cell enrichment can be compared to traditional FACS sorting methods.

The inventors screened the hybridoma IgM antibodies for cancer specificity using a library of cancerous tissue microarray (TMA). Melanoma samples were used which are obtained retrospectively from previous skin biopsies of melanoma patients, with normal skin samples acting as an internal control.

In addition to previously obtained skin samples as above, and to allow for capture of future specimens to allow for larger scale analyses melanoma samples from skin biopsies can be assessed after obtaining patient consent at the time of biopsy.

Herein, the technology described herein uses a novel rapid isolation method to isolate NIMPAB cells from peripheral blood of patients of with specific types of cancer; or cancer survivor donors of the same specific type of cancer. The inventors have also demonstrated in vivo animal models of individual or pooled natural IgM antibody for late-stage melanoma, as well as established a human monoclonal NIMPAB hybridoma library from late-stage melanoma patients and obtain industry-scale production of the natural IgM antibodies for clinical trial use.

Immunotherapy has gained unprecedented attention in oncology in the past few years. 40% of $100 billion worldwide oncology drug spending is cancer immunotherapy in 2014. Recent success of check point-based immunotherapy also revealed many concerns over immune system-mediated severe side effects, and suboptimal response rates. The mainstream of the field is currently trending towards discovering more new check point targets and biomarkers, as well as combining different targeted therapies. However, these efforts do not solve the inherent problems of these severe inflammatory side effects, tumor heterogeneity and drug resistance due to cancer evolution, and may in fact speed up cancer evolution by selecting for cancer cells that outgrow the treatment. Herein, the inventors have demonstrated that the technology described herein is a real innovation in this field and allows pattern recognition-based, tumor-antigen-independent targeting method.

Using this technology, the inventors can search for existing anti-tumor immune cells and antibodies in humans (both patients and healthy donors) rather than develop xenoantibodies de novo and avoids the need of molecular engineering to humanize them. Moreover, the IgM antibodies as produced by the methods described herein may be more effective and less toxic than currently existing immunotherapy products.

The technology described herein can be used for the treatment of cancer. An exemplary cancer is melanoma, including but not limited to early-, mid- and late-stage melanoma patients.

Melanoma is a skin cancer which develops from the neoplastic transformation of melanocytes in the skin. Although melanoma accounts for less than one percent of skin cancer cases, it causes the vast majority of skin cancer deaths. The estimated 5-year survival rate for early stage melanoma is approximately 98 percent in the U.S. The survival rate falls to 62 percent when there is metastasis to the lymph nodes, and 18 percent when there is distant organ metastasis. Exposure to UV radiation remains the most important risk factor for developing melanoma.

Melanoma is one of the few remaining cancers in the US that is still increasing in incidence and it is now the fifth and seventh most common cancer in men and women respectively, in the US. Currently the lifetime risk of developing melanoma for Americans is 1 in 59. Deaths from melanoma are also on the increase. In 2017, it is estimated that there will be 87,110 new cases of melanoma of the skin and an estimated 9,730 people will die of this disease.

Current immunotherapy approaches for the treatment of melanoma but they have shortcomings.

For example, recent greater understanding of the immunobiology of melanoma has led to the development and use of immunotherapy to treat metastatic melanoma. The most significant advances have come from the use of monoclonal antibodies against critical immune-regulatory pathways, in particular, immune checkpoint inhibitors. CTLA-4 is a critical checkpoint inhibitor expressed on regulatory T cells, where it downregulates T cell activation to prevent autoimmunity and allow self-tolerance. Ipilimumab, a monoclonal antibody which blocks CTLA-4 is FDA approved in the treatment of metastatic melanoma after showing improved survival for the first time in clinical trials of advanced stage melanoma patients. However, response rates are low ~11% and the use of this drug is associated with immune mediated toxicities leading to significant adverse events that can be life-threatening. Another approach is to use monoclonal antibodies against another critical immune checkpoint molecule, PD-1, which is present on T cells in the effector phase. The ligand for PD-1 is PD-L1 which is expressed by many cancers including melanoma, and this binding contributes to tumor-induced immunosuppression, leading to tumor resistance to cytotoxic T cell responses.

Pembrolizumab is a humanized monoclonal antibody against PD-1 which is FDA approved for metastatic melanoma. Clinical trials in advanced melanoma have shown over-all response rates (ORR) of 34% with overall survival of 69% at 1 year. In head-to-head trials of pembrolizumab versus ipilimumab, pembrolizumab performed significantly better with ORR of 33% (pembrolizumab) versus 12% (ipilumumab). Although associated with immune mediated side-effects, they tended to be less frequent and severe in pembrolizumab compared to ipilimumab. A second PD-1 inhibitor approved for the treatment of advanced melanoma is nivolumab. Clinical trials in metastatic melanoma using the combination of a CTLA-4 inhibitor with a PD-1 inhibitor (ipilimumab and nivolumab) led to greater and more durable response rates than either drug alone (ORR nivolumab alone −44%; ipilimumab alone 19%; nivolumab+ipilimumab 58%). However, this benefit is counterbalanced by greater toxicity, grade ¾ (Adverse events: nivolumab alone −16%; ipilimumab alone 27%; nivolumab+ipilimumab 55%).

Although immunotherapy has made a significant impact in the management of advanced melanoma, there is still an inadequately met clinical need given the low response rates, together with significant immune mediated toxicities associated with the use of these drugs. Although combination immunotherapy has shown improved response rates, this is counterbalanced by worse toxicities. As a result, there is currently a search for predictive biomarkers that will predict which patients will benefit from these expensive treatments and which will not, and therefore spare patients from unnecessary adverse events. In addition, studies are ongoing to evaluate other combination immunotherapies, combination of immunotherapies with targeted therapies and the search for other immune checkpoint modulators. Thus although significant advances have been made with regards to immunotherapy in melanoma, there is still an inadequately met clinical need.

The use of NIMPAB cells and the technology described herein as a novel form of immunotherapy to treat advanced melanoma is likely to overcome many of the problems highlighted above. Given the 'pattern recognition' trait of NIMPAB cells versus targeting a specific cell epitope, they could more specifically target melanoma cells even when the melanoma evolves and tries to progress. This would suggest a more durable response. NIMPAB cells are generated and isolated by the patient themselves, therefore there is no need for humanization and bioengineering which is required of currently available xeno-immunization. This would predict NIMPAB cells to function more effectively and also reduce manufacturing costs. In addition to low cross-reactivity to normal tissue, they also function via pathways that are of low inflammation and cytotoxicity and so one would expect fewer adverse events with their use.

A clinical trial to assess natural IgM anti-melanoma antibodies for the treatment of melanoma can be performed. A study population can be determined (e.g adults, males and females, all ethnic groups, stage IV melanoma that has failed other FDA-approved therapies). Exclusion criteria will be determined (e.g pregnant or nursing women, or premenopausal women who refuse to take adequate contraception). The study design can be a Phase I trial, with the aim of the study to implement the cloned natural IgM anti-melanoma antibodies, and determine the feasibility, tolerability and safety of this drug in stage IV melanoma patients that have failed other FDA approved therapies. One can use a sample size would be 10 based on the number of subjects expected to meet eligibility criteria during the defined study period. Eligible patients will receive intravenous administration of cloned natural IgM anti-melanoma antibodies at predetermined intervals starting with the lowest dose for the first 3 cases and increasing the dose for the next 3 cases and so on, if symptoms allow.

Immunotherapy has gained unprecedented attention in oncology in the past few years. 40% of $100 billion worldwide oncology drug spending is cancer immunotherapy in 2014. VC investment in fact doubled that year. According to a 2016 report, the market will continue to more than double by 2020. As rapidly as it rises, investment in immunotherapy is expected to quickly reach saturation due to lack of out-of-box innovation in the field. Recent success of check point-based immunotherapy also revealed many concerns over immune system-mediated severe side effects, and suboptimal response rates. The mainstream of the field is currently trending towards discovering more new check point targets and biomarkers, as well as combining different targeted therapies. However, these efforts do not solve the inherent problems of these severe inflammatory side effects, tumor heterogeneity and drug resistance due to cancer evolution, and may in fact speed up cancer evolution by selecting for cancer cells that outgrow the treatment.

The technology disclosed herein represents a real innovation in this field, which is to create a pattern recognition-based, tumor-antigen-independent targeting method. The present technology disclosed herein provides both time- and money-saving because it allows one to search for the existing anti-tumor immune cells and antibodies in humans (both patients and healthy donors) rather than develop xenoantibodies de novo and use molecular engineering to humanize them. Moreover, the technology disclosed herein will be widely accepted by clinicians because it would likely be more effective and less toxic than existing products.

For example, inventors showed human NIMPAB cells from peripheral blood. Peripheral PBMC was obtained from healthy donor and incubated over night with PtC-modified-nanoparticle (green) and control nanoparticles (red) at 1:20 ratio. Cells were then stained for CD19, CD20 and CD5 and CD14. In this case, 15% of CD19+CD20+ B cells specifically phagocytose PtC-nanoparticles whereas CD14+ monocytes phagocytose both PtC-nanoparticles and control nanoparticles. Results were representative of four experiments.

Inventors further showed that L2pB1 cells are required for inhibiting B16F10 melanoma cells. CD19-Cre-PZTD mice were injected with Diphtheria toxin (DT) to deplete L2pB1 cells. An almost complete loss of PD-L2+ B-1 B cells (PD-L2+TdTomato+) was shown. B16F10 melanoma cells were cultured alone for 3 days. B16F10 melanoma cells were co-cultured with wild type peritoneal cells. Most B16 cells were dying by day 3. B16F10 melanoma cells were co-cultured with total spleen cells. No inhibition was seen. B16F10 melanoma cells were co-cultured with L2pB1 cell-depleted peritoneal cells. B16F10 melanoma cell inhibition and cell death were significantly diminished.

Inventors demonstrated that mouse peritoneal cells induce lipoptosis of melanoma cells. Melanoma cell B16F10 were incubated alone or with peritoneal cells. Peritoneal cells contained more than 50% of B-1 cells. Inventors compared bright field, and oil red O staining and fluorescent image, and combined oil red O with hematoxylin staining Oil red O staining indicated accumulated lipids in dying cancer cells.

Inventors also showed active accumulation of L2pB1 cells inside tumor PZTD mice were injected with 0.5 million B16F10 melanoma cells. Tumors were dissected on day 18 post injection. Tumor infiltrating lymphocytes (TIL) were obtained by proteolytic dissociation of the tumor cells to obtain a single cell suspension by gentle collagenase digestion. The lymphocytes were then further separated from tumor and dead cells by percoll gradient purification, following standard protocols. Lymphocytes were subjected to immunophenotyping by FACS staining with fluorescently-labeled antibody specific for CD45, CD3e, CD19, B220, IgM, PD-L2. Transgenic mice also express ZsGreen in L2pB1 cells. Inventors showed representative FACS analysis showing PD-L2+ZsGreen+L2pB1 cells in tumor, draining lymph nodes and spleen. The percentage of L2pB1 cells in total B cells was plotted and significantly more L2pB1 cells were shown to be present inside tumor than in draining lymph nodes or spleen.

Inventors showed that depletion of L2pB1 cells diminishes the growth inhibition effect of PCW on tumor spheroids B16F10 melanoma cells were cultured in Corning spheroid ultra-low attachment microplate to form 3D spheroids. Inventors used calcein AM (green florescent) and PI (red florescent) staining to evaluate tumor spheroids formation with the increase of PI staining positive necrotic core, which starts to appear on day 4. Calcein AM positive live cells were observed as a typical green ring around the spheroid surrounding the red necrotic core. 3D tumor spheroid growth was shown in the presence of PCW cells from PBS-injected and DT-injected CD19-Cre-PZTD mice, in comparison with untreated control and spleenocytes. On day 0, 104 B16F10 melanoma cells were seeded and on day 4, uniform 3D tumor spheroids were formed. Wild type PCW (PCW-PBS), L2pB1-depleted PCW (PCW_DT) and wild type spleenocytes (Spleen) were added to the spheroids respectively. L2pB1-depleted PCW (PCW-DT) were obtained from transgenic mice expressing Diphtheria toxin receptor in L2pB1 cells, and thus depleted upon injection with Diphtheria toxin (DT). PCW-PBS and splenocytes were obtained from the same transgenic mice that received PBS injection. Tumor spheroid size was measured using Celligo image cytometer on day 4, 6, 8, 10 and 12. Average area of at least 6 wells of tumor spheroids were plotted over each time point. P values between each two groups were shown for day 10 and day 12.

Inventors also showed that depletion of L2pB1 cells in vivo result in larger tumor size. CD19-Cre-PZTD transgenic male mice received i.p. injection of PBS or diphtheria toxin (DT) for 4 days before they were inoculated with 10^6 B16F10 melanoma cells. Mice were sacrificed 10-14 days post inoculation. Inventors showed representative images of the tumors in vivo, which were imaged and dissected for weight measurement. Inventors measured the weight of the tumor size. Average of 70% reduction of L2pB1 cells in DT-injected mice was seen at end point compare to PBS-injected mice. DT-injected mice show significant increase of tumor size and weight ($P<0.05$). Female mice showed similar results. Depletion of L2pB1 cells was evaluated by FACS analysis of the peritoneal cavity washout cells.

Inventors also showed that IgM from LPS stimulated peritoneal cells (PCW) but not spleen cells (SP) recognize melanoma cells. Mouse peritoneal cells contain about 20% NIMPAB cells, whereas spleen cells contain 40% conventional B-2 B cells and less than 1% B-1 B cells. Equal amount of PCW and SP cells were stimulated with 1 ug/ml of LPS for 48 hours to activate all B cells to produce immunoglobulin. Supernatant was collected at the end of 48 hours and then incubate with mouse melanoma cancer cells of the same strain. Secondary anti-IgM antibody conjugated with AF488 fluorochrome (green fluorescence) was used to stain and visualize any binding of IgM antibody to the cancer cells. Hoechst (blue fluorescence) was used to counter stain the nuclei of all cells.

Inventors produced a human hybridoma fusion. Inventors performed a pilot fusion experiment using a model human IgM secreting cell and myeloma partner cell line. After the fusion, cells went through an Ouabian-HAT double selection for 2~4 weeks. Microscopic image shows that inappropriately fused cells die in the double selection media. By 3 weeks, mono-clones start to show in the tissue culture plate (Day 21 column).

Figure 10A:
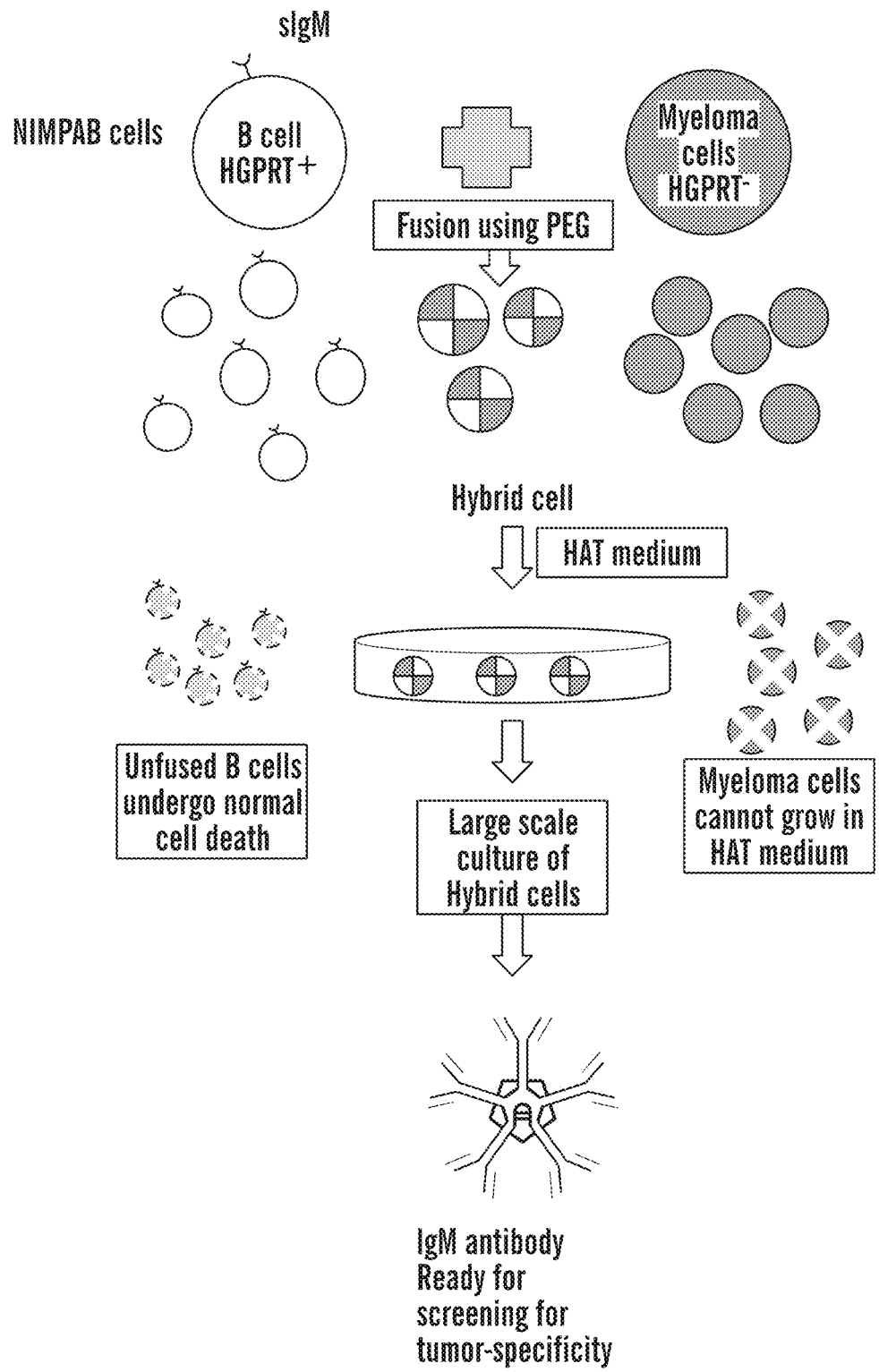
FIGS. 10A-10B show human hybridoma fusion.

Inventors proposed a schematic of the screening of human NIMPAB hybridoma clones for tumor-specificity (see, e.g., FIG. 10A). A tissue micro-array (TMA) can be generated from 50~100 melanoma patient tissue blocks. Supernatant of the NIMPAB hybridoma clones containing natural IgM are used for immunohistochemistry (IHC) analysis. Hybridoma clones that only bind tumor TMA but not control normal TMA will be selected.

Inventors also showed that B16F10 melanoma cells cultured in Corning spheroid ultra-low attachment microplate to form 3D spheroids. They demonstrated that the same amount of peritoneal Cavity Washout (PCW) cells, but not splenocytes (SP), inhibit syngeneic melanoma cell growth. The same amount of PCW cells or splenocytes were co-incubated with tumor spheroids. Tumor spheroid size was measured using Celligo image cytometer. Tumor growth was calculated as tumor size over time. In the presence of PCW cells, but not spleenocytes, tumor growth was inhibited. Uniform 3D tumor spheroids were formed by day 4 after seeding. Then wild type PCW (PCW-PBS) and spleenocytes (SP-PBS) were added to the spheroids. L2pB1-depleted PCW (PCW-DT) and spleennocytes (SP-DT) were obtained from transgenic mice injected with Diphtheria toxin (DT) and added to the spheroids. After 48-hour co-culture, tumor spheroids were imaged. Same sized red circles were overlaid to show the area change of the tumor spheroids. PCW-PBS treated spheroids were shrunk after 48 hours whereas less shrinkage was observed in spheroids co-cultured with PCW-DT. No significant changes were observed in splenocytes treated spheroids.

The inventors showed that mouse NIMPAB (B-1) cells phagocytose dying cancer cell. Breast cancer cell line 7367 were grown to 50% confluence on glass-bottom tissue culture dishes. Cancer cells were treated with 0.4 µg/ml Doxorubicin or 0.6 µg/ml Paclitaxel Peritoneal washout (PCW) was collected from WT C57BL/6 mice and stimulated with 1 ug/ml LPS. After 24 hours, cancer cells were labeled with CFSE (green), whereas PCW cells were stained with CD19-AF405 (Blue) and CD5-APC (pink). Cancer cells and PCW cells were co-cultured in the presence of LPS for 48 hours and 72 hours. Microscopic analysis was performed. B1 B cells were seen as large blue cells whereas B2 B cells are small round cells. B1 B cells became plasma/macrophage like cells after 48 hours of stimulation and closely interacted with cancer cells. Apoptotic bodies and microvesicles were seen.

Cancer immunotherapy is an exemplary application for the IgM antibodies that can be produced in large scale using the methods of the invention.

The problem with most antibodies used in immunotherapy is the use of xeno-immunization to obtain cancer-specific antibodies. These antibodies are generated by other species through conventional immunization protocols that elicit adaptive immune responses for foreign antigens. However essentially all tumor antigens, with the exception of virus-induced cancer cells, are self-antigens, not foreign antigens. The immune response to self is very different than the adaptive immune response to foreign antigens. Using the conventional immune response to target cancer is like asking the foreign affairs department to handle internal affairs. It can still do the job but will have low efficiency and have many side effects, including cross-reactivity to normal tissues, systemic inflammation and drug resistance.

Antibody-based cancer therapy is currently the major branch of cancer immunotherapy. However, the traditional approach of obtaining anti-cancer antibodies—which starts by identifying tumor antigen (TA) or biomarkers (e.g., check point (CP) ligand or receptors), followed by raising monovalent IgG antibodies via xeno-immunization and subsequent hybridoma formation—has been proven to be highly inefficient. First, there essentially is no TA that is not also a self-antigen, with the exception of virus-induced tumor. Second, cancer cells are always evolving and will become easily resistant to single-target or even multi-target treatment with monoclonal antibodies. Clinical evidence suggests that new mutations are actually induced by many treatments so that the cancer cells can bypass the blockage. Third, an antibody obtained from xeno-immunization typically requires significant humanization and bioengineering before it can be used for human treatment. Moreover, an antibody targeting immune cell regulatory biomarkers or signaling pathways will always encounter inflammation control issues. As a result, very few such antibodies significantly improve cancer outcomes. Despite extensive development of the TA-targeted antibodies, only 20~30% of the patients responded. Even with the new wave of check point (CP) biomarker targeted antibodies, the response rate hits similar limits.

The major limitations of both TA-targeted and CP-targeted therapeutic antibodies include, but are not limited to:

difficulty to identify real tumor-specific antigens without cross-reacting with normal tissue; difficulty to obtain antibodies with optimal combination of affinity and avidity to target cancer cells, but not normal cells; difficulty to control downstream signaling cascade and avoid inflammatory consequences (e.g. cytokine storm). (This is for CP or other signal pathway-targeted antibodies); limited window of efficacy due to cancer evolution.

Despite these limitations, roughly $40 billion is spent annually on cancer immunotherapy, and this expenditure is expected to double by 2020. The global cancer immunotherapy market is expected to reach USD 119.39 Billion by 2021 from USD 61.97 Billion in 2016, at a compound annual growth rate (CAGR) of 14.0% from 2016 to 2021. The cancer immunotherapy market is composed of the following 4 major types of therapy: Monoclonal Antibodies-based therapy; Cancer Vaccines; Checkpoint Inhibitors-based therapy; and immunomodulators, among others.

With shortages of efficient and fewer inflammatory therapeutic anti-cancer antibodies, current approaches have focused on identifying more TAs and biomarkers and combining more and more different antibodies or engineering bi-specific or tri-specific antibodies.

Such combinations do not solve the long-term problem of drug resistance due to constant tumor evolution. Even worse, it will exacerbate downstream signaling and worsen inflammatory side effects. Consequently, patients may suffer from the cascade of side effects more than the cancer itself Described are:

A composition comprising a natural IgM-producing phagocytic lymphocyte (NIMPAB) cell; and at least one particle comprising a superparamagnetic iron oxide nanoparticle (SPION).

The composition comprising a natural IgM-producing phagocytic lymphocyte (NIMPAB) cell; and at least one particle comprising a superparamagnetic iron oxide nanoparticle (SPION), wherein the SPION is dispersed in poly (lactic-co-glycolic acid) (PGLA) core and the core is coated with a lipid bilayer comprising phosphatidylcholine (PtC) and polyethyleneglycol (PEG).

The composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG).

The composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG), wherein the aqueous solution core comprises a stabilizer.

The composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG), wherein the aqueous solution core comprises a stabilizer, wherein the stabilizer is a catechol group modified poly (2-acrylamido-2-methyl-1-propanesulfonic acid) (pAMPS*) and the pH of the aqueous solution core is neutral.

The composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG), wherein the aqueous solution core comprises a stabilizer, wherein the SPION is coated with citric acid and the pH of the aqueous solution core is between or at about 8 and about 9.

The composition comprising a natural IgM-producing phagocytic lymphocyte (NIMPAB) cell; and at least one particle comprising a superparamagnetic iron oxide nanoparticle (SPION); the composition comprising a natural IgM-producing phagocytic lymphocyte (NIMPAB) cell; and at least one particle comprising a superparamagnetic iron oxide nanoparticle (SPION), wherein the SPION is dispersed in poly (lactic-co-glycolic acid) (PGLA) core and the core is coated with a lipid bilayer comprising phosphatidylcholine (PtC) and polyethyleneglycol (PEG); the composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG); the composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG), wherein the aqueous solution core comprises a stabilizer; the composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG), wherein the aqueous solution core comprises a stabilizer, wherein the stabilizer is a catechol group modified poly (2-acrylamido-2-methyl-1-propanesulfonic acid) (pAMPS*) and the pH of the aqueous solution core is neutral; or the composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG), wherein the aqueous solution core comprises a stabilizer, wherein the SPION is coated with citric acid and the pH of the aqueous solution core is between or at about 8 and about 9; and wherein the NIMPAB cell is a mammalian, for example, human, primate or murine NIMPAB cell, for example a human NIMPAB cell.

The composition comprising a natural IgM-producing phagocytic lymphocyte (NIMPAB) cell; and at least one particle comprising a superparamagnetic iron oxide nanoparticle (SPION); the composition comprising a natural IgM-producing phagocytic lymphocyte (NIMPAB) cell; and at least one particle comprising a superparamagnetic iron oxide nanoparticle (SPION), wherein the SPION is dispersed in poly (lactic-co-glycolic acid) (PGLA) core and the core is coated with a lipid bilayer comprising phosphatidylcholine (PtC) and polyethyleneglycol (PEG); the composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG); the composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG), wherein the aqueous solution core comprises a stabilizer; the composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG), wherein the aqueous solution core comprises a stabilizer, wherein the stabilizer is a catechol group modified poly (2-acrylamido-2-methyl-1-propanesulfonic acid) (pAMPS*) and the pH of the aqueous solution core is neutral; or the composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG), wherein the aqueous solution core comprises a stabilizer, wherein the SPION is coated with citric acid and the pH of the aqueous solution core is between or at about 8 and about 9; wherein the particle is 200-600 nm, for example 200-300, for example 300-600 nm, for example 400-600 nm, for example 500-600 nm in diameter, and optionally, wherein the NIMPAB cell is a mammalian, for example, human, primate or murine NIMPAB cell, for example a human NIMPAB cell.

The composition comprising a natural IgM-producing phagocytic lymphocyte (NIMPAB) cell; and at least one particle comprising a superparamagnetic iron oxide nanoparticle (SPION); the composition comprising a natural IgM-producing phagocytic lymphocyte (NIMPAB) cell; and at least one particle comprising a superparamagnetic iron oxide nanoparticle (SPION), wherein the SPION is dispersed in poly (lactic-co-glycolic acid) (PGLA) core and the core is coated with a lipid bilayer comprising phosphatidylcholine (PtC) and polyethyleneglycol (PEG); the composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG); the composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG), wherein the aqueous solution core comprises a stabilizer; the composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG), wherein the aqueous solution core comprises a stabilizer, wherein the stabilizer is a catechol group modified poly (2-acrylamido-2-methyl-1-propanesulfonic acid) (pAMPS*) and the pH of the aqueous solution core is neutral; or the composition comprising a natural IgM-producing phagocytic lymphocyte (NIMPAB) cell; and at least one particle comprising a superparamagnetic iron oxide nanoparticle (SPION), wherein the SPION is dispersed in aqueous solution core and the core is coated with a lipid bilayer comprising phosphatidylcholine (PtC) and polyethyleneglycol (PEG), wherein the aqueous solution core comprises a stabilizer, wherein the SPION is coated with citric acid and the pH of the aqueous solution core is between or at about 8 and about 9; wherein the particle is 200-600 nm, for example 200-300, for example 300-600 nm, for example 400-600 nm, for example 500-600 nm in diameter, and wherein the SPION is 10-80 nm, for example 10-20 nm, for example 12-18 nm, for example 13-15 nm in diameter, and optionally, wherein the NIMPAB cell is a mammalian, for example, human, primate or murine NIMPAB cell, for example a human NIMPAB cell, and optionally, wherein at least one particle is inside the NIMPAB cell, and optionally, wherein the composition comprises at least 30%, at least 40%, at least 50%, at least 60%, at least 70%, at least 80%, at least 90%, or at least 95% of cells that are NIMPAB cells comprising at least one particle inside the NIMPAB cell.

Provided is also a method for producing a cell sample enriched with natural IgM-producing phagocytic lymphocyte (NIMPAB) cells, the method comprising the steps of ex vivo contacting a particle comprising a superparamagnetic iron oxide nanoparticle (SPION) with a dissociated cell sample in a container thereby forming a mixture of the particles and dissociated cells, wherein the at least one particle comprising the SPION is dispersed in poly (lactic-co-glycolic acid) (PGLA) core and the core is coated with a lipid bilayer comprising phosphatidylcholine (PtC) and polyethyleneglycol (PEG); or wherein the SPION is dispersed in aqueous solution core and the core is coated with a lipid bilayer comprising phosphatidylcholine (PtC) and polyethyleneglycol (PEG) and optionally, wherein the aqueous solution core comprises a stabilizer, for example, a catechol group modified poly (2-acrylamido-2-methyl-1-propanesulfonic acid) (pAMPS*) and wherein the pH of the aqueous solution core is neutral; or wherein the SPION is coated with citric acid and the pH of the aqueous solution core is between or at about 8 and about 9; incubating the mixture in a container to allow phagocytosis of at least one of the particles by a NIMPAB cell present in the dissociated cell sample; contacting the container with a magnet to attract the cell that has phagocytosed the particle to the part of the container in contact with the magnet; discarding the dissociated cells not attracted to the magnet thereby obtaining a cell sample enriched with NIMPAB cells; dissociating the magnet and the container; optionally washing the cell sample enriched with NIMPAB cells; and optionally subjecting the cell sample enriched with NIMPAB cells to fluorescent activated cell sorting, wherein the dissociated cell sample is of mammalian, for example human, primate or murine origin, for example human origin; and wherein the dissociated cell sample is a blood sample, such as peripheral or cord blood sample or a sample made of a tumor tissue.

In the method, the particle is 200-600 nm, for example 300-600 nm, for example 400-600 nm, for example 500-600 nm in diameter; and the SPION is 10-80 nm, for example 10-20 nm, for example 12-18 nm, for example 13-15 nm in diameter.

Provided is also an isolated natural IgM-producing phagocytic lymphocyte (NIMPAB) cell comprising at least one superparamagnetic iron oxide nanoparticle (SPION) produced by any of the isolation methods described herein.

Provided is also a method for producing tissue-specific IgM antibodies comprising the steps of producing a hybridoma cell by fusing an isolated NIMPAB cell of claim 16 with an immortalized cell; exposing the hybridoma cell to an optimal culture medium for a time sufficient to allow production of IgM antibodies thereby causing production of IgM antibodies; optionally screening for IgM antibodies against the tissue-sample; optionally isolating the IgM antibodies against the tissue-sample; and optionally purifying the isolated IgM antibodies against the tissue-sample, wherein the immortalized cell is of mammalian origin, for example human, primate or murine origin, and wherein optionally, the immortalized cell is selected from a human Karpas 707 cell, a human B6B11 or B6B10 cell or a mouse SP20 cell, wherein the tissue-sample is a blood sample, for example peripheral or cord blood sample, or a sample from a tumor tissue, for example a solid tumor, for example a sarcoma, carcinoma, or a lymphoma, or wherein the tissue sample is from a melanoma or leukemia.

Also provided is a method for the treatment of disease comprising administering to a subject affected with the disease an IgM antibody produced by the isolation and production methods described herein, wherein the disease is cancer, for example a solid tumor, for example a sarcoma, carcinoma, or a lymphoma, or wherein the cancer is a melanoma, or a leukemia, or an autoimmune disease.

This invention is further illustrated by the following examples which should not be construed as limiting.

EXAMPLES

A reagent that only targets cancer cells but not normal cells is the central challenge of all cancer therapy. The technology described herein is directed to methods and compositions that isolate naturally existing human B cells in a subject that make special antibodies that recognize only cancer and not normal cells.

Most antibodies used in current immunotherapy are generated through xenoimmunization, i.e. immunizing another species with a tumor antigen or biomarker. The resulting antibody is generated by activated conventional B lymphocytes. There are two major concerns with this approach. Firstly, most tumor antigens and biomarkers are not unique to cancer cells. Essentially all tumor antigens (with the exception of virally induced cancer) are self-antigens that are expressed by normal cells and tissues. Therefore, antibodies against so-called tumor antigens or biomarkers will always encounter non-tumor cross-reactivity and consequently significant toxicity. Secondly, the effects of these antibodies are very limited due to the fact that cancer cells are always evolving and building up resistance to these antibody-based treatments.

Herein, the inventors have developed an approach to cancer immunotherapy based on a completely different immune aspect. Cancerous cells are constantly generated and quickly removed in healthy individuals. The immune components that circulate, scan and remove these cancerous cells on a daily base are part of the immunosurveillance system. However, the identity of these immune cells has not been clear.

The inventors herein have discovered a unique B lymphocyte population in both mouse and human that is termed Natural IgM-producing Phagocytic B Lymphocytes (NIMPAB). Different from conventional B lymphocytes, NIMPAB cells generate poly-reactive natural IgM antibodies that recognize patterns of cancer cells rather than a single epitope of an antigen or biomarker. The inventors demonstrate herein that NIMPAB cells could inhibit tumor cell growth, induce cell death and can phagocytose tumor cells. NIMPAB cells actively migrate and accumulate in tumors. Reducing NIMPAB cells in mice is associated with larger tumor formation and increased angiogenesis.

Figure 12:
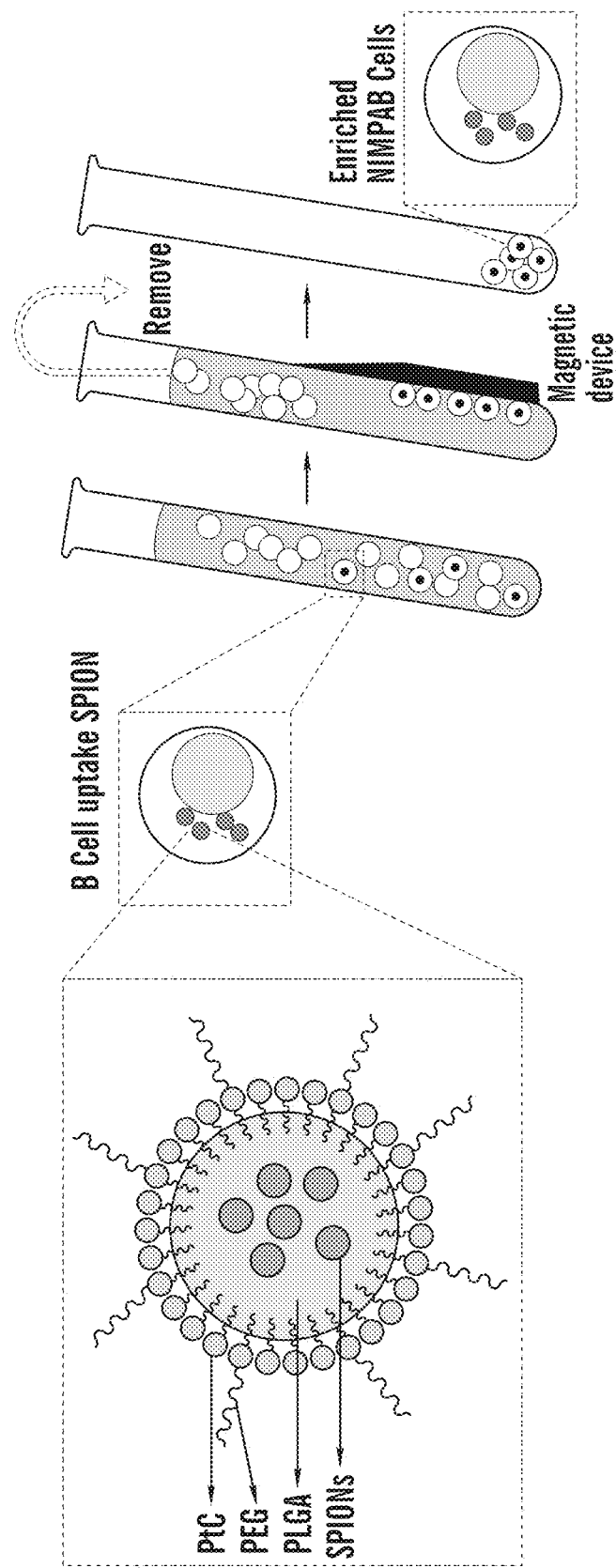
FIG. 12 is a schematic design of an embodiment of the nanoparticle, NIMPAB cell phagocytosis of the particle and rapid magnetic enrichment.

Herein, the inventors have developed a modified iron-core-nanoparticle-based method to quickly identify, enrich and isolate NIMPAB cells from human samples (FIGS. 8 and 12). This is based on the inventors' research demonstrating the unique Phosphatidylcholine (PtC)-specific phagocytic function of the NIMPAB cells.

Example 1

Generation of Hybrid Lipid-Iron Nanoparticles and Toxicity Testing.

Herein, the inventors have assessed at least 3 formulations of the nanoparticles to achieve the maximal amount of iron per particle and maximum PtC surface decoration. The inventors separated NIMPAB cells from human blood samples with external magnet-responsive nanoparticles (500~600 nm diameter). Each nanoparticle core contains superparamagnetic iron oxide nanoparticles (SPIONs) (10 nm diameter). The magnetic core structure allows SPION to aggregate under an external magnetic field, hence transitioning from superparamagnetism to paramagnetism. The surface of each nanoparticle is then coated with PtC lipids. The inventors chose to incorporate PtC lipids into the system according to previous studies that have shown that NIMPAB cells are able to phagocytize PtC-coated silica nanoparticles around 500-600 nm in diameter (Vo, H et al. Immunity, Inflamm. Dis. 2015, 2 (4), 254-261). In Vo, in order to confirm the phagocytosis process, pH sensitive pHrodo-red was conjugated with PtC units that formed phospholipid bilayers on the surface of silica beads, where fluorescence intensity increases as pH decreases when beads are exposed to the cytosol after lysosome fusion. In contrast, herein and in order to reduce cell toxicity and prevent protein corona formation, polyethylene glycol (PEG) conjugated to a phospholipid was incorporated into the nanoparticle surface in addition to the PtC lipids.

First the inventors assessed a Route 1 design (FIG. 13), where poly (lactic-co-glycolic acid) (PLGA) is used, allowing hydrophobic SPION embedment in the nanoparticle core. Due to the PLGA hydrophobicity, a single layer of PtC, lipid-pHrodo-red, lipid-PEG can form on the nanoparticle core. PtC allows specific engulfment of NIMPAB; lipid-pHrodo can be used to confirm the phagocytosis process; lipid-PEG can allow nanoparticle dispersion in the human blood sample prior internalization of NIMPABs. After dispersing nanoparticles in the blood sample, NIMPAB phagocytosis is allowed to occur overnight, then an external magnet is placed on the side of the sample tube for several minutes. During this time, aggregation of SPIONs occurs, and the nanoparticles become paramagnetic and pull NIMPABs out to the side-wall of the sample tube. Cell separation is followed by washing, and flow cytometry to further access and purify cells, and separate possible contamination of activated macrophages from NIMPAB cells.

Route 1 allows easy tuning of nanoparticle core size, SPION concentration, and diffusivity of SPIONs in the PLGA core, in order to achieve responsive paramagnetism, while changing magnetic sensitivity. If the tuning process cannot achieve superparamagnetism-paramagnetism transition, or cannot exert desired magnetic force on cells, additional routes can be utilized, such as Routes 2 and 3 (FIG. 14), where hydrophilic SPIONs are dispersed in an aqueous environment inside of lipid bilayers, where the chemical composition of the lipid coating is the same as Route 1. In Routes 2 and 3, SPIONs do not aggregate in the nanoparticle core, hence SPIONs need to be stabilized with coatings in an aqueous environment. For Route 2 (FIG. 14B), catechol group modified poly (2-acrylamido-2-methyl-1-propanesulfonic acid) (pAMPS*) can be used to allow single SPION dispersion in pH neutral aqueous environment. For Route 3 (FIG. 14C), citric acid-coated SPIONs can be dispersed in a pH 8-9 aqueous environment inside lipid bilayers.

Surface coating density (number molecules per $nm^2$) of lipid-pHrodo-red, and lipid-PEG can influence the time and efficiency of phagocytosis, lysosome diffusion, and exocytosis. Accordingly, one of ordinary skill in the art can optimize the ratio between PtC:lipid-pHrodo-red:lipid-PEG. If surface groups of pHrodo-red or PEG prevent any of these three processes, one of ordinary skill can also use Route 4 (FIG. 15A), where each SPION is coated with (3-aminopropyl)triethoxysilane (APTS) linked rhodamine green dye (FIG. 15B). The SPIONs are then encapsulated with a single PtC-lipid layer. Resulting nanoparticles from Route 4 only contains PtC on its surface, with fluorescence in the core for cell tracking.

Example 2

Assessment of Toxic Effects of Nanoparticles on Cells

The inventors have developed a particle that can be phagocytosed specifically by NIMPAB cells, and optionally, can be evaluated by pH-Rodo dye to distinguish the surface and internalized particle. In some embodiments, the particle does not kill the cells (as evaluated by AOPI staining of the cells), with the NIMPAB cells retaining the capacity to produce IgM (as evaluated by, e.g., a LPS stimulation and ELISA assay).

Optimization of NIMPAB Cell Nanoparticle Phagocytosis and Magnetic Isolation.

The inventors assessed the phagocytosis efficiency of the NIMPAB cells to achieve the optimal particle per cell density to allow maximal magnetic strength for quick isolation of peripheral NIMPAB cells. Different formulations of the particle were compared and evaluated by fluorescent microscopy and quantitative imaging analysis. The particle formulation that gives maximum particle per cell phagocytosis in NIMPAB cells that can be used, or further selected for analysis.

The inventors assessed the isolation efficiency and purity using flow cytometry analysis. Human blood samples or buffy coat are mixed with the optimal nano-particle (from experiment 2.1) at different ratios followed by incubation for 3 to 6 hours. Cells are split into two samples. One flows through a magnetic column. The other one is used as an unpurified control. Cells can be further stained with additional cell surface markers to distinguish different cell populations and analyzed by flow cytometry. A particle ratio and incubation time can be determined by determining the percentage of NIMPAB cells that phagocytosed the particle and the purity as compared to the control sample.

Example 3

Establish Human Hybridoma Fusion Protocol for Cloning Isolated NIMPAB Cells.

The inventors have isolated human NIMPAB cells from blood sample and fused with partner human cell line. Karpas 707, a hypoxathine-aminopterin-thymidine (HAT)-sensitive and ouabain-resistant human myeloma cell line was used as a fusion partner. NIMPAB cells isolated from PBMC were fused with Karpas 707 using the standard PEG fusion protocol. Hybridoma clones were assessed and selected for secretion of IgM antibodies. The hybridoma cells are cultured in HAT for 12 days, and the supernatant from each clone assessed for the secretion of IgM using standard ELISA. Immunohistochemistry (IHC) analysis was also used to test the specific binding of these monoclonal human IgM antibodies to human cancer tissue but not normal tissue.

IgM-positive clones were selected and expanded, and the supernatant of these clones used for IHC analysis on human cancer tissue microarray. Clones that secrete IgM that only react to tumor tissues and not normal tissues were selected.

Example 4

The B cell population that generates the natural anti-cancer IgM antibodies share many cell surface markers with other immune cells. Therefore, it is more difficult and less efficient to use traditional cell isolation methods such as magnetic beads that rely on cell surface markers or flow cytometry that uses antibodies specific for those markers. Herein, the inventors have demonstrated a method to rapidly enrich a rare anti-cancer-antibody-producing B cell population, and in contrast to existing technologies, utilizes a special phagocytosis feature unique to this population of B cells.

Herein, the inventors have assessed the magnetic properties of nanoparticles (NPs) against MACS beads (the most popular magnetic macro-beads on the market). The inventors demonstrate that a significantly higher percentage of the SPION nanoparticles (see FIG. 16) are pulled down by a magnet than for the MACS beads. This magnetic strength is important for maximizing enrichment efficiency to include small B cells that phagocytose a limited number of particles. Due to the scarcity of NIMPAB cells in the peripheral blood, it is calculated that it would take roughly 5 years using traditional flow cytometer-based sorting methods to obtain and screen a sufficient number (thousands) of hybridoma clones to identify a reasonable number of acceptable cancer-specific antibody-producing clones. By using the novel isolation, cloning and screening methods disclosed herein, the cycle time is expected to be a few months from patient sample to the development of a cancer-specific monoclonal antibody.

Instead of looking for single tumor antigen or biomarkers, the inventors have isolated and utilized naturally existing B cells that secrete anti-tumor natural IgM antibodies; these natural IgM antibodies differ from conventional antibodies used in most current immunotherapy in that they are low affinity, high avidity, poly-reactive and recognize cell patterns through lipid and carbohydrates modification and other macro-molecules like DNA and RNA. The inventors have utilized the unique features of these special B cells to create a rapid enrichment of these rare cell population from donor or patient blood without the need to extract them from tumor tissue.

The inventors demonstrate herein proof-of-principle experiments that demonstrate isolating NIMPAB cells as a source of broad-spectrum anti-cancer antibodies (FIG. 7). Briefly, IgM isolated from a NIMPAB cell-rich tissue (i.e. PCW) in a naïve animal recognizes melanoma cells, whereas IgM isolated from a NIMPAB cell-poor tissue (i.e. spleen) does not (FIG. 7). Similarly, Peritoneal Cavity Washout (PCW) cells, a NIMPAB-enriched population, clearly inhibit tumor spheroid growth whereas splenocytes, a NIMPAB-poor population, does not (FIG. 11).

In addition, a FACS (fluorescence activated cell sorting) study demonstrated that human NIMPAB cells identified from peripheral blood could ingest lipid-coated nanoparticles (FIG. 1C). Therefore, these data indicate that ingestion of magnetic lipid-coated particles is an a more efficient way to rapidly isolate these cells compared with traditional FACS approaches.

Example 5

Build Lipid Modified SPIONs (Superparamagnetic Iron Oxide Nanoparticles).

The inventors herein have developed magnetic nanoparticles (SPIONs) and used them in a protocol for isolating NIMPAB cells from human blood. The NP, also referred to as sNP, composition and methods as disclosed herein, is depicted in FIG. 8. The choice to coat iron oxide nanoparticles rather than commercially available magnetic macro-beads was based on the potential for large beads to have toxic post-ingestion effects based on their size, and on data showing superior performance of the disclosed SPIONs. This strong magnetic response (see FIG. 16) enables one to isolate B cells that phagocytose only a limited number of particles. Human NIMPAB cells can therefore be magnetically isolated from whole blood using the SPION nanoparticles disclosed herein and human NIMPAB cell enrichment can be compared to traditional FACS sorting methods.

Example 6

Human Hybridoma with Enriched Human Peripheral NIMPAB Cells.

Existing methods to produce IgM-producing hybridomas from NIMPAB cells purified from blood was performed. The inventors modified the standard human hybridoma fusion protocol for NIMPAB cells (FIG. 9A), and demonstrated that they could generate human hybridoma clones (FIG. 9B). The inventors obtained primary human cells from peripheral blood samples and other human tissues and fused with the human partner myeloma cell line.

Screening for Cancer-Specific NIMPAB Hybridoma Clones.

Figure 10B:
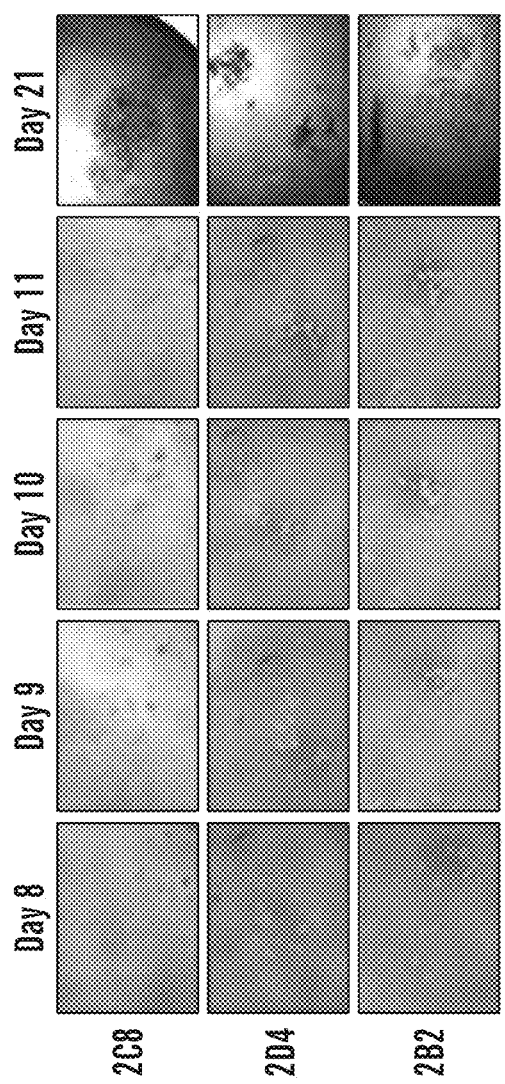

The inventors screened the hybridoma IgM antibodies for cancer specificity using a library of cancerous tissue microarray (TMA) (FIG. 10. Melanoma samples were used which are obtained retrospectively from previous skin biopsies of melanoma patients, with normal skin samples acting as an internal control.

In addition to previously obtained skin samples as above, and to allow for capture of future specimens to allow for larger scale analyses melanoma samples from skin biopsies can be assessed after obtaining patient consent at the time of biopsy.

Herein, the technology described herein uses a novel rapid isolation method to isolate NIMPAB cells from peripheral blood of patients of with specific types of cancer; or cancer survivor donors of the same specific type of cancer. The inventors have also demonstrated in vivo animal models of individual or pooled natural IgM antibody for late-stage melanoma, as well as established a human monoclonal NIMPAB hybridoma library from late-stage melanoma patients and obtain industry-scale production of the natural IgM antibodies for clinical trial use.

Immunotherapy has gained unprecedented attention in oncology in the past few years. 40% of $100 billion worldwide oncology drug spending is cancer immunotherapy in 2014. Recent success of check point-based immunotherapy also revealed many concerns over immune system-mediated severe side effects, and suboptimal response rates. The mainstream of the field is currently trending towards discovering more new check point targets and biomarkers, as well as combining different targeted therapies. However, these efforts do not solve the inherent problems of these severe inflammatory side effects, tumor heterogeneity and drug resistance due to cancer evolution, and may in fact speed up cancer evolution by selecting for cancer cells that outgrow the treatment.

Herein, the inventors have demonstrated that the technology described herein is a real innovation in this field and allows pattern recognition-based, tumor-antigen-independent targeting method.

Using this technology, the inventors can search for existing anti-tumor immune cells and antibodies in humans (both patients and healthy donors) rather than develop xenoantibodies de novo and avoids the need of molecular engineering to humanize them. Moreover, the technology described herein will likely be more effective and less toxic than existing products.

Example 7

The technology described herein can be used for the treatment of cancer. An exemplary cancer is melanoma, including but not limited to early-, mid- and late-stage melanoma patients.

Melanoma is a skin cancer which develops from the neoplastic transformation of melanocytes in the skin. Although melanoma accounts for less than one percent of skin cancer cases, it causes the vast majority of skin cancer deaths. The estimated 5-year survival rate for early stage melanoma is approximately 98 percent in the U.S. The survival rate falls to 62 percent when there is metastasis to the lymph nodes, and 18 percent when there is distant organ metastasis. Exposure to UV radiation remains the most important risk factor for developing melanoma.

Melanoma is one of the few remaining cancers in the US that is still increasing in incidence and it is now the fifth and seventh most common cancer in men and women respectively, in the US. Currently the lifetime risk of developing melanoma for Americans is 1 in 59. Deaths from melanoma are also on the increase. In 2017, it is estimated that there will be 87,110 new cases of melanoma of the skin and an estimated 9,730 people will die of this disease.

Current Immunotherapy Approaches for the Treatment of Melanoma and the Shortcomings of these Approaches are as Follows:

Recent greater understanding of the immunobiology of melanoma has led to the development and use of immunotherapy to treat metastatic melanoma. The most significant advances have come from the use of monoclonal antibodies against critical immunoregulatory pathways, in particular, immune checkpoint inhibitors. CTLA-4 is a critical checkpoint inhibitor expressed on regulatory T cells, where it downregulates T cell activation to prevent autoimmunity and allow self-tolerance. Ipilimumab, a monoclonal antibody which blocks CTLA-4 is FDA approved in the treatment of metastatic melanoma after showing improved survival for the first time in clinical trials of advanced stage melanoma patients. However, response rates are low ~11% and the use of this drug is associated with immune mediated toxicities leading to significant adverse events that can be life-threatening Another approach is to use monoclonal antibodies against another critical immune checkpoint molecule, PD-1, which is present on T cells in the effector phase. The ligand for PD-1 is PD-L1 which is expressed by many cancers including melanoma, and this binding contributes to tumor-induced immunosuppression, leading to tumor resistance to cytotoxic T cell responses.

Pembrolizumab is a humanized monoclonal antibody against PD-1 which is FDA approved for metastatic melanoma. Clinical trials in advanced melanoma have shown over-all response rates (ORR) of 34% with overall survival of 69% at 1 year. In head-to-head trials of pembrolizumab versus ipilimumab, pembrolizumab performed significantly better with ORR of 33% (pembrolizumab) versus 12% (ipilumumab). Although associated with immune mediated side-effects, they tended to be less frequent and severe in pembrolizumab compared to ipilimumab. A second PD-1 inhibitor approved for the treatment of advanced melanoma is nivolumab. Clinical trials in metastatic melanoma using the combination of a CTLA-4 inhibitor with a PD-1 inhibitor (ipilimumab and nivolumab) led to greater and more durable response rates than either drug alone (ORR nivolumab alone –44%; ipilimumab alone 19%; nivolumab+ipilimumab 58%). However, this benefit is counterbalanced by greater toxicity, grade ¾ (Adverse events: nivolumab alone –16%; ipilimumab alone 27%; nivolumab+ipilimumab 55%).

Although immunotherapy has made a significant impact in the management of advanced melanoma, there is still an inadequately met clinical need given the low response rates, together with significant immune mediated toxicities associated with the use of these drugs. Although combination immunotherapy has shown improved response rates, this is counterbalanced by worse toxicities. As a result, there is currently a search for predictive biomarkers that will predict which patients will benefit from these expensive treatments and which will not, and therefore spare patients from unnecessary adverse events. In addition, studies are ongoing to evaluate other combination immunotherapies, combination of immunotherapies with targeted therapies and the search for other immune checkpoint modulators. Thus although significant advances have been made with regards to immunotherapy in melanoma, there is still an inadequately met clinical need.

The use of NIMPAB cells and the technology described herein as a novel form of immunotherapy to treat advanced melanoma is likely to overcome many of the problems highlighted above. Given the 'pattern recognition' trait of NIMPAB cells versus targeting a specific cell epitope, they could more specifically target melanoma cells even when the melanoma evolves and tries to progress. This would suggest a more durable response. NIMPAB cells are generated and isolated by the patient themselves, therefore there is no need for humanization and bioengineering which is required of currently available xeno-immunization. This would predict NIMPAB cells to function more effectively and also reduce manufacturing costs. In addition to low cross-reactivity to normal tissue, they also function via pathways that are of low inflammation and cytotoxicity and so one would expect fewer adverse events with their use.

A clinical trial to assess natural IgM anti-melanoma antibodies for the treatment of melanoma can be performed. A study population can be determined (e.g adults, males and females, all ethnic groups, stage IV melanoma that has failed other FDA-approved therapies). Exclusion criteria will be determined (e.g pregnant or nursing women, or premenopausal women who refuse to take adequate contraception). The study design can be a Phase I trial, with the aim of the study to implement the cloned natural IgM anti-melanoma antibodies, and determine the feasibility, tolerability and safety of this drug in stage IV melanoma patients that have failed other FDA approved therapies. One can use a sample size would be 10 based on the number of subjects expected to meet eligibility criteria during the defined study period. Eligible patients will receive intravenous administration of cloned natural IgM anti-melanoma antibodies at predetermined intervals starting with the lowest dose for the first 3 cases and increasing the dose for the next 3 cases and so on, if symptoms allow.

Example 8

Immunotherapy has gained unprecedented attention in oncology in the past few years. 40% of $100 billion worldwide oncology drug spending is cancer immunotherapy in 2014. VC investment in fact doubled that year (data not shown). According to a 2016 report, the market will continue to more than double by 2020. As rapidly as it rises, investment in immunotherapy is expected to quickly reach saturation due to lack of out-of-box innovation in the field. Recent success of check point-based immunotherapy also revealed many concerns over immune system-mediated severe side effects, and suboptimal response rates. The mainstream of the field is currently trending towards discovering more new check point targets and biomarkers, as well as combining different targeted therapies. However, these efforts do not solve the inherent problems of these severe inflammatory side effects, tumor heterogeneity and drug resistance due to cancer evolution, and may in fact speed up cancer evolution by selecting for cancer cells that outgrow the treatment.

The technology disclosed herein represents a real innovation in this field, which is to create a pattern recognition-based, tumor-antigen-independent targeting method. The present technology disclosed herein provides both time- and money-saving because it allows one to search for the existing anti-tumor immune cells and antibodies in humans (both patients and healthy donors) rather than develop xenoantibodies de novo and use molecular engineering to humanize them. Moreover, the technology disclosed herein will be widely accepted by clinicians because it would likely be more effective and less toxic than existing products.

Example 9

Protocol for Synthesis of PtC-Coated Superparamagnetic Iron-Oxide Nanoparticles

Materials: Iron tri(acetylacetonate) (2 mmol), 1,2-tetradecanediol (10 mmol), oleic acid (6 mmol), oleylamine (6 mmol), dibenzyl ether, citric acid, diethyl ether, 2-methoxyethylamine, N-(3-Dimethylaminopropyl)-N'-ethylcarbodiimide hydrochloride (EDC), N-Hydroxysuccinimide (NHS), poly(D,L-lactide-co-glycolide), thioglycolic acid, hydroxylamine, chloroform, and phenanthroline were all purchased from Sigma-Aldrich (St. Louis, Mo.). 1,2-dichlorobenzene and N,N'-dimethylformamide were from Acros Organics (Morris Plains, N.J.). L-α-Phosphatidylcholine (Egg, Chicken) and 1,2-Dipalmitoyl-sn-Glycero-3-Phosphate were obtained from Avanti Polar Lipids (Alabaster, Ala.). NH2-PEG (550 Da, 2000 Da, 5000 Da, and 10000 Da) were all obtained from Laysan Bio, Inc. (Arab, Ala.). DSPE-PEG-NH-2, MW 2000 was purchased from Nanocs, Inc. (New York, N.Y.). Ethyl Alcohol 200 Proof was purchased from Pharmco-Aaper (Brookfield, Conn.). Slide-A-Lyzer G2 dialysis cassettes, chambered slides, bovine calf serum (BCS), dimethyl sulfoxide, pHrodo™ Red, succinimidyl ester, GE Healthcare filter devices, and centrifugal filter units were acquired from Thermo Scientific (Rockford, Ill.). Borate buffer was obtained from Boston Bio Products (Boston, Mass.).

Methods: (a) Superparamagnetic Iron Oxide (Fe-304) Nanoparticle (SPION) Synthesis. SPIONs were synthesized by a method presented by Sun et al. and further modified following a method described by Lattuada et al. Briefly, iron (III) tri(acetylacetonate) [Fe(acac)3] (2 mmol), benzyl ether (40 mL), 1,2-tetradecanediol (10 mmol), oleic acid (6 mmol), and oleylamine (6 mmol) were mixed and stirred magnetically under a flow of nitrogen. The mixture was heated at 2 degrees per min to 100° C. and kept for 45 min, followed by heating to 200° C. at 2 degrees per min and kept for 2 h. Subsequently the reaction mixture was heated to reflux (~300° C.) and held for another 30 min to 1 h. The oleic acid-coated SPIONs were stored after washing steps with an excess of ethanol and after a drying step in a vacuum oven. For hydrophilic water-soluble SPIONs, oleic acid-coated nanoparticles were dissolved in a dichlorobenzene and dimethylformamide mixture (1:1 v/v) with citric acid and heated to 100° C. for 24 h. Finally, the citric acid-coated SPIONs were further functionalized with amine-terminated polyethylene glycol (PEG) of varying chain lengths (550, 2000, 5000, and 10000 Da) or 2-methoxyethylamine (2-MEA) using N-hydroxysuccinimide (NHS) ester and 1-ethyl-3-(3-dimethylaminopropyl) carbodiimide (EDC) in pH 9 for 24 h on an agitator at room temperature. The PEG Fe NPs were obtained after they were dialyzed for 48 h against deionized water at pH 9.

Methods: (b) Secondary Lipid-Coated Nanoparticle Synthesis. The secondary nanoparticles are synthesized by combining a hydrophobic phase with a hydrophilic phase. Poly (D,L-lactide-co-glycolide) (6 mg), OA-SPIONs (3 mg), synthesized in 2.1, and chloroform (1 mL) were sonicated to form the hydrophobic phase. DSPE-PEG-NH-2 (0.563 µmol), L-α-Phosphatidylcholine (0.571 µmol), and 4% ethyl alcohol (3 mL) were magnetically stirred at 72° C. to make the hydrophilic phase. pHrodo-PE, used to dye the outside of the particle, was synthesized by conjugating pHrodo-succinimidyl ester to dipalmitoyl-sn-glycero-3-phosphoethanolamine-N-dodecanylamine overnight in a mixture of chloroform and DMSO. The hydrophilic phase, hydrophobic phase, and pHrodo-PE were combined using a tip sonicator at 30% power for 3 minutes. The lipid-coated nanoparticles were obtained after mixture was attached to a Rotovap on house vacuum for 15 minutes to bubble out remaining chloroform, washed through a centrifugal filter tube, and then through a 0.45 µm filter disk.

REFERENCES

The references noted herein and throughout this application are incorporated herein by reference in their entirety.

1. Azevedo M C, Palos M C, Osugui L, Laurindo M F, Masutani D, Nonogaki S, et al. B-1 cells and concomitant immunity in Ehrlich tumour progression. Immunobiology. 2014; 219(5):357-66. PMCID: 24556035.
2. Brandlein S, Eck M, Strobel P, Wozniak E, Muller-Hermelink H K, Hensel F, et al. PAM-1, a natural human IgM antibody as new tool for detection of breast and prostate precursors. Hum Antibodies. 2004; 13(4):97-104.
3. Brandlein S, Lorenz J, Ruoff N, Hensel F, Beyer I, Muller J, et al. Human monoclonal IgM antibodies with apoptotic activity isolated from cancer patients. Hum Antibodies. 2002; 11(4):107-19.
4. Brandlein S, Pohle T, Ruoff N, Wozniak E, Muller-Hermelink H K, Vollmers H P. Natural IgM antibodies and immunosurveillance mechanisms against epithelial cancer cells in humans. Cancer Res. 2003; 63(22):7995-8005. PMCID: 14633732.
5. Brandlein S, Rauschert N, Rasche L, Dreykluft A, Hensel F, Conzelmann E, et al. The human IgM antibody SAM-6 induces tumor-specific apoptosis with oxidized low-density lipoprotein. Mol Cancer Ther. 2007; 6(1):326-33.
6. Brandlein S, Vollmers H P. Natural IgM antibodies, the ignored weapons in tumour immunity. Histol Histopathol. 2004; 19(3):897-905.
7. Cabiedes J, Cabral A R, Lopez-Mendoza A T, Cordero-Esperon H A, Huerta M T, Alarcon-Segovia D. Characterization of anti-phosphatidylcholine polyreactive natural autoantibodies from normal human subjects. J Autoimmun. 2002; 18(2):181-90.
8. cellular antigen it recognizes is polysialic acid attached to the neural cell adhesion molecule (NCAM) and can serve as a therapeutic to stimulate functional improvement in multiple sclerosis patients and other
9. Chan L, X. Zhong, A. Pirani, B. Lin (2012) A novel method for kinetic measurements of rare cell proliferation using Cellometer image-based cytometry, Journal of Immunological Methods 377(1-2): 8-14.
10. Diaz-zaragoza M, Hernandez-avila R, Ostoa-saloma P. Recognition of tumor antigens in 4T1 cells by natural IgM from three strains of mice with different susceptibilities to spontaneous breast cancer Oncol Lett. 2017 January; 13(1): 271-274. PMCID: PMC5244975
11. Hansen M H, Nielsen H, Ditzel H J. The tumor-infiltrating B cell response in medullary breast cancer is oligoclonal and directed against the autoantigen actin exposed on the surface of apoptotic cancer cells. Proc Natl Acad Sci USA. 2001; 98(22):12659-64. PMCID: 60110.
12. Hazen S L. Oxidized phospholipids as endogenous pattern recognition ligands in innate immunity. J Biol Chem. 2008; 283(23):15527-31. PMCID: 2414290.
13. Hensel F, Timmermann W, von Randen B H, Rosenwald A, Brandlein S, Illert B. Ten-year follow-up of a prospective trial for the targeted therapy of gastric cancer with the human monoclonal antibody PAT-SC1. Oncol Rep. 2014; 31(3):1059-66. PMCID: 3926647.
14. Keast D. Immunosurveillance and cancer. Lancet. 1970; 2(7675):710-2. PMCID: 4195943.
15. Kotlan B, Simsa P, Teillaud J L, Fridman W H, Toth J, McKnight M, et al. Novel ganglioside antigen identified by B cells in human medullary breast carcinomas: the proof of principle concerning the tumor-infiltrating B lymphocytes. J Immunol. 2005; 175(4):2278-85. PMCID: 16081796.
16. Lattuada M, Hatton T A. Functionalization of monodisperse magnetic nanoparticles. Langmuir. 2007; 23:2158-2168.
17. Lee RA1, Mao C1, Vo H1, Gao W2, Zhong X1. Fluorescence tagging and inducible depletion of PD-L2-expressing B-1 B cells in vivo, Ann N Y Acad Sci. 2015 December; 1362:77-85. doi: 10.1111/nyas. 12865. Epub 2015 Aug. 20.
18. Loi S, Sirtaine N, Piette F, Salgado R, Viale G, Van Eenoo F, et al. Prognostic and predictive value of tumor-infiltrating lymphocytes in a phase III randomized adjuvant breast cancer trial in nodepositive breast cancer comparing the addition of docetaxel to doxorubicin with doxorubicin-based chemotherapy: BIG 02-98. J Clin Oncol. 2013; 31(7):860-7. PMCID: 23341518.

19. Marcela Leyva K H. B-1a cells suppress peritoneal carcinomatosis. Merinoff World Congress: B-1 cell development and function; Tarrytown House Estate and Conference Center 2014.
20. Mkrtichyan M, Najjar Y G, Raulfs E C, Liu L, Langerman S, Guittard G, et al. B7-DC-Ig enhances vaccine effect by a novel mechanism dependent on PD-1 expression level on T cell subsets. J Immunol. 2012; 189(5): 2338-47.
21. Park Y C, Smith J B, Pham T, Whitaker R D, Sucato C A, Hamilton J A, Bartolak-Suki E, Wong J Y. Effect of PEG Molecular Weight on Stability, T2 contrast, Cytotoxicity, and Cellular Uptake of Superparamagnetic Iron Oxide Nanoparticles (SPIONs), Colloids Surf B Biointerfaces. 2014 Jul. 1; 119:106-14. doi: 10.1016/j.colsurfb. 2014 .04. 027. Epub 2014 May 12.
22. Park Y, Whitaker R D, Nap R I, Paulsen J L, Mathiyazhagan V, Doerrer L H, et al. Stability of Superparamagnetic Iron Oxide Nanoparticles at Different pH Values: Experimental and Theoretical Analysis. Langmuir. 2012; 28:6246-6255.
23. R. A. Lee, C. Mao, H. Vo, W. Gao, X. Zhong, Fluorescence tagging and inducible depletion of PDL2-expressing B-1 B cells in vivo. Ann. N. Y. Acad. Sci, 2015 December; 1362(1):77-85. doi:10.1111/nyas. 12865. Epub 2015 Aug. 20.
24. Rasche L, Duell J, Castro I C, Dubljevic V, Chatterjee M, Knop S, et al. GRP78-directed Immunotherapy in relapsed or refractory multiple myeloma-results from a Phase 1 Trial with monoclonal IgM antibody PAT-SM6. Haematologica. 2015. PMCID: 25637055. (Both PAT-SC1 and PAT-SM6 are human natural IgM)
25. Thorne S H. The role of GM-CSF in enhancing immunotherapy of cancer. Immunotherapy. 2013; 5(8):817-9. PMCID: 23902549.
26. Urban J L, Schreiber H. Host-tumor interactions in immunosurveillance against cancer. Prog Exp Tumor Res. 1988; 32:17-68. PMCID: 3287449.
27. Vo H, Chiu J, Allaimo D, Mao C, Wang Y, Gong Y, Ow H, Porter T, Zhong X. High fat diet deviates PtC-specific B1 B cell phagocytosis in obese mice. Immun Inflamm Dis. 2014 December; 2(4):254-61. doi:10.1002/iid 3.41. Epub 2014 Dec. 15. PubMed PMID: 25866632; PubMed Central PMCID: PMC4386919.
28. Vollmers H P, Brandlein S. Death by stress: natural IgM-induced apoptosis. Methods Find Exp Clin Pharmacol. 2005; 27(3):185-91. PMCID: 15834451.
29. Vollmers H P, Brandlein S. Natural IgM antibodies: the orphaned molecules in immune surveillance. Adv Drug Deliv Rev. 2006; 58(5-6): 755-65. PMCID: 16820243.
30. Vollmers H P, Brandlein S. Nature's best weapons to fight cancer. Revival of human monoclonal IgM antibodies. Hum Antibodies. 2002; 11(4):131-42.
31. Vollmers H P, Brandlein S. The "early birds": natural IgM antibodies and immune surveillance. Histol Histopathol. 2005; 20(3):927-37.
32. Watzlawik J O, Painter M M, Wootla B, Rodriguez M. A human anti-polysialic acid antibody as a potential treatment to improve function in multiple sclerosis patients. J Nat Sci. 2015 August; 1(8). pii: e141. (HIgM12 is a human monoclonal antibody. This antibody is a poly-reactive natural IgM. One of the
33. Weber G F, Chousterman B G, Hilgendorf I, Robbins C S, Theurl I, Gerhardt L M, et al. Pleural innate response activator B cells protect against pneumonia via a GM-CSF-IgM axis. J Exp Med. 2014; 211(6):1243-56. PMCID: 4042649.
34. Woo J R, Liss M A, Muldong M T, Palazzi K, Strasner A, Ammirante M, et al. Tumor infiltrating B-cells are increased in prostate cancer tissue. J Trans 1 Med. 2014; 12:30. PMCID: 3914187.
35. Wynter J. Duncanson,a Kelleny Oum,b John R. Eisenbrey,b Robin O. Cleveland,c Margaret A. Wheatley,b and Joyce Y. Wonga Targeted binding of PEG-lipid modified polymer ultrasound contrast agents with tiered surface architecture, Biotechnol Bioeng. 2010 Jun. 15; 106(3): 501-506.
36. Zhong X, Bai C, Gao W, Strom T B, Rothstein T L. Suppression of expression and function of negative immune regulator PD-1 by certain pattern recognition and cytokine receptor signals associated with immune system danger. Int Immunol. 2004 August; 16(8):1181-8. Epub 2004 Jul. 5. PubMed PMID: 15237109.
37. Zhong X, Lau S, Bai C, Degauque N, Holodick N E, Steven S J, Tumang J, Gao W, Rothstein T L. A novel subpopulation of B-1 cells is enriched with autoreactivity in normal and lupus-prone mice. Arthritis Rheum. 2009 December; 60(12):3734-43. doi: 10.1002/art. 25015. PubMed PMID: 19950285; PubMed Central PMCID: PMC2868318.
38. Zhong X, Rothstein T L. L2pB1: a new player in autoimmunity. Mol Immunol. 2011 June; 48(11):1292-300. doi: 10.1016/j.molimm. 2010. 12. 006. Epub 2010 Dec. 31. Review. PubMed PMID: 21195478; PubMed Central PMCID: PMC3087825.
39. Zhong X, Tumang J R, Gao W, Bai C, Rothstein T L. PD-L2 expression extends beyond dendritic cells/macrophages to B1 cells enriched for V (H)11N(H)12 and phosphatidylcholine binding. Eur J Immunol. 2007 September; 37(9):2405-10. PubMed PMID: 17683117.
40. Zhong, X*, T. L. Rothstein. (2011) L2pB1 cells: a new player in autoimmunity. Molecular Immunology, 48(11): 122-300. *Corresponding author
41. Zhong, X., W. Gao, N. Degauque, C. Bai, Y. Lu, J. Kenny, M. Oukka, T. B. Strom, and T. L. Rothstein. (2007).Reciprocal generation of Th1/Th17 and T (reg) cells by B1 and B2 B cells. Eur J Immunol 37:2400-2404.

We claim:
1. A composition comprising
   a. A viable natural IgM-producing phagocytic lymphocyte (NIMPAB) cell; and
   b. at least one particle comprising a sufficient number of superparamagnetic iron oxide nanoparticles (SPIONs) for a superparamagnetism-paramagnetism transition to exert a magnetic force on a cell, wherein the SPION has a diameter of 10-80 nm,
      wherein the at least one particle has a diameter of between 200 nm-600 nm and comprises a lipid bilayer comprising phosphatidylcholine (PtC), and
      wherein the at least one particle is inside the viable NIMPAB cell.
2. The composition of claim 1, wherein the sufficient number of SPIONs are present in a poly (lactic-co-glycolic acid) (PGLA) core and the core is encapsulated with a lipid bilayer comprising phosphatidylcholine (PtC) and polyethyleneglycol (PEG).
3. The composition of claim 1, wherein the sufficient number of SPIONs are present in an aqueous solution, wherein the aqueous solution is encapsulated by a lipid bilayer comprising phosphatidylcholine (PtC) and polyethyleneglycol (PEG) to form an aqueous solution core.
4. The composition of claim 3, wherein the aqueous solution comprises a stabilizer.

5. The composition of claim 4, wherein the stabilizer is a catechol group modified poly (2-acrylamido-2-methyl-1-propanesulfonic acid) (pAMPS*) and the pH of the aqueous solution core is neutral.

6. The composition of claim 3, wherein the sufficient number of SPIONs are coated with citric acid and the pH of the aqueous solution is between or at about 8 and about 9.

7. The composition of claim 1, wherein the viable NIMPAB cell is a viable human NIMPAB cell.

8. A composition comprising a population of viable NIMPAB cells, wherein at least 40% of the cells in the population of NIMPAB cells comprising at least one particle inside the NIMPAB cell, wherein the at least one particle comprises a sufficient number of superparamagnetic iron oxide nanoparticles (SPIONs) for a superparamagnetism-paramagnetism transition to exert a magnetic force on the NIMPAB cell, wherein the SPION has a diameter of 10-80 nm, and the at least one particle has a diameter of between 200 nm-600 nm and comprises a lipid bilayer comprising phosphatidylcholine (PtC).

9. The composition of claim 1, produced by the steps of
(a) ex vivo contacting a dissociated cell sample in a container with a particle comprising a sufficient number of superparamagnetic iron oxide nanoparticles (SPIONs) for a superparamagnetism-paramagnetism transition to exert a magnetic force on a cell, wherein the SPION has a diameter of 10-80 nm thereby forming a mixture of the particles and dissociated cells,
wherein the at least one particle is between 200 nm-600 nm in diameter and the sufficient number of SPIONs are present in poly (lactic-co-glycolic acid) (PGLA) core and the core is encapsulated with a lipid bilayer comprising phosphatidylcholine (PtC) and polyethyleneglycol (PEG); or
wherein the at least one particle is between 200 nm-600 nm in diameter and the sufficient number of SPIONs are suspended in aqueous solution and the aqueous solution is encapsulated by a lipid bilayer comprising phosphatidylcholine (PtC) and polyethyleneglycol (PEG) to form an aqueous solution core;
(b) incubating the mixture in the container to allow phagocytosis of at least one of the particles by a NIMPAB cell present in the dissociated cell sample;
(c) contacting the container with a magnet to attract at least one cell that has phagocytosed the particle to the part of the container in contact with the magnet;
(d) discarding the dissociated cells not attracted to the magnet thereby obtaining a cell sample enriched with NIMPAB cells;
(e) dissociating the magnet and the container from each other;
(f) optionally washing the cell sample enriched with NIMPAB cells; and
(g) optionally subjecting the cell sample enriched with NIMPAB cells to fluorescent activated cell sorting.

10. The composition of claim 9, wherein the dissociated cell sample is of human origin.

11. The composition of claim 9, wherein the dissociated cell sample is a blood sample.

12. The composition of claim 9, wherein the dissociated cell sample is a sample made of a tumor tissue.

13. The composition of claim 9, wherein the aqueous solution comprises a stabilizer.

14. The composition of claim 13, wherein the stabilizer is a catechol group modified poly (2-acrylamido-2-methyl-1-propanesulfonic acid) (pAMPS*).

15. The composition of claim 9, wherein the aqueous solution has a neutral pH.

16. The composition of claim 9, wherein the sufficient number of SPIONs are coated with citric acid and the pH of the aqueous solution encapsulated by the lipid bilayer is between or at about 8 and about 9.

* * * * *